US011278676B2

(12) United States Patent
Hewson et al.

(10) Patent No.: US 11,278,676 B2
(45) Date of Patent: Mar. 22, 2022

(54) DOSE DELIVERY MECHANISM

(71) Applicant: NORTON HEALTHCARE LIMITED, West Yorkshire (GB)

(72) Inventors: Karl James Hewson, Cambridgeshire (GB); Jeremy James Robert Kooyman, Cambridgeshire (GB); Xorge Castro Pelayo, Cambridgeshire (GB); James Alexander Davies, Cambridgeshire (GB); Oliver Hart, Cambridgeshire (GB); Joshua Arieh Shenker, Cambridgeshire (GB); Matthew Alexander Morris, Cambridgeshire (GB); Matthew Keith Fordham, Essex (GB)

(73) Assignee: Norton Healthcare Limited, Castleford (GB)

( * ) Notice: Subject to any disclaimer, the term of this patent is extended or adjusted under 35 U.S.C. 154(b) by 122 days.

(21) Appl. No.: 16/332,044

(22) PCT Filed: Sep. 11, 2017

(86) PCT No.: PCT/EP2017/072748
§ 371 (c)(1),
(2) Date: Mar. 11, 2019

(87) PCT Pub. No.: WO2018/046728
PCT Pub. Date: Mar. 15, 2018

(65) Prior Publication Data
US 2019/0366006 A1 Dec. 5, 2019

(30) Foreign Application Priority Data
Sep. 12, 2016 (GB) ...................................... 1615447

(51) Int. Cl.
*A61M 5/315* (2006.01)
*A61M 5/20* (2006.01)
(Continued)

(52) U.S. Cl.
CPC ...... *A61M 5/31526* (2013.01); *A61M 5/2033* (2013.01); *A61M 5/24* (2013.01);
(Continued)

(58) Field of Classification Search
CPC .. A61M 5/31526; A61M 5/2033; A61M 5/24; A61M 5/31553; A61M 5/31583;
(Continued)

(56) References Cited

U.S. PATENT DOCUMENTS

2006/0153693 A1 7/2006 Fiechter et al.
2009/0254035 A1* 10/2009 Kohlbrenner ........... A61M 5/24
 604/135
2011/0077595 A1 3/2011 Eich et al.

FOREIGN PATENT DOCUMENTS

EP 2198906 B1 1/2016
WO 2006/045528 A1 5/2006
(Continued)

OTHER PUBLICATIONS

International Search Report and Written Opinion PCT/EP2017/072748, dated Dec. 18, 2017, 18 pages.

*Primary Examiner* — Amber R Stiles
*Assistant Examiner* — Avery Smale
(74) *Attorney, Agent, or Firm* — BakerHostetler

(57) ABSTRACT

An injection device comprising a housing having a longitudinal axis, a dose selector (16) capable of being rotated about said longitudinal axis with respect to said housing by a user to set a dose of medicament to be ejected from the injection device and a spring (20) capable of storing energy necessary for ejecting the dose of medicament from the (Continued)

injection device. The spring is coupled to the dose selector such that a charging force can be transferred from the dose selector to the spring to increase the energy stored by the spring. The injection device further comprises a ratchet arrangement (25) moveable between an engaged state in which the spring is limited from unwinding from a currently selected dose and a disengaged state in which the spring is able to unwind and a drive assembly including a plunger element (23) capable of providing an axial force for ejecting a dose of medicament from the injection device. The drive assembly further comprises a drive clutch (21) moveable from a disengaged state in which a force path from the spring to the plunger element is interrupted and an engaged state in which the drive assembly can provide the axial force for ejecting a dose of medicament from the injection device via said force path.

22 Claims, 71 Drawing Sheets

(51) Int. Cl.
*A61M 5/24* (2006.01)
*A61M 5/31* (2006.01)

(52) U.S. Cl.
CPC .... *A61M 5/31553* (2013.01); *A61M 5/31593* (2013.01); *A61M 2005/3126* (2013.01)

(58) Field of Classification Search
CPC . A61M 5/31593; A61M 5/31511; A61M 5/20
See application file for complete search history.

(56) References Cited

FOREIGN PATENT DOCUMENTS

| WO | 2007/063342 | A1 | 6/2007 | |
|----|---|---|---|---|
| WO | 2011/081867 | A2 | 7/2011 | |
| WO | 2012/089616 | A1 | 7/2012 | |
| WO | 2013/178372 | A1 | 12/2013 | |
| WO | 2014/001319 | A1 | 1/2014 | |
| WO | 2014/060369 | A1 | 4/2014 | |
| WO | 2014/166899 | A1 | 10/2014 | |
| WO | 2015/007820 | A1 | 1/2015 | |
| WO | WO-2015007820 | A1 * | 1/2015 | ........ A61M 5/31553 |
| WO | 2015/032780 | A1 | 3/2015 | |
| WO | 2015/071212 | A1 | 5/2015 | |
| WO | 2016/001299 | A1 | 1/2016 | |
| WO | 2016/055438 | A1 | 4/2016 | |

* cited by examiner

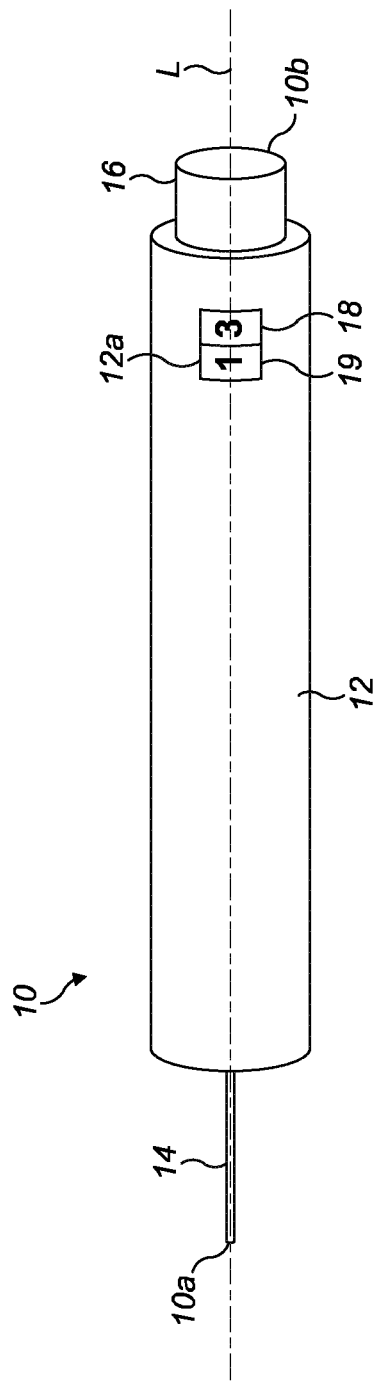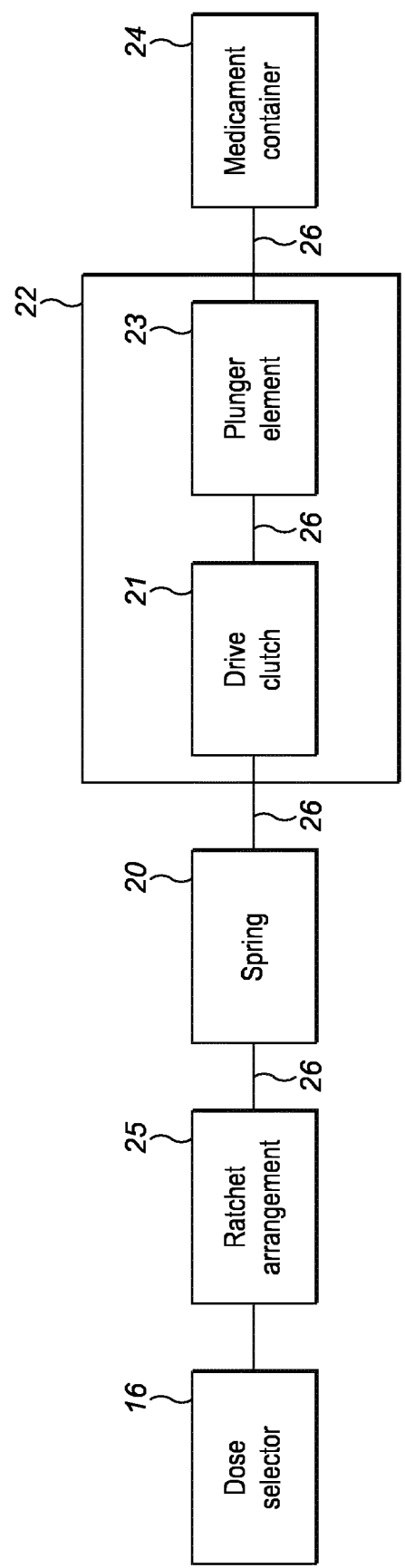

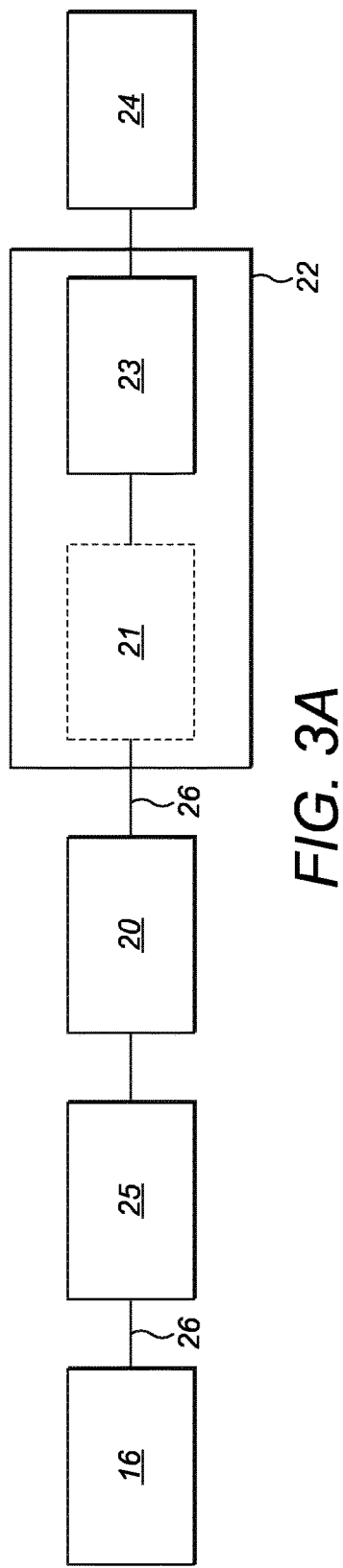
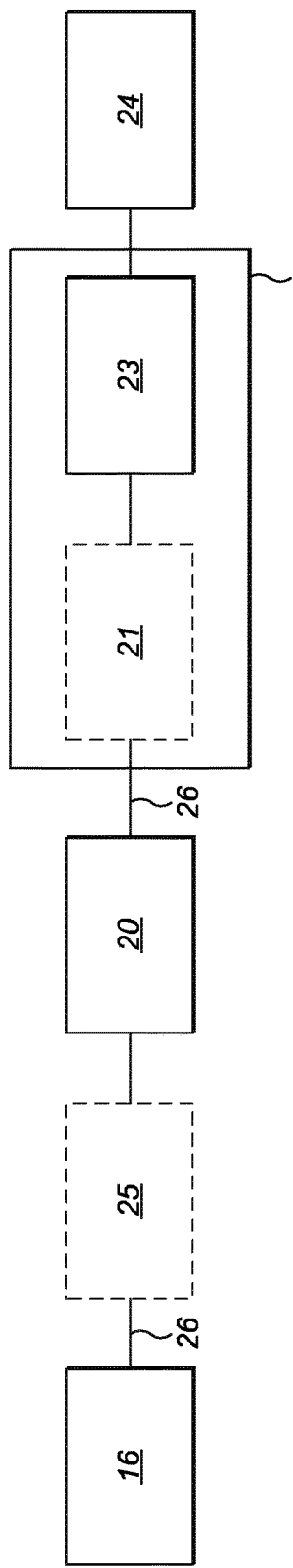
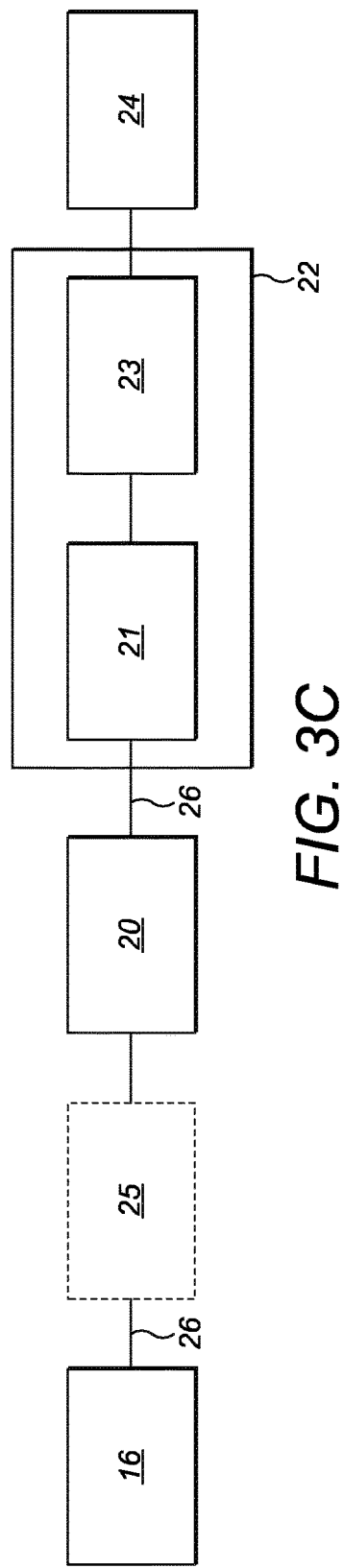

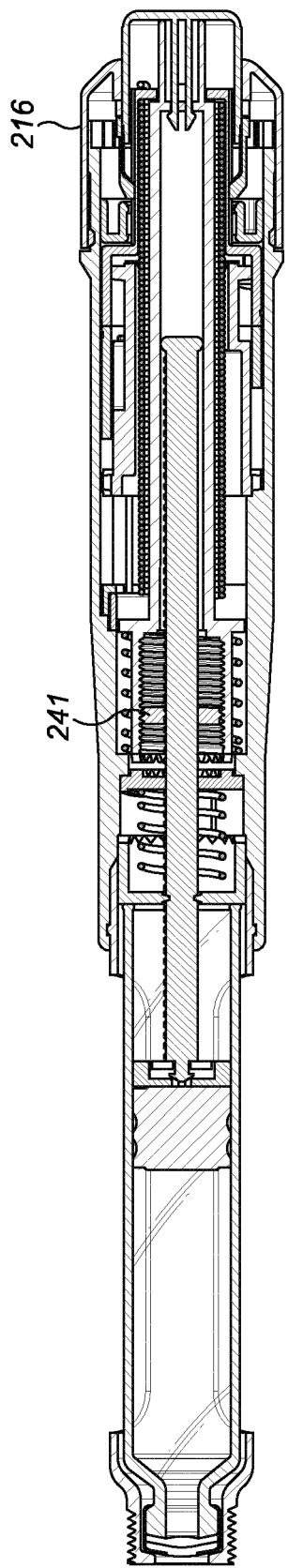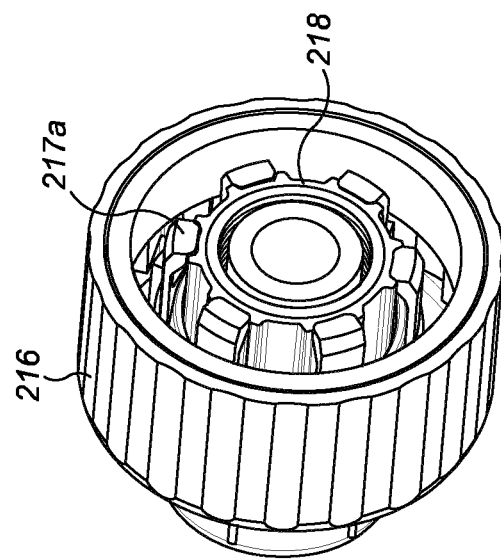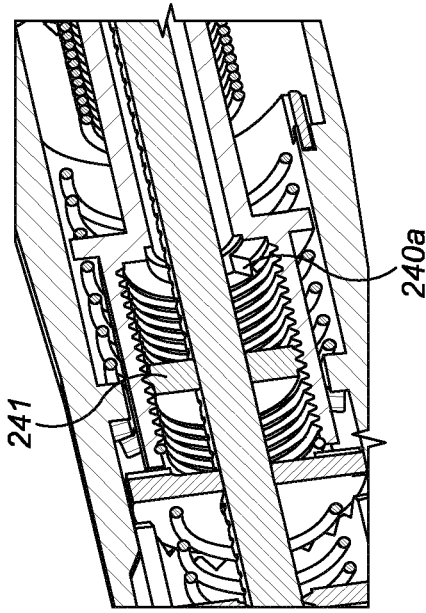
FIG. 13
FIG. 13B
FIG. 13A

| Key: | Not Engaged | Partially Engaged | Fully Engaged | |
|---|---|---|---|---|
| Advancement of dose button in mm | 0 mm | 2.5 mm | 4 mm | 5 mm |
| Drive sleeve 342/drive shaft clutch 350 (drive shaft connection to dose delivery subsystem) | | | | |
| Selector pawl 317/drive shaft splines 349 (drive shaft connection to dose setting subsystem) | | | | |
| Dose selecting hold ratchet (spring hold and haptic feedback for dose setting subsystem) | | | | |

FIG. 34

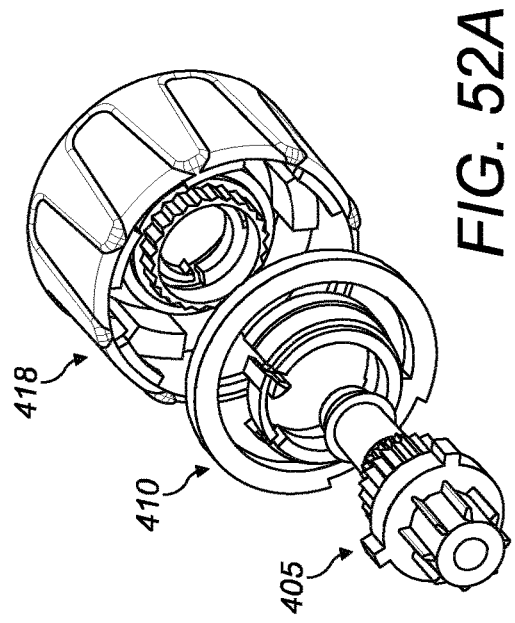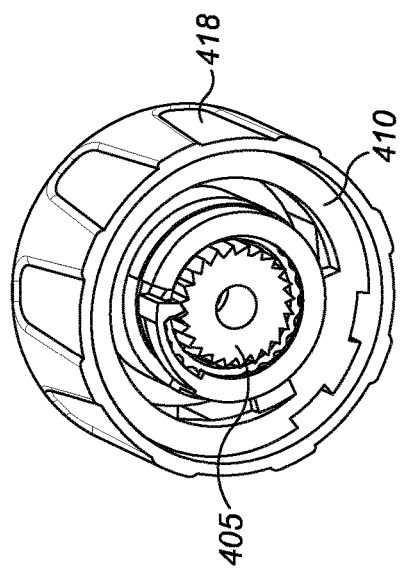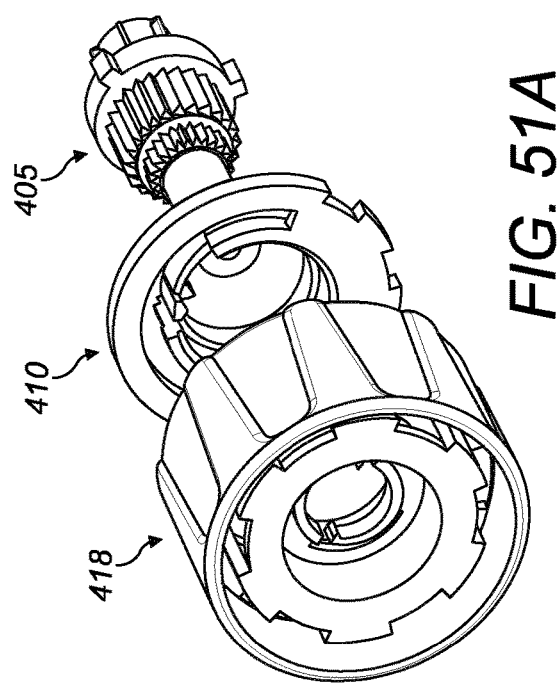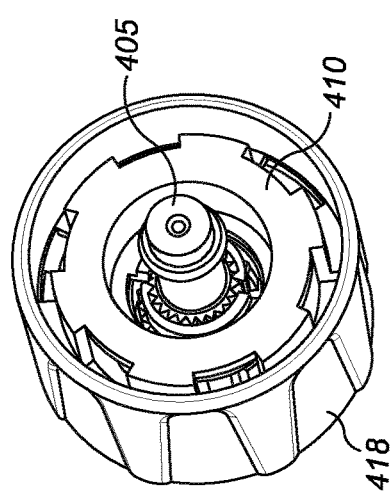

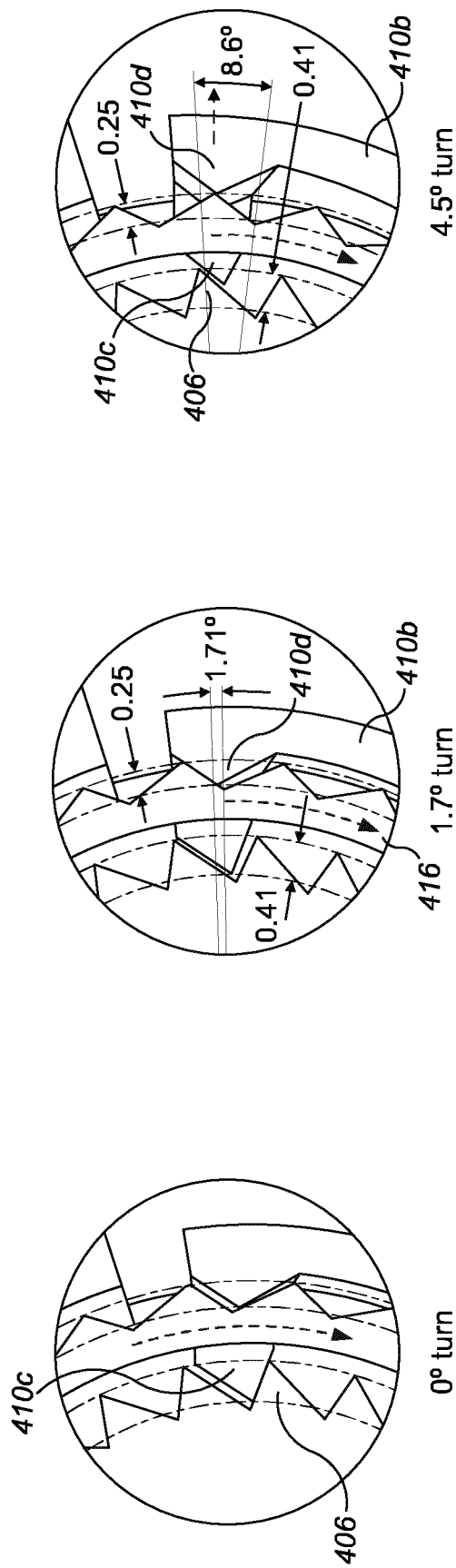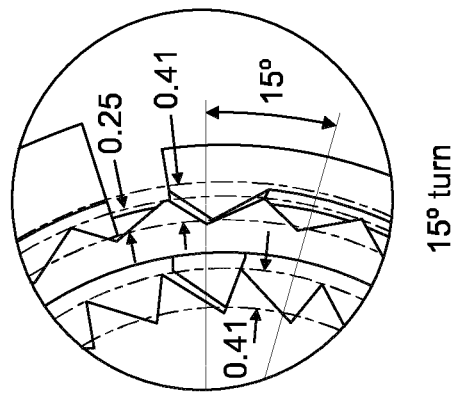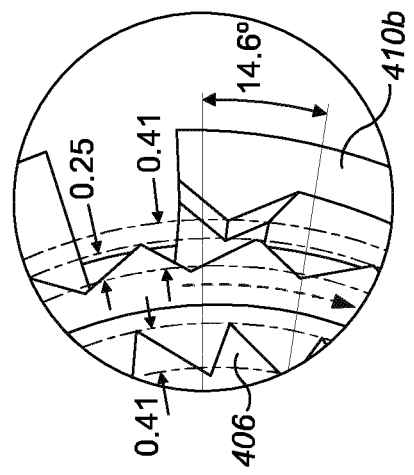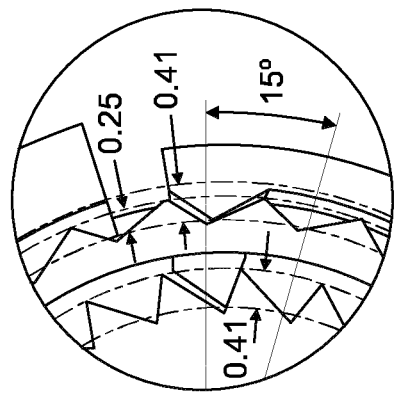

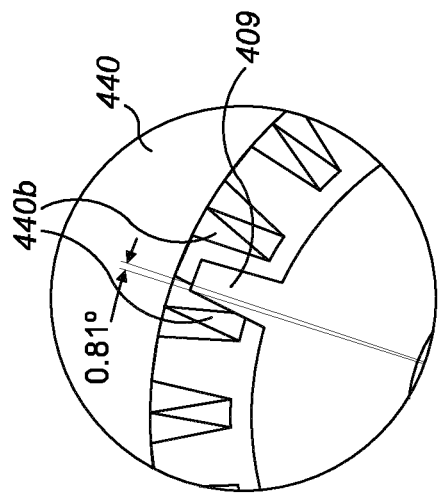
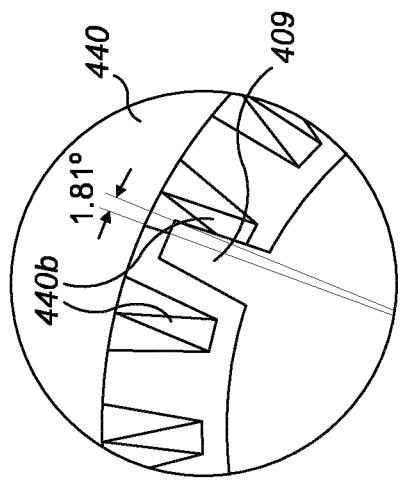
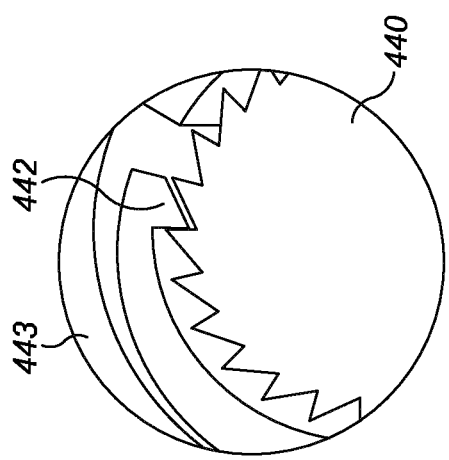
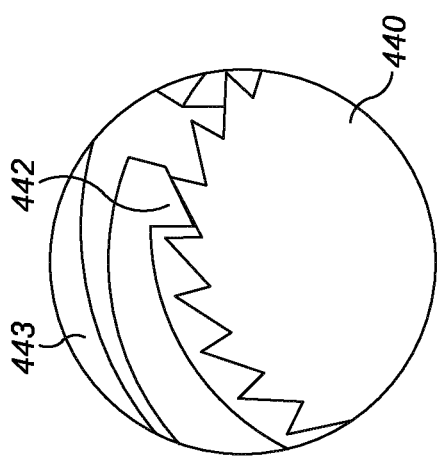
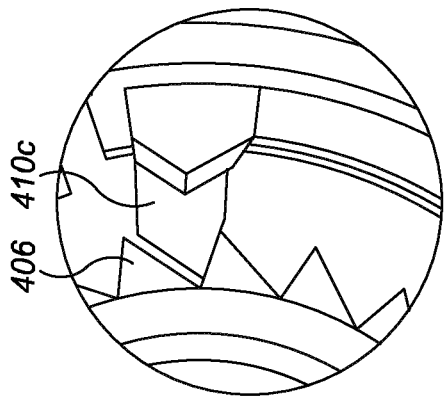
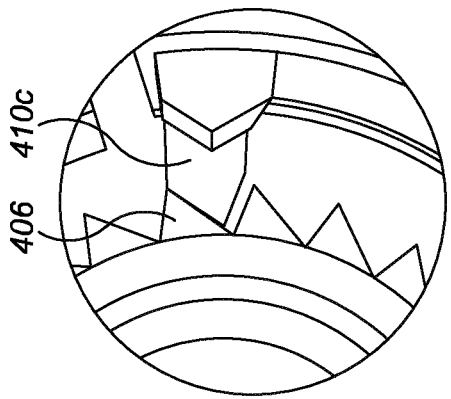
FIG. 79                    FIG. 80

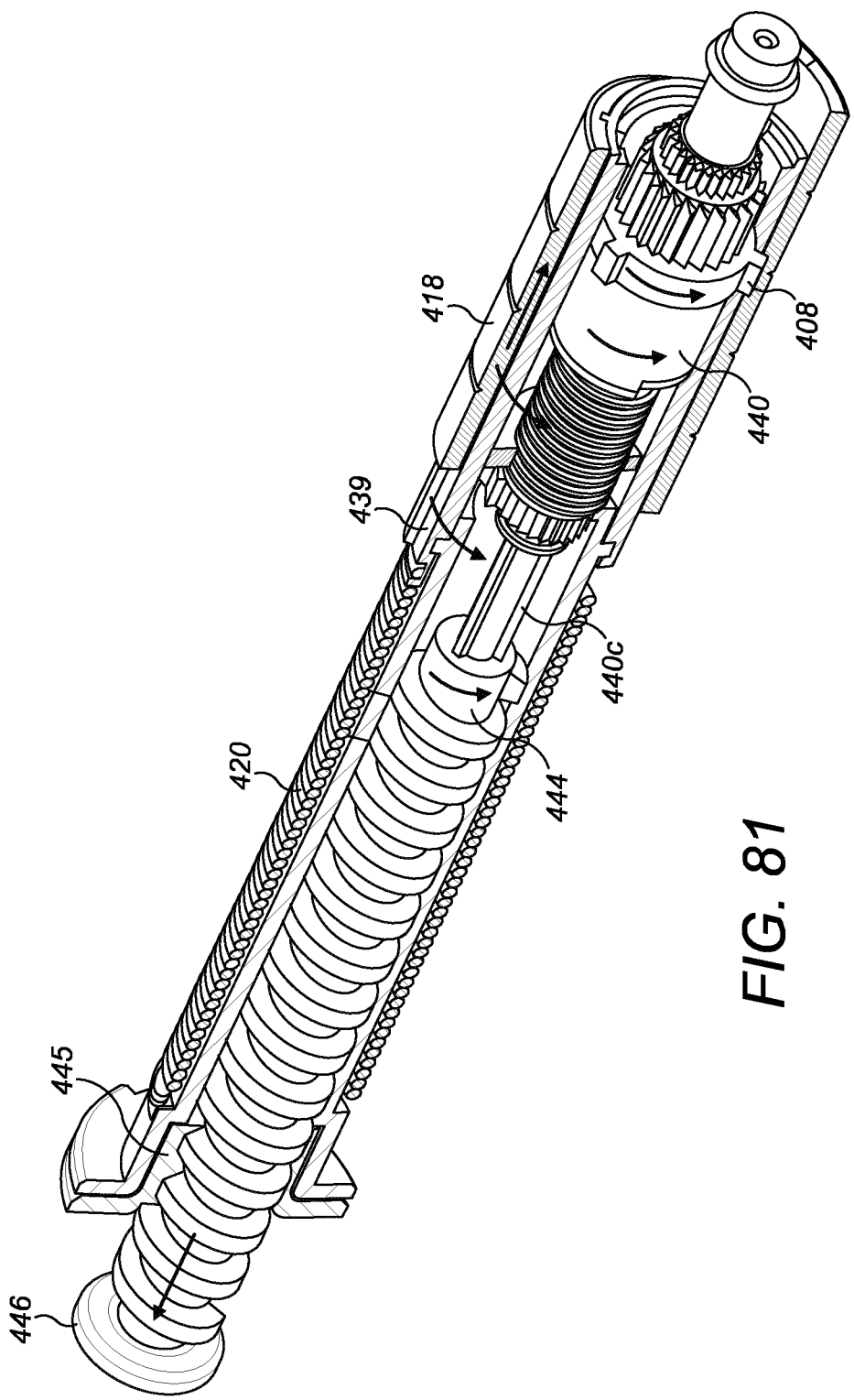

DOSE DELIVERY MECHANISM

CROSS-REFERENCE TO RELATED APPLICATIONS

This application is the National Stage of International Patent Application No. PCT/EP2017/072748, filed Sep. 11, 2017, which claims priority from Great Britain Patent Application No. 1615447.8 filed Sep. 12, 2016, the entire contents of both of which applications are incorporated herein by reference.

This disclosure relates to the field of dose delivery mechanisms for injection devices, preferably to reusable pen-type injection devices.

BACKGROUND

Certain injection devices have a dose setting member, or dose selector, via which the user can select a desired dose of medicament to be delivered from the injection device. The dose selector can commonly be actuated in one direction to increase the set dose ("dialling up") and actuated in another direction to decrease the set dose ("dialling down"). As the dose is dialled up or down, this correspondingly increases or decreases stored energy in the device (e.g. in a torsion spring). An example of this type of dose setting can be seen in WO2006/045528.

In WO2006/045528, a drive member is connected to a dose setting member via a self-tightening "hold ratchet" having saw-toothed teeth. The hold ratchet enables the dose setting member to be rotated in both directions so that a given dose may be set, whilst preventing the spring from unwinding from the currently selected dose. With reference to FIG. 1, during dose setting, a drive member 6 is locked and prevented from rotating by a locking member 4. The locking member 4 is released when it is desired to allow the drive member to deliver a dose of medicament.

Another example of an injection device having a hold ratchet is described in WO2007/063342. A ratchet mechanism is positioned between a drive shaft and a drive element. In the dose setting direction, the ratchet teeth ride over one another to allow rotation of the drive shaft relative to the drive element as a dose knob is turned to set the dose. With reference to FIG. 4, during dose setting, the drive element is held back and prevented from rotating by a toothed rack 11*b* interacting with a correspondingly sized rack 12*a* on a retaining ring 12. These racks 11*b*, 12*a* are unlocked from one another when dose delivery is initiated so that the drive element can rotate in order to deliver the dose.

Another example of an injection device having a hold ratchet is described in WO2015/032780. With reference to FIG. 8, a "second clutch" 119 between a dose selector ("dial member 106") and a drive member 108 serves as a hold ratchet, preventing the spring unwinding. A "first clutch" 118 rotationally couples the drive member and the housing in a coupled state and allows relative rotation between the drive member and the housing in a decoupled state. During dose delivery, the first clutch is in its decoupled state and the second clutch is in its coupled state.

In the above prior art examples, a charged drive mechanism is engaged and ready to deliver medicament but held back until dose delivery is initiated, whereupon the drive mechanism is released so that it can freely rotate and deliver medicament under the force of the energy stored in the device.

BRIEF SUMMARY OF THE DISCLOSURE

In accordance with an aspect of the present invention there is provided an injection device comprising:

a housing having a longitudinal axis;

a dose selector capable of being rotated about said longitudinal axis with respect to said housing by a user to set a dose of medicament to be ejected from the injection device;

a spring capable of storing energy necessary for ejecting the dose of medicament from the injection device, wherein the spring is coupled to the dose selector such that a charging force can be transferred from the dose selector to the spring to increase the energy stored by the spring;

a ratchet arrangement moveable between an engaged state in which the spring is limited from unwinding from a currently selected dose and a disengaged state in which the spring is able to unwind; and a drive assembly including a plunger element capable of providing an axial force for ejecting a dose of medicament from the injection device, wherein the drive assembly further comprises a drive clutch moveable from a disengaged state in which a force path from the spring to the plunger element is interrupted and an engaged state in which the drive assembly can provide the axial force for ejecting a dose of medicament from the injection device via said force path and wherein the drive clutch reaches its fully engaged state before the ratchet arrangement has reached its fully disengaged state.

In this way, the plunger element can be completely isolated from the charged spring until dose delivery is initiated. There is therefore no possibility of unwanted or early delivery of medicament. This is in contrast to prior art devices in which the equivalent of the plunger element is always engaged with the drive mechanism, but held back from delivering medicament until dose delivery is initiated.

In certain embodiments, the ratchet arrangement comprises a radially-flexible ratchet arm and teeth on an internal surface of the housing. The plunger element may comprise a lead screw concentrically arranged within and rotationally fixed with respect to a rotatable drive sleeve.

In an embodiment, the drive assembly includes a drive shaft intermediate said spring and said drive sleeve and said drive clutch comprises splines on said drive sleeve engageable with splines on said drive shaft.

In another embodiment, said drive clutch comprises a drive clutch component having splines on a rear face thereof, the splines being engageable with splines on a front face of said drive sleeve during forward movement of said drive sleeve. Preferably, when the drive clutch is in its disengaged state, the drive clutch component is rotationally fixed with respect to the housing. Forward movement of said drive sleeve may be capable of disengaging said drive clutch component from said housing, allowing relative rotation therebetween.

In another embodiment, the ratchet arrangement comprises a ratchet component rotationally and axially locked with respect to said housing and a drive plate including a first set of splines. The dose selector may include splines for disengaging said ratchet arrangement. Preferably, said ratchet component is capable of interacting with both the splines on the dose selector and the splines on the drive plate. The spring may be fixed at one end to said housing and fixed at the other end to a rotatable drive sleeve. Preferably, the drive assembly further comprises a drive shaft engageable with said drive sleeve to drive the plunger element. The plunger element may comprise a hollow plunger concentrically arranged around said drive shaft. The drive clutch may comprise a further set of splines on said drive plate for engaging splines on said drive shaft and said further set of splines may be on an outer surface of said drive plate with said drive shaft splines on an internal surface thereof.

In certain embodiments, the drive clutch is moveable from the disengaged state to the engaged state before the ratchet arrangement begins to move from the engaged state to the disengaged state.

By having the drive clutch engagement occurring before the ratchet arrangement is fully disengaged, the drive spring is never free to unwind in an uncontrolled manner.

In certain embodiments, the spring is a torsion spring and the charging force transferred to the spring is a charging torque. Preferably, the drive assembly has a rotational to axial coupling, where the drive assembly is rotationally drivable by the torsion spring and is arranged to provide an axial force for ejecting the dose from the injection device.

In certain embodiments, when the drive clutch is in the engaged state, the spring is coupled to the plunger element via one or more intermediate components capable of transmitting the charging force.

The drive assembly is may be concentrically arranged about said longitudinal axis. In certain embodiments, said plunger element may be radially outward of said drive clutch. Alternatively, said plunger element may be radially inward of said drive clutch.

In an embodiment, the injection device may further comprise a medicament container where the medicament container may comprise a pre-filled syringe, or cartridge. The injection device may further comprise a medicament contained in the medicament container. In certain embodiments, the medicament may be selected from the group comprising: antipsychotic substances including risperidone, hormones, antitoxins, substances for the control of pain, immunosuppressives, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

BRIEF DESCRIPTION OF THE DRAWINGS

Embodiments of the invention are further described hereinafter, by way of example only, with reference to the accompanying drawings, in which:

FIG. 1 shows an injection device in accordance with an embodiment of the present invention;

FIG. 2 is a schematic representation of a force path of an injection device according an embodiment of the present invention;

FIGS. 3A-3C show the force path of FIG. 2 at three different stages of operation of the injection device;

FIGS. 13, 13A and 13B illustrate last dose protection;

FIG. 34 is a diagrammatic summary of the key engagement points of the components of the injection device of FIG. 25, at four stages of dose delivery;

FIGS. 51A and 51B are an exploded view and an assembled view of the dose selector, ratchet ring and drive plate, viewed from the rear of the injection device;

FIGS. 52A and 52B are an exploded view and an assembled view of the dose selector, ratchet ring and drive plate, viewed from the front of the injection device;

FIGS. 55A-55E illustrate the dose incrementing stages in more detail;

FIG. 79 shows typical relative positions of the hold ratchet, drive plate, drive shaft and chassis;

FIG. 80 shows the most extreme possible relative positions of the hold ratchet, drive plate, drive shaft and chassis;

FIG. 81 is a perspective view, partly in cross-section, of injection device components involved in dose delivery;

DETAILED DESCRIPTION

Figure 4:
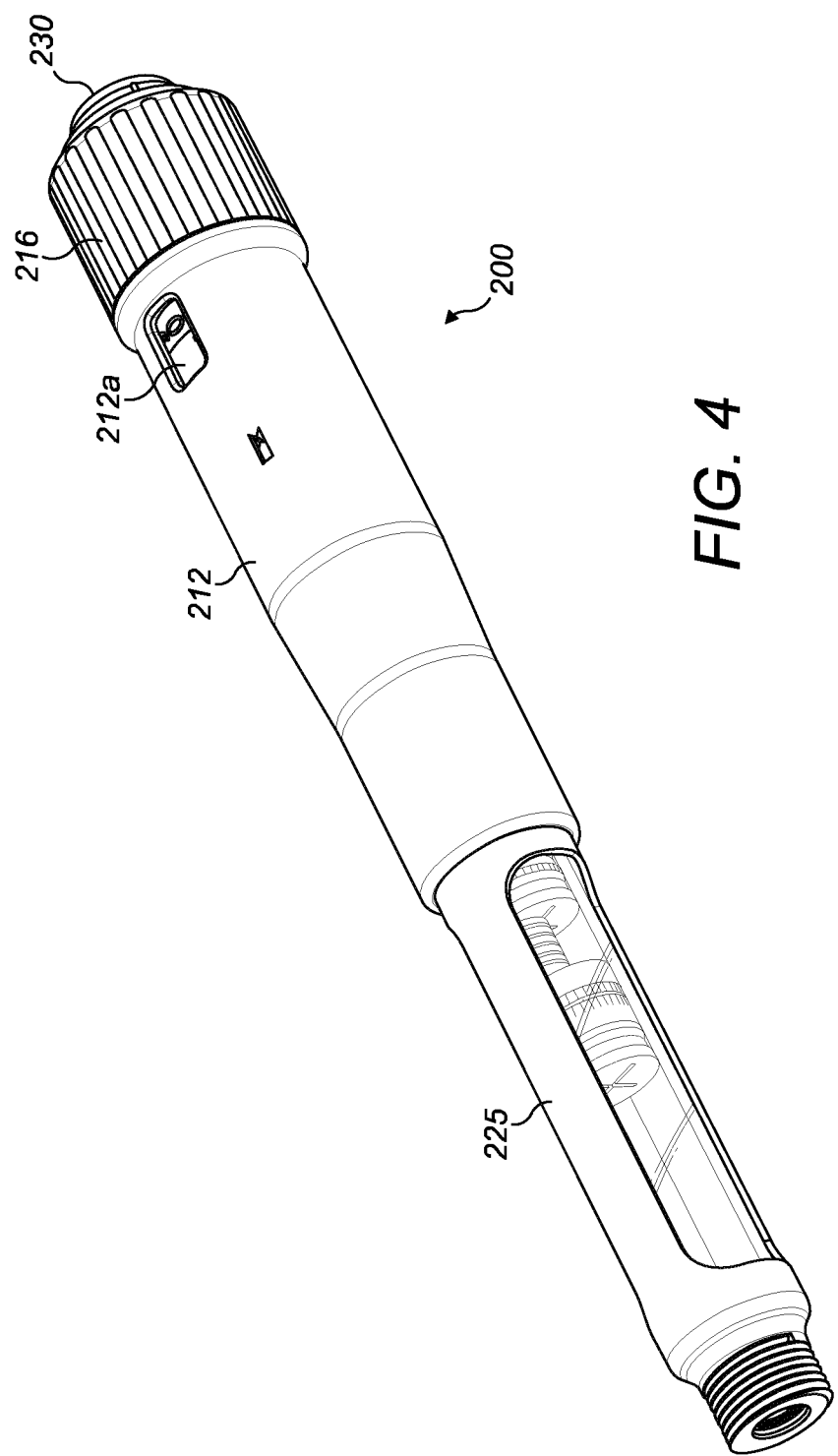
FIG. 4 is a perspective view of another embodiment of the injection device.

In the present disclosure, the following terms may be understood in view of the below explanations:

The term "injection device" may refer to a device intended for the injection of a medicament to the body and includes devices configured for various delivery methods, such as intradermal, subcutaneous, intramuscular, intravenous, intraosseous, intraperitoneal, intrathecal, epidural, intracardiac, intraarticular, intracavernous, and intravitreal, which may include via a cannula, catheter or similar device. Injection device includes syringes of all types, devices that contain said syringes such as auto-injectors, pen-injectors, patch injectors and other similar devices.

The term "pen-injector" may include any device configured to deliver a dose of a medicament from a cartridge.

The term "user" may refer to a medical practitioner, end user or other user associated therewith.

The term "coupling" may refer to a connection between components (not necessarily a direct connection; there may be intermediate components therebetween) that enables a force to be transmitted between the components.

The term "a rotational coupling" may refer to a coupling which enables a rotational force to be transmitted between the components.

The term "operatively connectable" may refer to at least two individual components which are releasably connectable together in such a way that the individual components can work together, for example wherein rotation of one of the individual components effects rotation of all of the operatively connected components.

The term "dose selector" may refer to a component or components which, when actuated by a user, enable a dose of medicament to be selected.

The term "dose indicator" may refer to a component or components which provide a display or indication to the user of the selected dose of medicament.

The term "splines" may refer to one or more ridges, ribs or other protrusions on one component which engage in corresponding grooves or the like on a second component to connect the two components together.

The term "a splined connection" may refer to a connection effected by one or more splines.

The term "forward" or "forwards" may refer to a direction towards the end of the injection device from which medicament is expelled.

The term "backward", "backwards", "rearwards" or "rearwardly" may refer to a direction away from the end of the injection device from which medicament is expelled.

The term "drive assembly" may refer to an assembly of components capable of using a driving force from, for example, a spring, to eject medicament from an injection device.

The term "backlash" may refer to a clearance caused by a gap between mechanical components.

The term "medicament" may include a substance in liquid or gas form. The medicament may be selected from the group comprising of: antipsychotic substances including risperidone, hormones, antitoxins, substances for the control of pain, immunosuppressives, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

When referring to the injection device, the term "containing the medicament" may refer to the medicament being contained within a suitable medicament container, such as a pre-filled syringe or cartridge, within the injection device.

The term "ratchet arrangement" may refer to an arrangement of components comprising a set of splines or teeth and a "ratchet component" which can engage in said splines or teeth to permit one-way movement.

The term "over-torque feature" may refer to a feature located on a first component and capable of interacting with a second component so as to reduce a force being transferred along a force path from the first component to the second component, for example by changing the direction of the force path and/or creating an additional force path.

The term "single component" may refer to one component, an integrally-formed component, a unitary component, or at least two component parts fixed together or with respect to one another.

The term "haptic feedback track" may refer to a plurality of ridges, ribs, teeth, or other protrusions on an internal surface of the injection device and with which another component, moving rotationally with respect thereto, can engage to provide audible and/or tactile feedback to a user of the injection device.

The term "a dose button" may refer to a button or the like at the rear of the injection device which is actuated, for example by pressing axially-forwardly with respect to the device housing, in order to initiate dose delivery.

The term "a force path" may refer to a path between two or more coupled components via which a force can be transmitted between the components. A force path may be "interrupted" if there is a gap between the two or more components, i.e. if they are no longer coupled. Transmission of force between coupled components may be "held back", for example by a ratchet arrangement, but in such a case, the force path is not "interrupted".

The term "a clutch" may refer to a component or feature suitable for operatively connecting two component parts either by a positive fit e.g. with teeth, splines, grooves or the like suitable for engaging and disengaging each other, or by a non-positive (frictional) connection or a combination thereof. Disengaging the clutch may interrupt a force path between two or more coupled components.

Description of First Example Embodiment

An injection device 10 according to an embodiment of the present invention is shown in FIG. 1. The injection device 10 is configured to deliver a dose of medicament and extends along a longitudinal axis L between a front end 10a and a rear end 10b of the injection device 10. The injection device 10 has a housing 12 and a needle 14 projecting from the housing 12 at the front end 10a. A dose selector 16 is provided at the rear end 10b and is arranged to permit the selection of a desired dose of medicament for delivery through the needle 12 into an injection site. The dose selector 16 is capable of being rotated about the longitudinal axis L with respect to the housing 12 by a user to set the desired dose of medicament to be ejected from the injection device. The housing 12 includes an aperture 12a through which a dose indicator 18 is visible.

FIG. 2 shows a schematic representation of a force path 26 within the injection device 10. The internal components include the dose selector 16, a ratchet arrangement 25, a spring 20, a drive assembly 22 and a medicament container 24. The drive assembly 22 includes a drive clutch 21 and a plunger element 23. As described in further detail below, the spring 20 is configured to provide a drive force to the drive assembly 22 such that the drive assembly 22 may act to dispense medicament from the medicament container 24.

The dose selector 16 is coupled to the spring 20 such that a charging force can be transmitted from the dose selector 16 to the spring 20 in order to charge the spring 20. The spring 20 is charged when a force is applied to the spring 20 so as to elastically deform the spring 20, and the resulting elastic energy is stored by the spring 20 (i.e. it is prevented from elastically relaxing during a storage phase). Therefore, charging the spring 20 involves increasing the energy stored by the spring 20.

The spring 20 is coupled to the drive assembly 22 and is arranged to provide a driving force thereto when energy stored by the spring 20 is released. The spring is capable of storing energy necessary for ejecting the dose of medicament from the injection device and the spring is coupled to the dose selector such that a charging force can be transferred from the dose selector to the spring to increase the energy stored by the spring.

The drive assembly 22 acts to expel medicament from the medicament container 24 using the plunger element 23 which is capable of providing an axial force for ejecting a dose of medicament from the container 24. In certain embodiments, the medicament container 24 may be a pre-filled syringe or cartridge having a barrel and a stopper moveable in the barrel. In such embodiments, the plunger element 23 may act to move the stopper so as to expel medicament through an opening in the barrel. In certain embodiments of the invention, the medicament cartridge may or may not be connected to a needle.

The drive assembly 22 includes a drive clutch 21 which determines whether force from the spring 20 can reach the plunger element 23 or not. The drive clutch 21 is moveable from a disengaged state in which a force path 26 from the spring 20 to the plunger element 23 is interrupted and an engaged state in which the drive assembly 22 can provide the axial force for ejecting a dose of medicament from the injection device via said force path 26.

In embodiments where the spring 20 is a torsion spring, the spring 20 is charged by applying a torque to wind the spring 20 and elastic energy may be stored by the spring 20 and subsequently released as torque.

In embodiments where the spring 20 is a compression spring, the spring 20 may be charged by applying an axial force to compress the spring 20 and elastic energy may be stored by the spring 20 and subsequently released as an axial force.

In certain embodiments, the force path 26 may include one or more torque paths and/or one or more axial force paths, where one or more rotational to axial couplings are employed to switch between rotational and axial forces along the force path 26. Indeed, in certain embodiments, one or more intermediate components may be provided between any of the components shown in FIG. 2.

FIGS. 3A-3C show the force path 26 of FIG. 2 at three different stages of operation of the injection device. The ratchet arrangement 25 comprises a ratchet component and an internal surface of the housing 12 (not shown). FIG. 3A shows the ratchet arrangement 25 in its engaged state (indicated by a box having a solid outline). When the ratchet arrangement 25 is in its engaged state, as the user turns the dose selector 16, a charging force can be transmitted from the dose selector 16 to the spring 20 in order to charge the spring 20. The ratchet component is engaged with an internal surface of the housing, preventing relative rotation therebetween in the unwinding direction. Therefore, when the ratchet arrangement 25 is in in the engaged state, the spring 20 is limited from unwinding from a currently selected dose.

As shown in FIG. 3A, when the ratchet arrangement 25 is fully engaged, allowing the spring 20 to be charged, the force path 26 is interrupted by the drive clutch 21 between the spring 20 and the plunger element 23, the drive clutch 21 being in a fully disengaged state (indicated by a box having a dotted outline). Therefore, during dose setting, force cannot be transmitted from the spring 20 to the plunger element 23, preventing early or unwanted delivery of medicament from the container 24.

When the dose has been set, the user can initiate dose delivery, for example by pressing a dose button (not shown). FIG. 3B represents the condition soon after dose delivery has been initiated. In this condition, the ratchet arrangement 25 begins to move from the engaged state to a disengaged state in which the spring 20 is able to unwind. FIG. 3B shows the ratchet arrangement 25 now only partially engaged (indicated by a box having a dashed outline). At the same time as the ratchet arrangement 25 is moving from its engaged state to its disengaged state, the drive clutch 21 begins to move from its disengaged state to an engaged state in which force from the spring 20 can be transmitted to the plunger element 23. FIG. 3B shows the drive clutch 21 partially engaged (indicated by a box having a dashed outline).

After continued pressing of the dose button, the condition represented in FIG. 3C is reached. In this condition, the ratchet arrangement 25 is fully disengaged (indicated by a box having a dotted outline) and the spring 20 is able to unwind freely. The drive clutch 21 is fully engaged (indicated by a box having a solid outline) and the drive assembly 22 (in this case, the plunger element 23 thereof) can provide the axial force for ejecting a dose of medicament from the injection device via the force path 26.

In summary, the force path 26 from the spring 20 to the plunger element 23 is interrupted in FIG. 3A, when the ratchet arrangement 25 is engaged and the drive clutch 21 is disengaged. The ratchet arrangement 25 is disengaged and the drive clutch 21 is engaged in FIG. 3C, wherein the drive assembly 22 can provide the axial force for ejecting a dose of medicament from the injection device via said force path 26.

Description of Second Example Embodiment

A further, non-limiting, embodiment of an injection device according to the present invention is illustrated in FIGS. 4-24.

Referring to FIGS. 4-8, the injection device 200 includes a housing 212, a dose selector 216, a dose button 230 and dose button spring 231, a units wheel 218, a tens wheel 219, a ratchet pawl 217, a housing top cap 221, an odometer shuttle lock 222, a drive spring 220, a drive sleeve 240, a last dose nut 241, a drive clutch 250, a drive clutch spring 251, a leadscrew nut 252, a leadscrew 253 and a thrust bearing 254, all located concentrically about a common longitudinal axis L. The axis L extends between a front end 200a and a rear end 200b of the injection device 200.

The injection device 200 has a medicament cartridge 224 supported in a cartridge holder 225 at the front end 200a of the injection device. A needle or needle hub unit (not shown) can be connected to the cartridge holder. The cartridge is sealed by an axially-moveable cartridge stopper 226 at its rear end.

The dose button 230 is biased rearwardly by the effect of the dose button spring 231 between the housing 212 and front end of the drive sleeve 240 with which the dose button 230 is axially engaged. The dose selector 216 is provided at the rear end 200b of the injection device 200 and is arranged to permit the selection of a desired dose of medicament for delivery from the medicament cartridge 224 into an injection site. The dose selector 216 is axially constrained with respect to the housing 212 but is rotatable with respect thereto, about axis L. The dose selector 216 is used to set the dose by increasing the rotational preload of the drive spring 220 which is prevented from unwinding by the ratchet pawl 217 which engages between the housing 212 and the units wheel 218.

Figure 5:
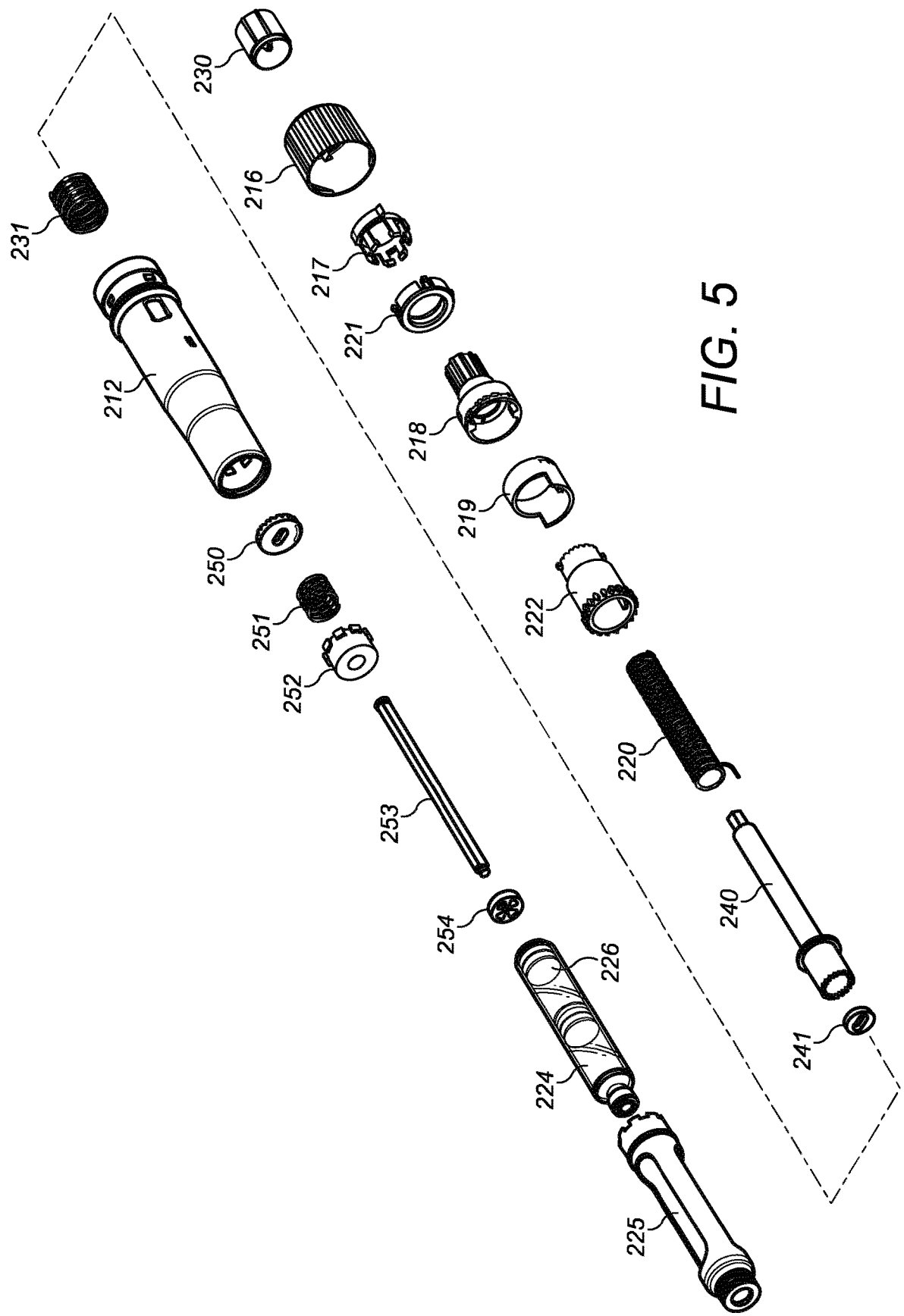
FIG. 5 is an exploded view of the injection device of FIG. 4.
Figure 5A:
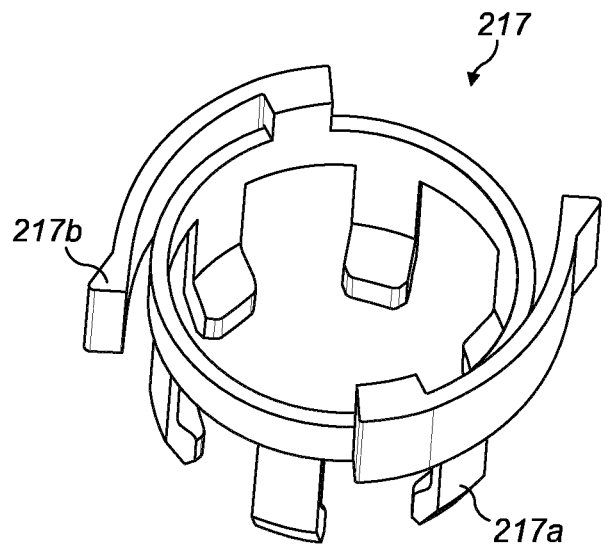
FIG. 5A is a perspective view of the ratchet pawl, drawn to a larger scale.
Figure 9:
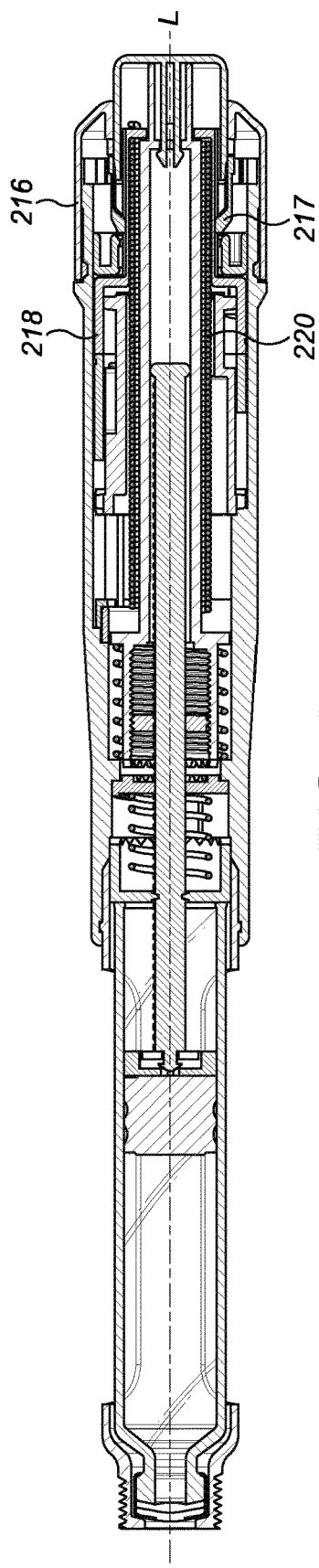
FIGS. 9 and 9A-9C illustrate incrementing the dose.
Figure 9C:
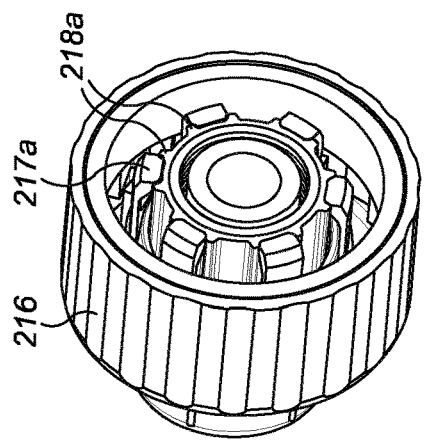
Figure 9B:
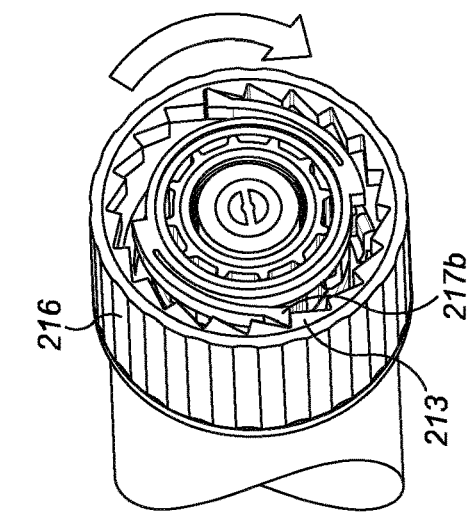

The ratchet pawl 217 (best seen in FIG. 5A) includes a plurality of ratchet fingers 217a which, in the assembled injection device 200, extend generally axially rearwardly to engage with the units wheel 218 as shown in FIG. 9C. The ratchet pawl 217 also includes ratchet arms 217b which, in the assembled injection device 200, engage with teeth 213 on the inside surface of the housing 212 to prevent unwinding of the drive spring 220, as shown in FIG. 9B, while the dose is being incremented.

A dose indicator is disposed within the housing 212 and displays reference indicia, such as numbers or symbols, to indicate the level of dose selected by the dose selector 216. The housing 212 includes an aperture 212a through which the dose indicator is visible. The dose indicator comprises the units wheel 218 for displaying units and the tens wheel 219 for displaying tens and the odometer shuttle lock 222. The units wheel 218 is intermittently coupled to the odometer shuttle lock 222 which is always rotationally coupled to the tens wheel 219. The tens wheel 219 has maximum and minimum dose limit features in the form of rotational endstops 271, 272 respectively, which can engage a limiting rib 290 in the housing 212 to keep the selected dose within the range defined by the maximum and minimum doses. This max/min dose limiting will be described in more detail later.

With reference to FIGS. 14-18, the dose indicator is an odometer comprising a units wheel 218, a tens wheel 219 and an odometer shuttle lock 222. The units wheel 218 has units numbers 260 around the circumference thereof, comprising two consecutive series of the numbers 0-9. Two drive dogs 261 are located 180 degrees apart on the internal surface of the forward end of the units wheel 218 and two engagement splines 262 are also located 180 degrees apart from one another. The sets of drive dogs 261 and engagement splines 262 may be rotationally offset from one another by approximately 90 degrees. In an alternative embodiment the units wheel 218 may comprise one consecutive series of the numbers 0-9 around its circumferential surface, and one drive dog 261. The units wheel 218 may comprise one or more than two engagement splines 262, the engagement splines 262 rotationally arranged to be engageable with the shuttle lock rear teeth 283. The drive dogs 261 have angled faces which, when engaging corresponding angled faces 282 on the shuttle lock 222, cause a camming action that can move the shuttle lock 222 axially.

Tens wheel 219 has tens numbers 270 around the circumference thereof, comprising a series of the numbers 0-10. The forward end of the tens wheel 219 includes maximum and minimum dose limit features 271, 272, in the form of rotary endstops which can each engage a max/min limit rib 290 on the internal surface of the housing 212. The internal surface of the tens wheel 219 includes a key 273 for engaging with the shuttle lock 222.

The shuttle lock 222 is a generally cylindrical component having a forward section of largest diameter with double-ended peripheral teeth 280 at the forward end thereof having angled faces which can alternately engage dogs 291 and engagement ribs 292 on the interior of the housing 212. The angled faces cause a camming action that can move the shuttle lock 222 axially.

In general terms, the function of the housing dogs 291, housing engagement ribs 292 and units wheel drive dogs 261 is to enable the shuttle lock 222 to move alternately between two axial positions, as will be explained in more detail later.

An axially-extending keyway 281 is provided for engaging the key 273 on the tens wheel 219 in order to rotationally lock the tens wheel 219 and shuttle lock 222 together whilst permitting axial movement therebetween. In alternative embodiments, the key may be provided on the shuttle lock 222 and the axially-extending keyway may be provided on the tens wheel 219.

The rear section of the shuttle lock 222 is of smaller diameter and includes dogs 282 at the rear end thereof, located 180 degrees apart from one another which can engage with the drive dogs 261 of the units wheel 218.

The rear surface of the shuttle lock 222 is provided with a series of axially-extending shuttle lock rear teeth 283. The number of teeth 283 corresponds with the number of units of medicament available per rotation of the units wheel 218 (in this case 20). Depending upon the relative axial positions of the units wheel 218 and the shuttle lock 222, the engagement splines 262 on the units wheel 218 can either be engaged with the shuttle lock rear teeth 283, or not engaged with the shuttle lock rear teeth 283.

Figure 18:
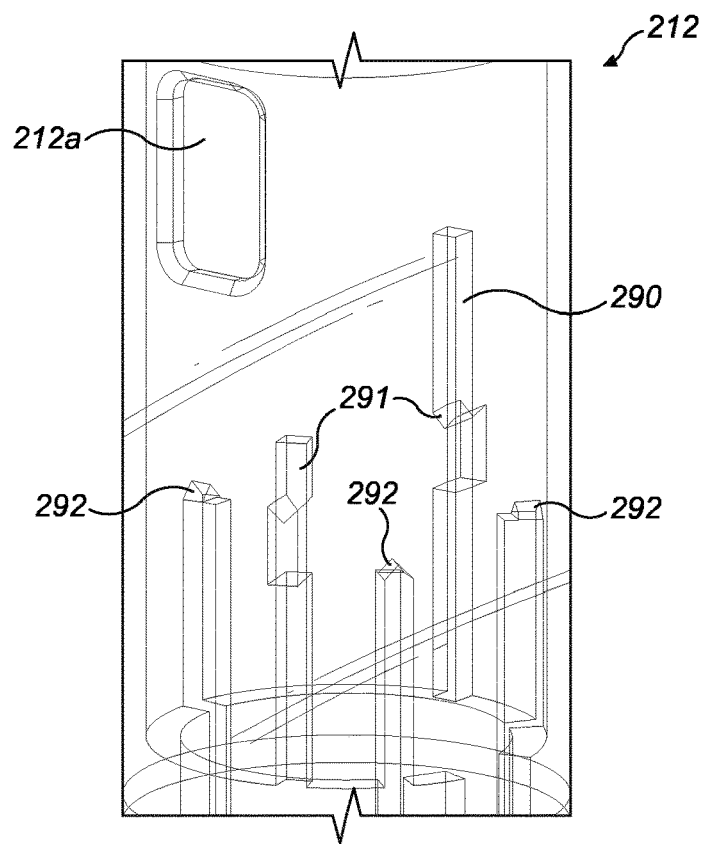
FIG. 18 is a perspective view of housing features relevant to the odometer mechanism.

FIG. 18 shows the portion of the internal surface of the housing 212 which interacts with the odometer mechanism. The aperture 212a through which the dose is displayed can be seen. The illustrated portion of the housing includes an internally-projecting max/min limit rib 290, two dogs 291 for engaging the shuttle lock 222 and three engagement ribs 292 for engaging the shuttle lock 222. FIG. 18 is shown partly in cross-section; the pointed ends of dogs 291 are at the same axial position and are located 180 degrees apart on the internal surface of the housing 212 (half of the housing 212 has been removed from FIG. 18).

As illustrated in FIG. 18, one of the dogs 291 for engaging the shuttle lock 222 may be located at one end of the max/min limit rib 290 such that both functions can be performed by the same component on the internal surface of the housing 212.

The drive spring 220 is a torsion spring which is fixed at one end with respect to the housing 212 and engaged at its other end to the units wheel 218.

Figure 5B:
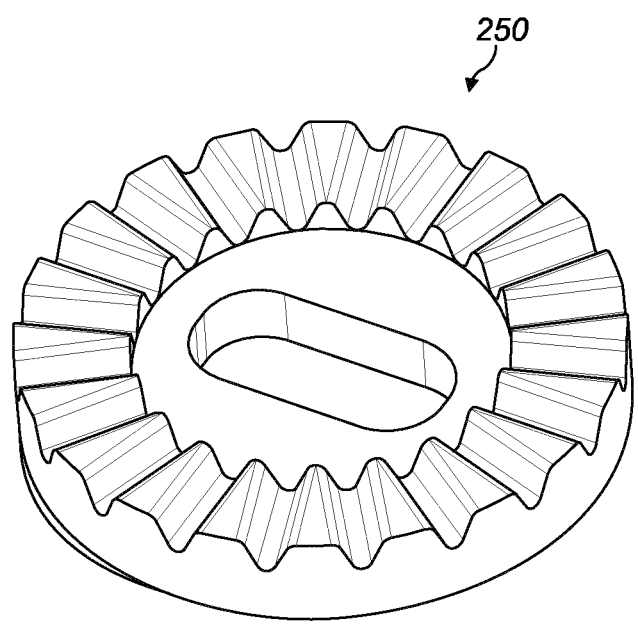
FIG. 5B is a perspective view of the drive clutch, drawn to a larger scale.
Figure 6:
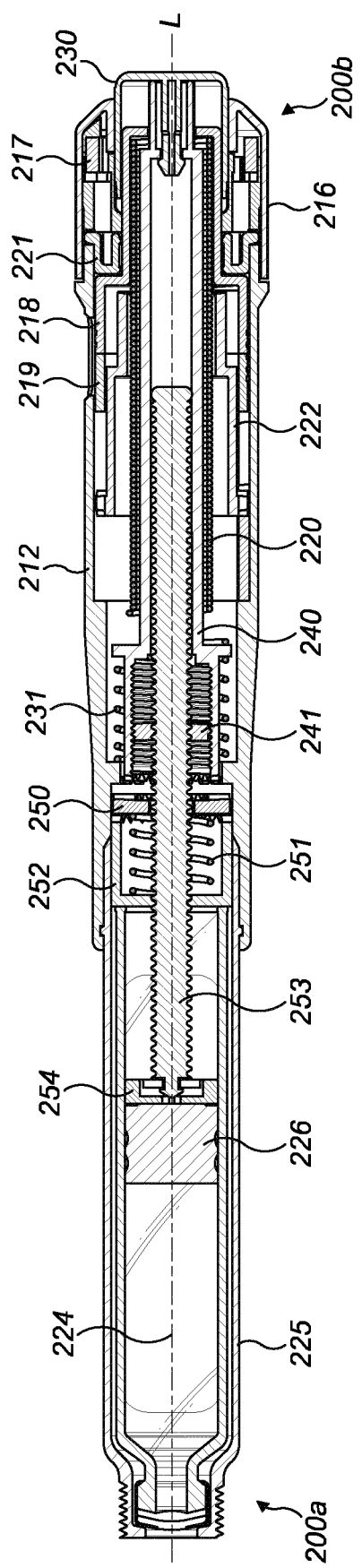
FIG. 6 is a cross-sectional view of the injection device of FIG. 4.
Figure 7:
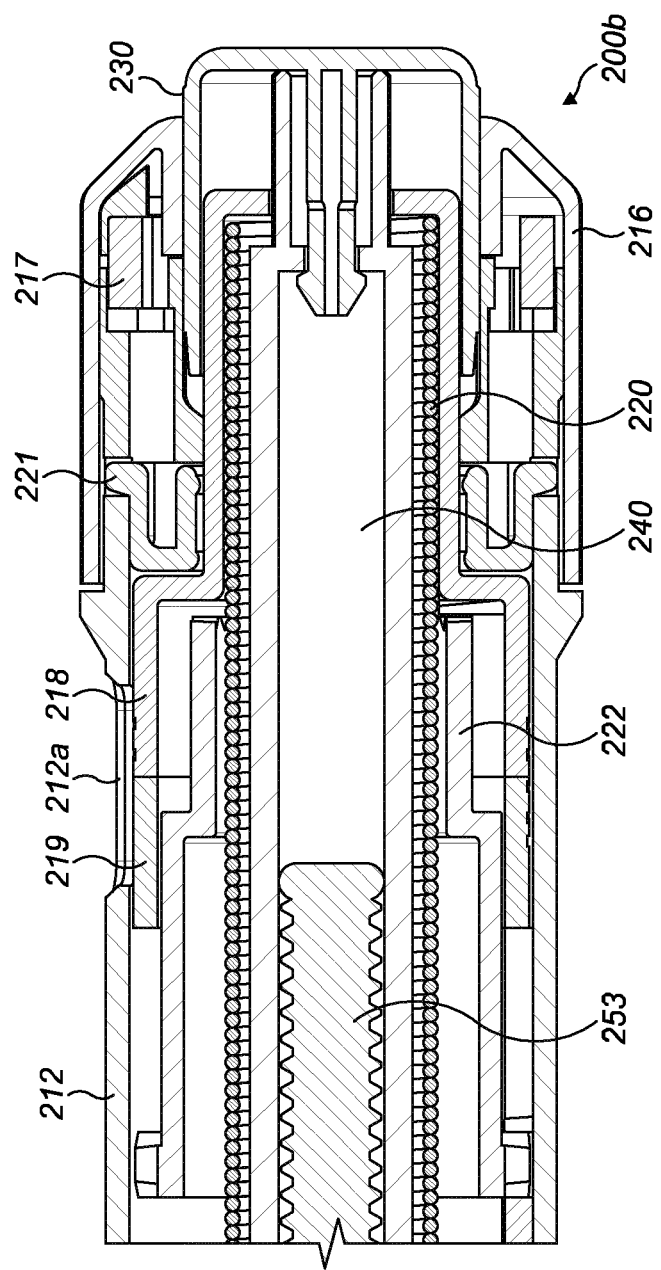
FIG. 7 is a cross-sectional view, drawn to a larger scale, of the rear end of the injection device of FIG. 4.
Figure 8:
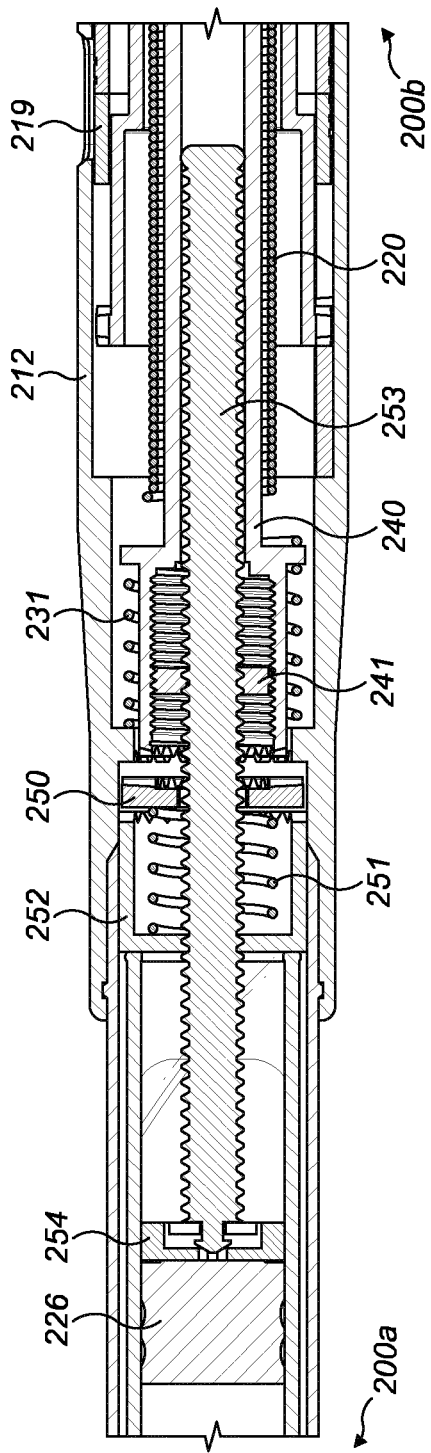
FIG. 8 is a cross-sectional view, drawn to a larger scale, of the central portion of the injection device of FIG. 4.

The drive clutch 250, best seen in FIG. 5B, is generally circular with formations (uppermost in FIG. 5B) which, in the assembled injection device 200, extend in a direction towards the rear of the device. The drive clutch spring 251 biases the medicament cartridge 224. The housing 212 is provided with forward-facing clutch engaging features 215 which, in the position shown in FIG. 9, engage the clutch 250 so that they are rotationally locked together. The clutch 250 can be disengaged from the clutch engaging features of the housing 215 by forward axial movement of the clutch 250, caused by forward movement of the drive sleeve 240. A haptic feedback arm 250a is provided on the front face of the drive clutch 250 (the underside in FIG. 5B).

The operation of the respective features of the injection device 200 will now be described in more detail below.

When the dose button 230 is depressed, firstly the drive clutch 250 is decoupled from the housing 212 and coupled to the drive sleeve 240. Secondly, the ratchet pawl 217 is decoupled from the units wheel 218. Decoupling of the ratchet pawl 217 from the units wheel 218 allows the drive spring 220 to rotate the units wheel 218 and drive sleeve 240, which are rotationally coupled together, about the longitudinal axis L.

Rotation of the drive sleeve 240 causes the drive clutch 250 to rotate which, in turn, rotates the leadscrew 253 to which the drive clutch 250 is splined.

Rotation of the leadscrew 253 causes it to advance axially forwards towards the front end 200a of the injection device 200 because of the engagement of the leadscrew thread with the thread of the leadscrew nut 252. The leadscrew nut 252 is rotationally and axially fixed with respect to the housing 212.

During dose setting, the last dose nut 241 is rotationally fixed with respect to the housing 212 via the leadscrew 253. The last dose nut 241 can translate axially up and down the thread inside the drive sleeve 240 due to rotation of the drive sleeve 240 when the dose is being set. Translation of the last dose nut 241 inside the drive sleeve 240 is limited by a rotational stop feature on the drive sleeve 240 which limits the travel of the last dose nut 241 to a position corresponding with the maximum dispense volume of the injection device 200.

During dose delivery, the drive sleeve 240, leadscrew 253 and last dose nut 241 all rotate together and there is no axial translation of the last dose nut 241 with respect to the drive sleeve 240.

Dose Setting—Incrementing the Dose

With the injection device 200 in the configuration shown in FIG. 9, the user grips the dose selector 216 and rotates it clockwise about axis L, with respect to the housing 212, in order to increment the dose and charge the drive spring 220.

Figure 9A:
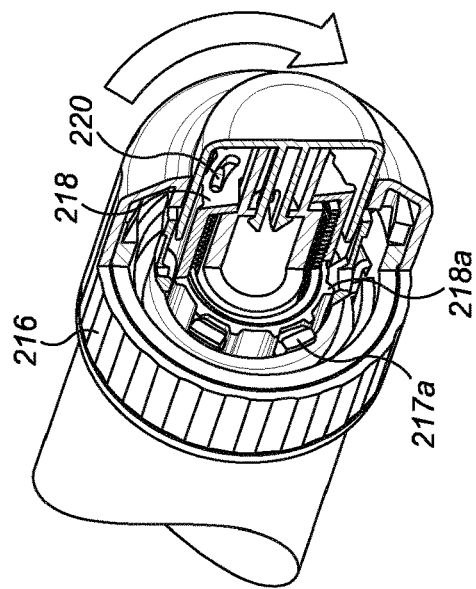

As the dose selector 216 is turned clockwise, the dose selector 216 is engaged with the ratchet pawl 217, causing it to rotate with the dose selector 216. The ratchet pawl 217 drives the units wheel 218 clockwise because of ratchet fingers 217a engaging ribs 218a of the units wheel 218, as shown in FIG. 9A. The drive spring 220 is hooked into the back of the units wheel 218 and is therefore tightened as the units wheel 218 is rotated. In other words, torque is transferred from the dose selector 216 to the drive spring 220 directly through the dose indicator, i.e. the units wheel 218.

While the dose is being incremented, the ratchet arms 217b on the ratchet pawl 217 engage with teeth 213 on the inside surface of the housing 212 to prevent un-winding of the drive spring 220, as shown in FIG. 9B.

When the dose selector 216 reaches a maximum, minimum or last dose limit, the ratchet fingers 217a flex radially outwardly and skip past the ribs 218a of the units wheel 218 (FIG. 9C).

Dose Setting—Decrementing the Dose

Figure 10:
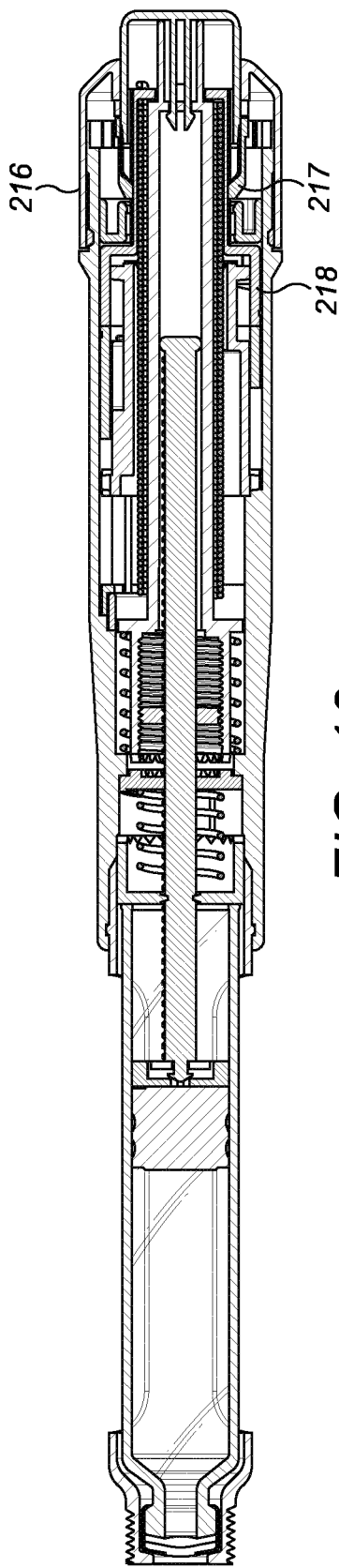
FIGS. 10, 10A and 10B illustrate decrementing the dose.
Figure 10B:
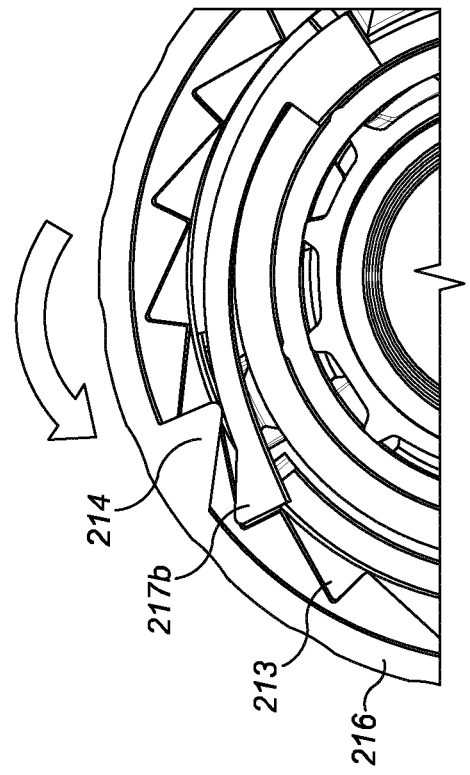
Figure 10A:
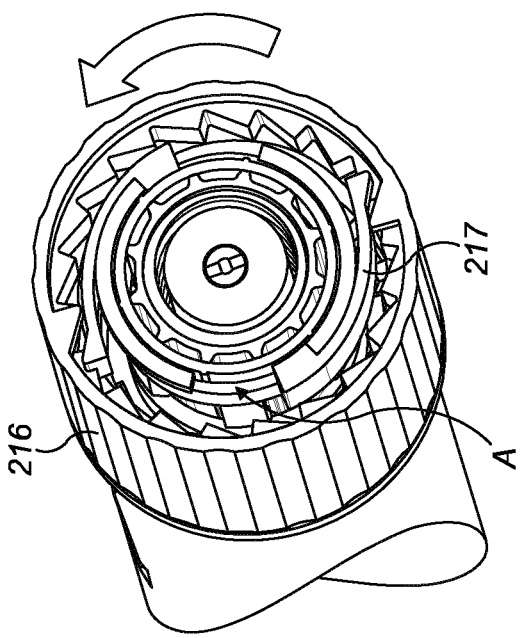

When it is desired to decrement the selected dose, the dose selector 216 is turned anti-clockwise. As shown in FIG. 10A, as the dose selector 216 is turned anti-clockwise, there is a small amount of backlash at point A such that the dose selector 216 can rotate slightly with respect to the ratchet pawl 217. This small relative movement is sufficient to allow tabs 214 on the dose selector 216 to depress the ratchet arms 217b so that they can click past the housing teeth 213, allowing the drive spring to unwind slightly before the ratchet arms 217b catch again on the next housing tooth 213. The tabs 214 may be tooth-shaped formations projecting radially-inwardly from an internal surface of the dose selector 216. This is represented in FIG. 10B. Each decrement preferably equates to 1 IU ("international unit") of medicament.

Dose Delivery

Figure 11:
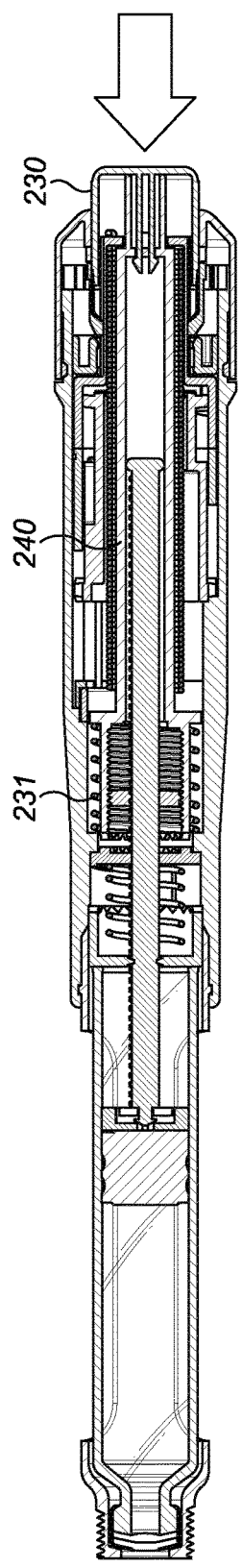
FIGS. 11 and 11A-11F illustrate dose delivery.
Figure 11C:
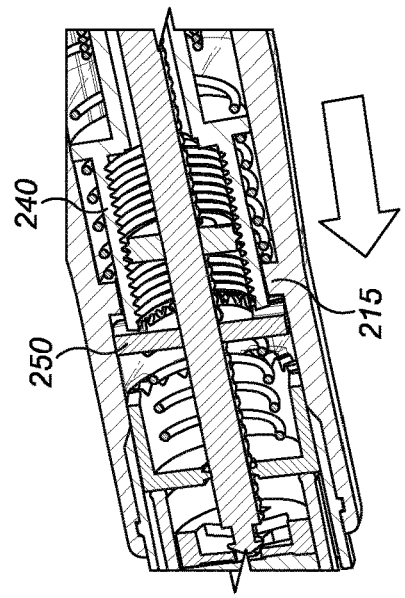
Figure 11B:
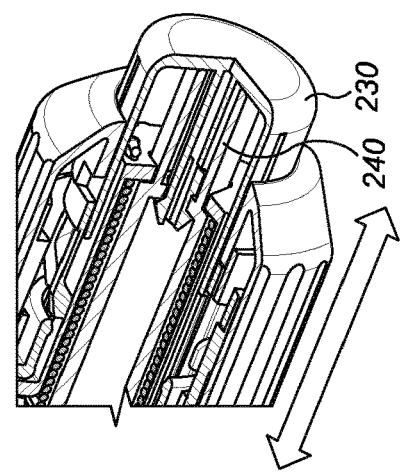
Figure 11A:
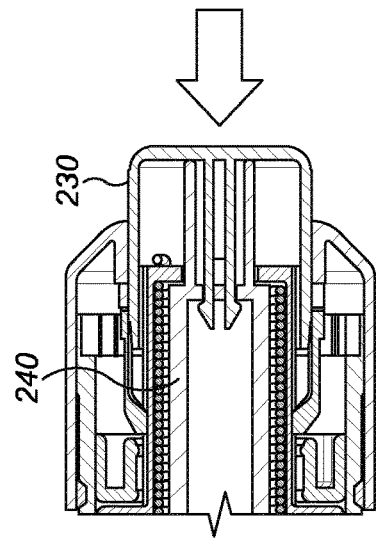

To initiate dose delivery, the user presses the dose button 230 against the bias of the dose button spring 231 as shown in FIG. 11. This pushes the drive sleeve 240 axially forwards. Although the drive sleeve 240 is rotationally locked to the units wheel 218, it is free to slide axially with respect thereto (FIG. 11B).

Figure 11D:
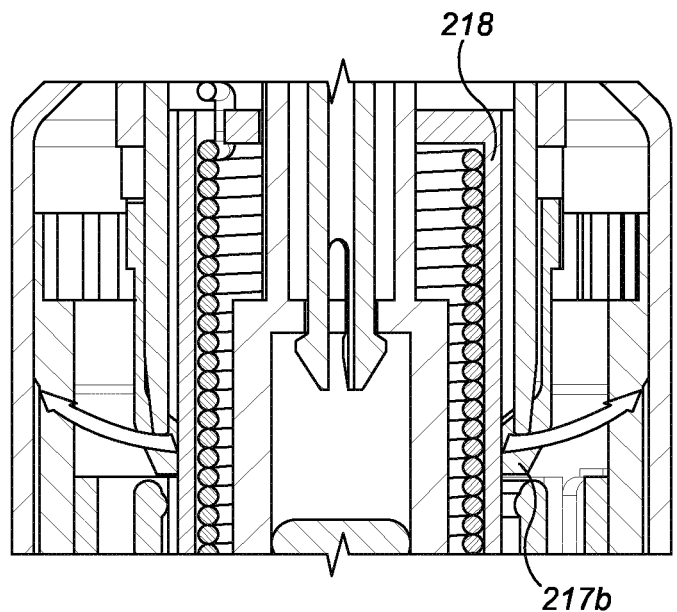
Figure 11E:
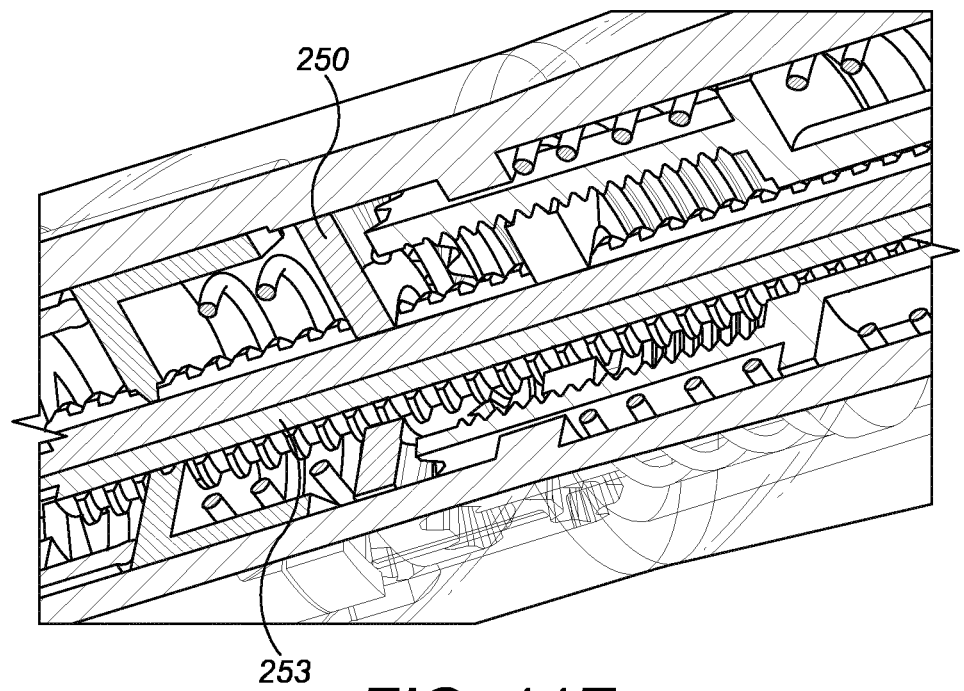

As the drive sleeve 240 advances, its forward end engages the rear surface of the drive clutch 250. The drive clutch 250 disengages from the clutch engaging features 215 on the inside surface of the housing 212 (FIG. 11O). Once the drive clutch 250 is fully engaged with the drive sleeve 240, the dose button 230 disengages the ratchet pawl 217 from the units wheel 218 (FIG. 11D). The units wheel 218 is now free to rotate the drive sleeve 240 and therefore also the drive clutch 250 about longitudinal axis L. The drive clutch 250 is splined to the leadscrew 253 (FIG. 11E).

Figure 11F:
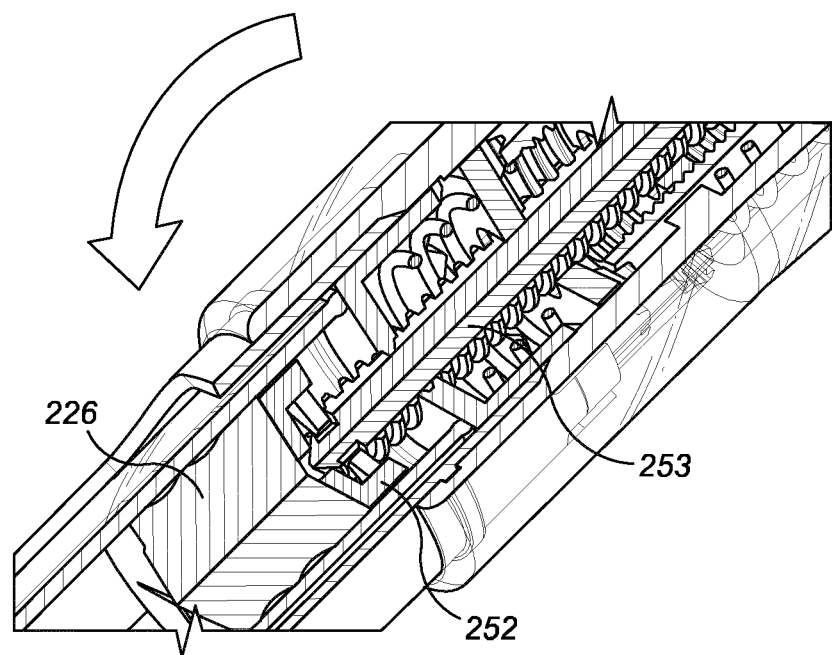

Therefore the leadscrew 253 now rotates and is caused to advance axially due to threaded engagement with the leadscrew nut 252. The thrust bearing 254 advances the cartridge stopper 226 into the cartridge, in order to expel medicament to deliver the selected dose (FIG. 11F).

When the dose button 230 is released, the dose button spring 231 returns the dose button 230 and drive sleeve 240 to their original starting positions. This axially rearward movement disengages the drive clutch 250 and re-engages the ratchet arms 217b with the housing 212 thereby stopping dose delivery.

Dose Delivery—Haptic Feedback

Figure 12:
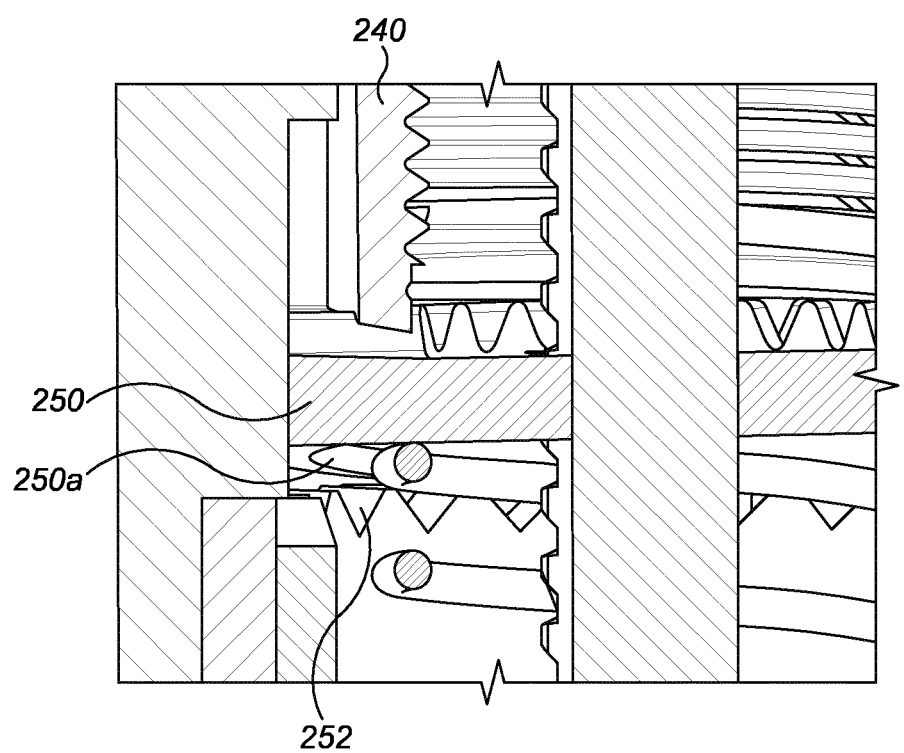
FIG. 12 illustrates a haptic feedback feature.
Figure 14:
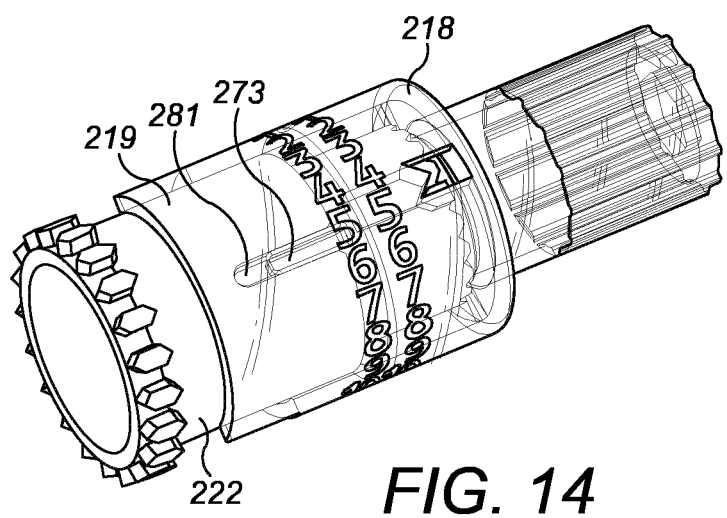
FIG. 14 is a perspective view of the odometer mechanism.
Figure 15:
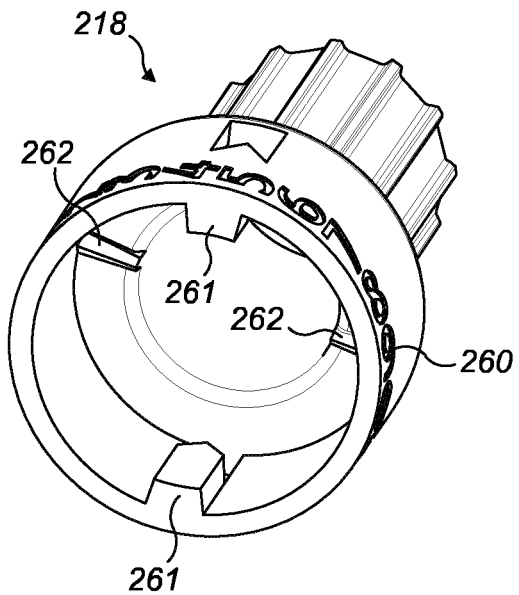
FIG. 15 is a perspective view of the units wheel from the odometer mechanism.
Figure 16:
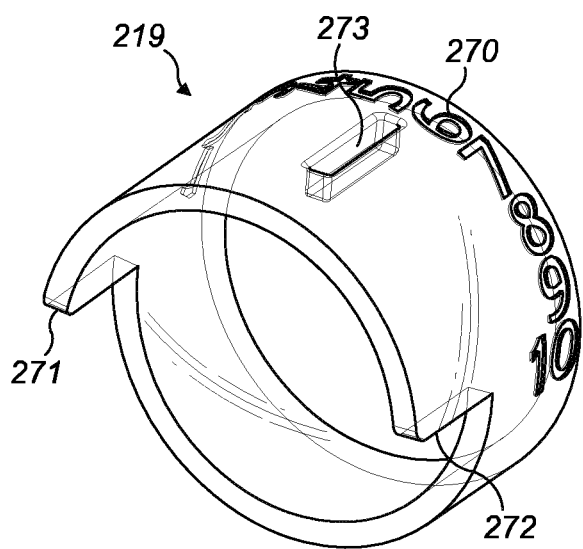
FIG. 16 is a perspective view of the tens wheel from the odometer mechanism.

Referring to FIG. 12, during dose delivery haptic feedback occurs between the drive clutch 250 and the leadscrew nut 252 when the drive clutch 250 is spinning, by virtue of the haptic feedback arm 250a on the drive clutch clicking over axially-rearwardly-facing teeth on the leadscrew nut 252.

Last Dose Protection

When the medicament cartridge 224 is relatively empty, after several doses have already been delivered therefrom, it is undesirable for the user to be able to select a dose that is larger than the available quantity of medicament remaining. Last dose protection is provided to deal with this situation. Last dose protection is provided by the last dose nut 241.

As shown in FIG. 13A, the last dose nut 241 moves axially forwards and backwards on the thread inside the drive sleeve 240 during dose incrementing and decrementing. When there is less than a predetermined amount (e.g. 100 IU) of medicament remaining in the cartridge 224, the last dose nut 241 stops against a rotary endstop 240a at the rear of the drive sleeve thread.

Engagement of the last dose nut 241 with the endstop 240a means that, should the user attempt to wind the dose selector 216 beyond the remaining dose, the over-torque protection is actuated, preventing the user from damaging the device (FIG. 13B). The ratchet fingers 217a disengage from the units wheel 218 as previously described in relation to FIG. 9C.

Dose Display

Figure 19A:
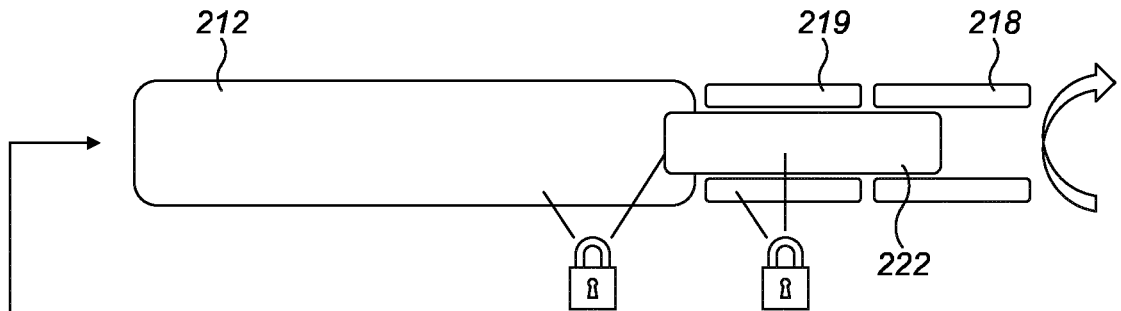
FIGS. 19A-19C show three stages of the odometer mechanism's operation.
Figure 19B:
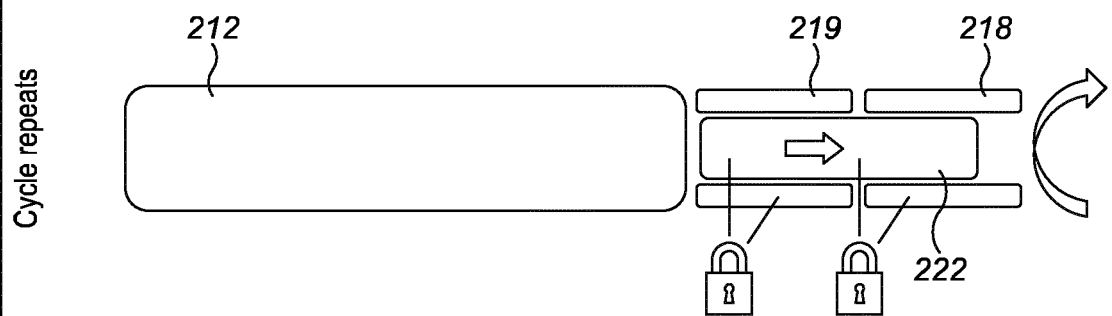
Figure 19C:
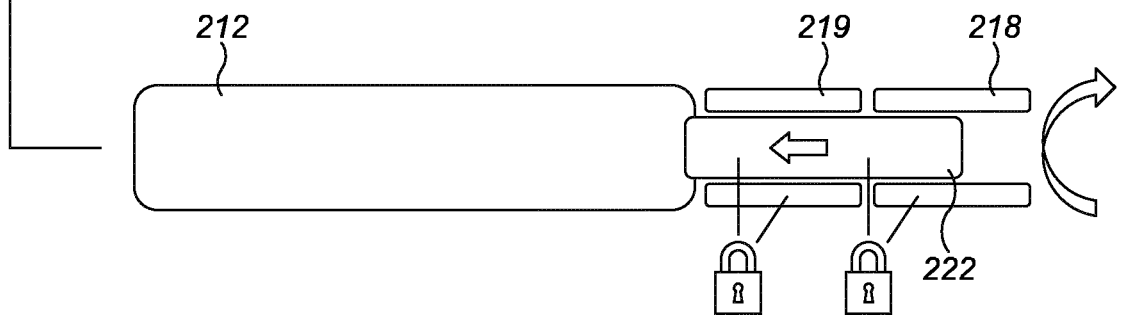
Figure 20:
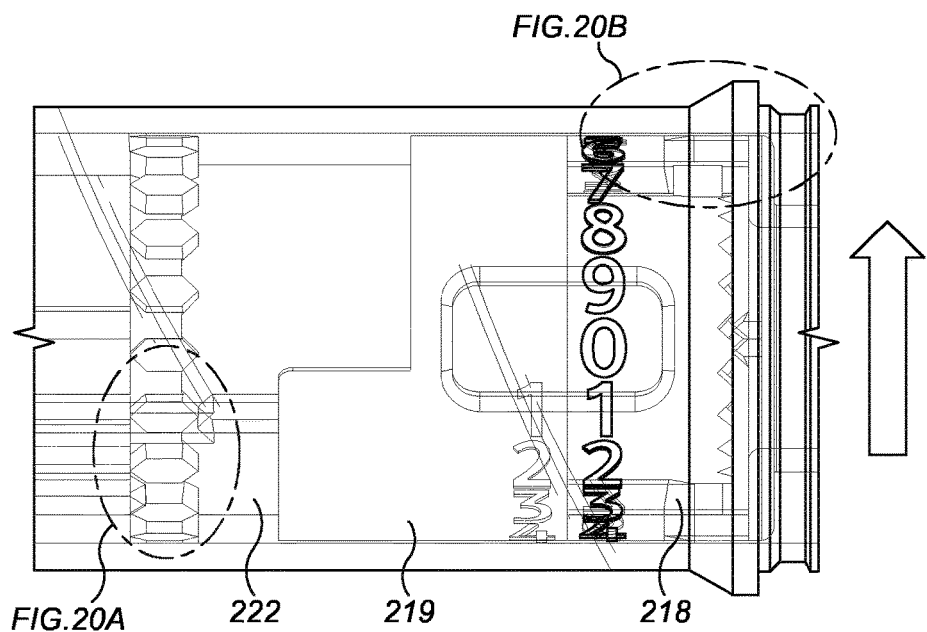
FIGS. 20, 20A and 20B show further detail of the stage illustrated in FIG. 19A.
Figure 21:
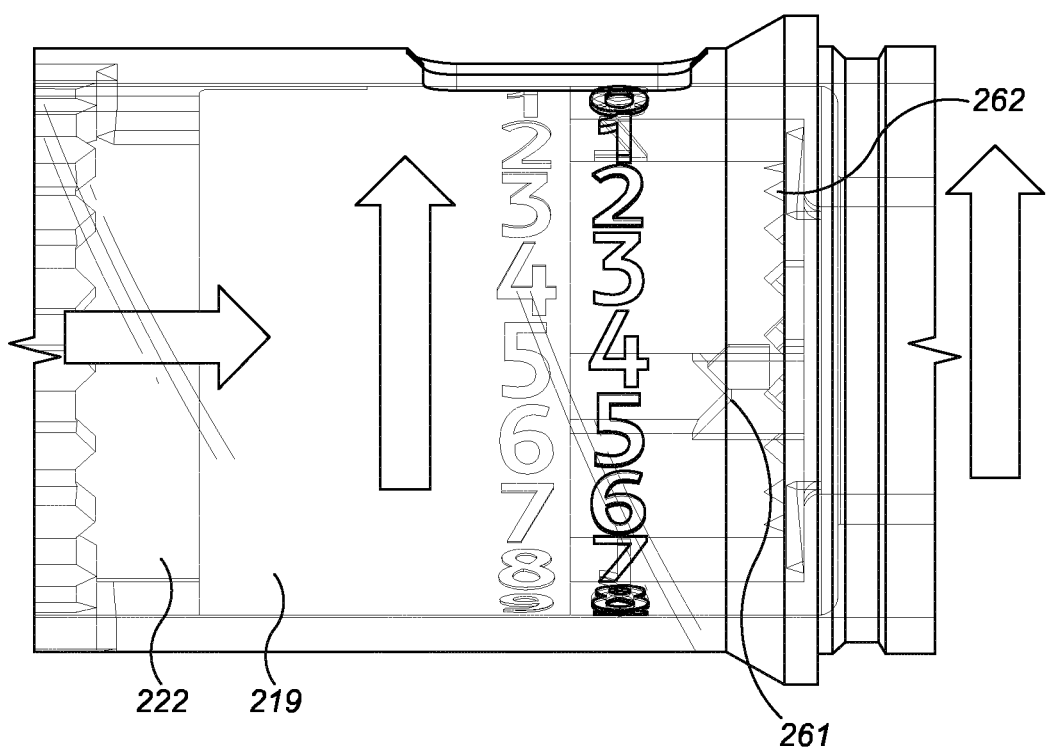
FIG. 21 shows further detail of the stage illustrated in FIG. 19B.
Figure 22:
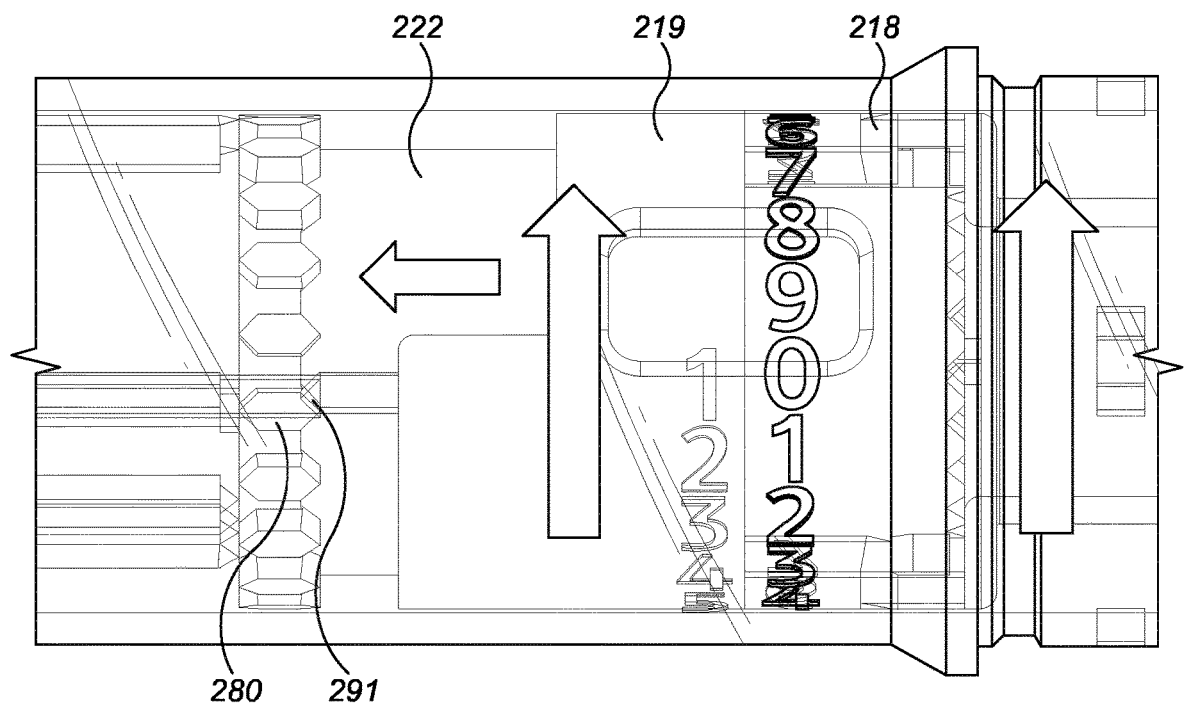
FIG. 22 shows further detail of the stage illustrated in FIG. 19C.

FIGS. 19A-19C show, in schematic form, the three stages of the odometer mechanism's operation. More detail of the respective stages is shown in FIGS. 20-22.

Figure 17:
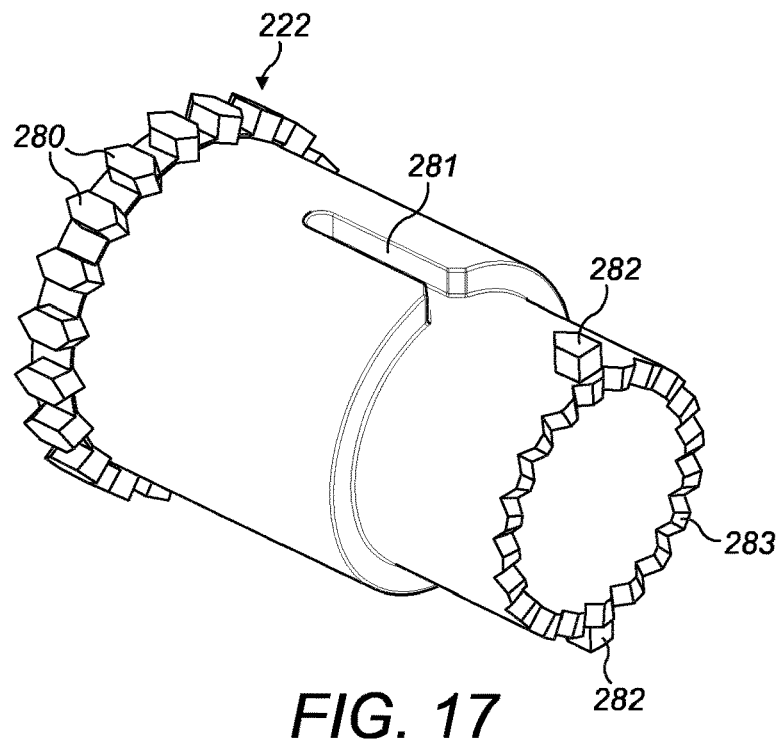
FIG. 17 is a perspective view of the shuttle lock from the odometer mechanism.
Figure 20A:
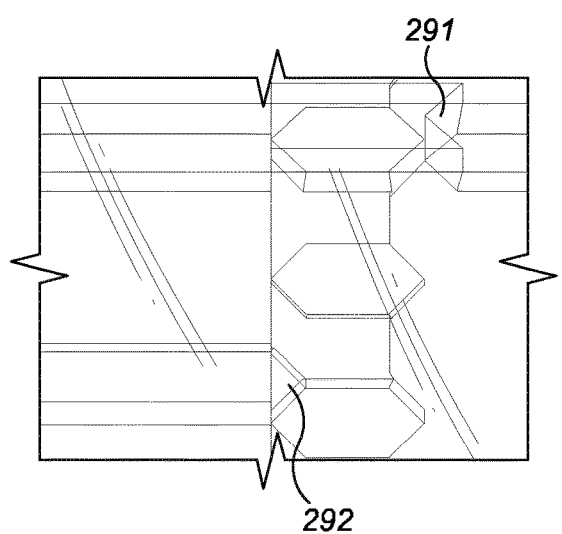
Figure 20B:
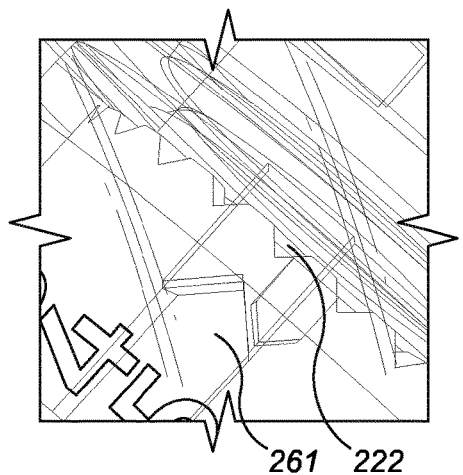

In stage 1 (FIGS. 19A, 20, 20A and 20B) for dose 0-9, the units wheel 218 is free to turn. Rotation of the dose selector 216 causes the dose to increment through doses 0-9. For doses 0-9, there is no engagement between the units wheel drive dogs 261 and the shuttle lock dogs 282 (FIG. 20B). The tens wheel 219 is rotationally locked but is axially moveable relative to the shuttle lock 222 because the key 273 is engaged in the keyway 281 (see FIG. 14). The shuttle lock 222 is rotationally locked to the housing 212 because the housing engagement ribs 292 (FIG. 20A) are engaged with three of the shuttle lock peripheral teeth 280 (FIG. 17).

After the units wheel has reached dose "9", in stage 2 (FIG. 19B and FIG. 21), the drive dogs 261 of the units wheel 218 engage shuttle lock dogs 282 during dose "10". The engagement of the angled faces of the dogs 261, 282, causes a camming action that moves the shuttle lock 222 axially rearwardly enough to disengage the shuttle lock peripheral teeth 280 from the housing engagement ribs 292. The shuttle lock 222 is therefore no longer rotationally locked to the housing 212. Since the key 273 is axially moveable in the keyway 281, the shuttle lock 222 is able to move axially relative to the tens wheel 219. Consequently, the tens wheel 219 itself does not move axially and the tens numbers 270 remain in a position adjacent to the units numbers 260. The axially rearward movement of the shuttle lock 222 causes angled faces of the dogs 261, 282 to reach the end of their sloping engagement, at which point the shuttle lock rear teeth 283 engage the axially-extending splines 262 on the units wheel 218. This rotationally locks the units wheel 218 and the shuttle lock 222 together.

The units wheel 218 is still able to turn. The tens wheel 219 is still rotationally locked to the shuttle lock 222 by virtue of the key 273 engaging in the keyway 281. Because the shuttle lock 222 (and hence the tens wheel 219 rotationally locked thereto) is rotationally locked to the units wheel 218 by the engagement of the units wheel splines 262 with the shuttle rear teeth 283, further turning of the units wheel 218 causes the shuttle lock 222 and the tens wheel 219 to rotate together.

After 9° of rotation of the shuttle lock 222 and tens wheel 219 by the units wheel 218, stage 3 is reached (FIG. 19C and FIG. 22), in which two of the shuttle lock peripheral teeth 280 come into contact with the angled faces of the two housing dogs 291.

Then, for the next 9° of rotation, the camming action of the angled faces of the housing dogs 291 and those of the shuttle lock peripheral teeth 280 cause the shuttle lock 222 to revert axially to re-engage the housing engagement ribs 292 so that the shuttle lock 222 is once again rotationally locked to the housing 212. Axial reversion of the shuttle lock 222 to its stage 1 forward position also causes the shuttle lock rear teeth 283 to disengage from the splines 262 on the units wheel 218. In this example, for every 18° of rotation (9°+9°), the shuttle lock completes a full cycle as described above. Other angles of rotation for each cycle are possible.

This completes the number change of the tens wheel 219. The mechanism functions in reverse if the dose is decremented.

Dose Setting—Maximum/Minimum Dose Limit

Figure 23A:
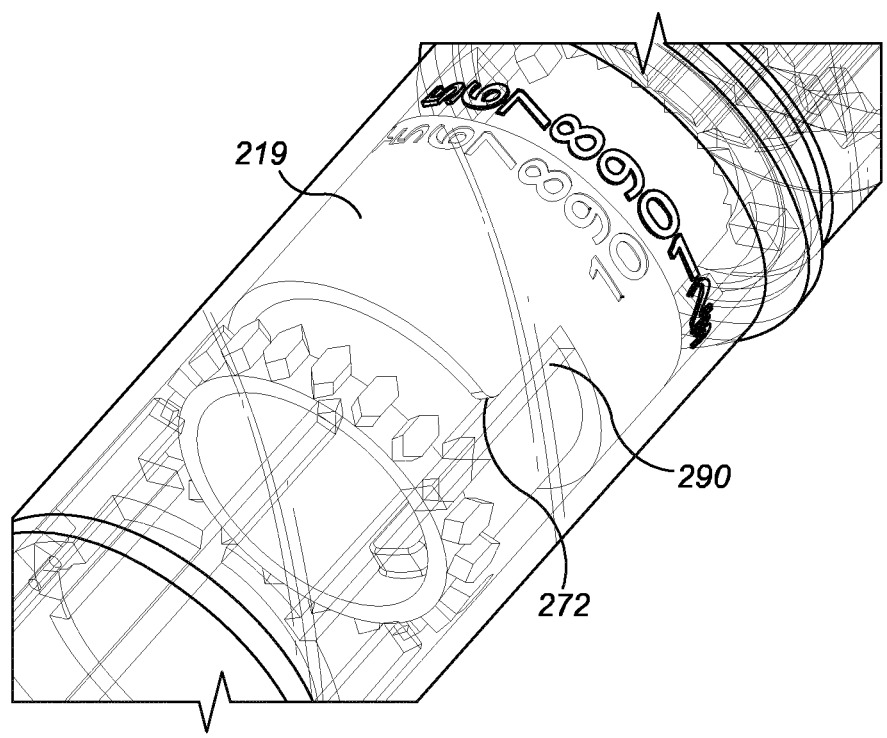
FIGS. 23A and 23B illustrate maximum/minimum dose limiting.
Figure 23B:
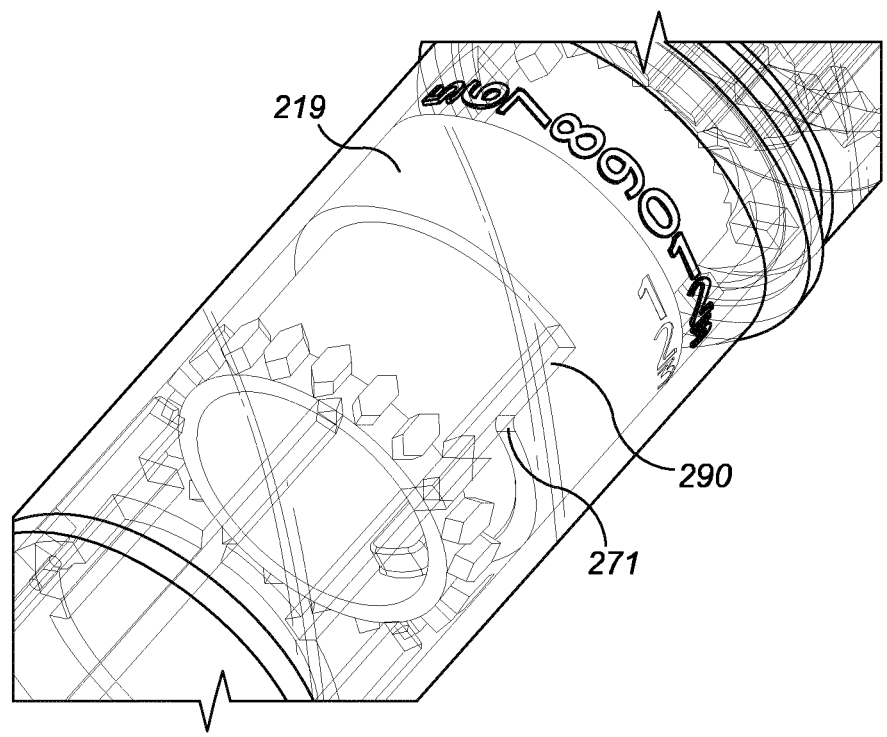

Limiting the maximum/minimum dose that can be set by the dose selector 216 is realised by cut out features 271, 272 on the tens wheel 219 which interact with a limit rib 290 on the housing. One side of the rib 290 limits the tens wheel at the minimum dose when feature 272 is rotated into abutment with the rib 290 (FIG. 23A). The other side of the rib 290 limits the tens wheel at the maximum dose, typically 100 IU, when feature 271 is rotated into abutment with the rib 290 (FIG. 23B). As mentioned above, the rib 290 is an extended part of one of the housing dogs 291 for engaging the shuttle lock 222.

Figure 24:
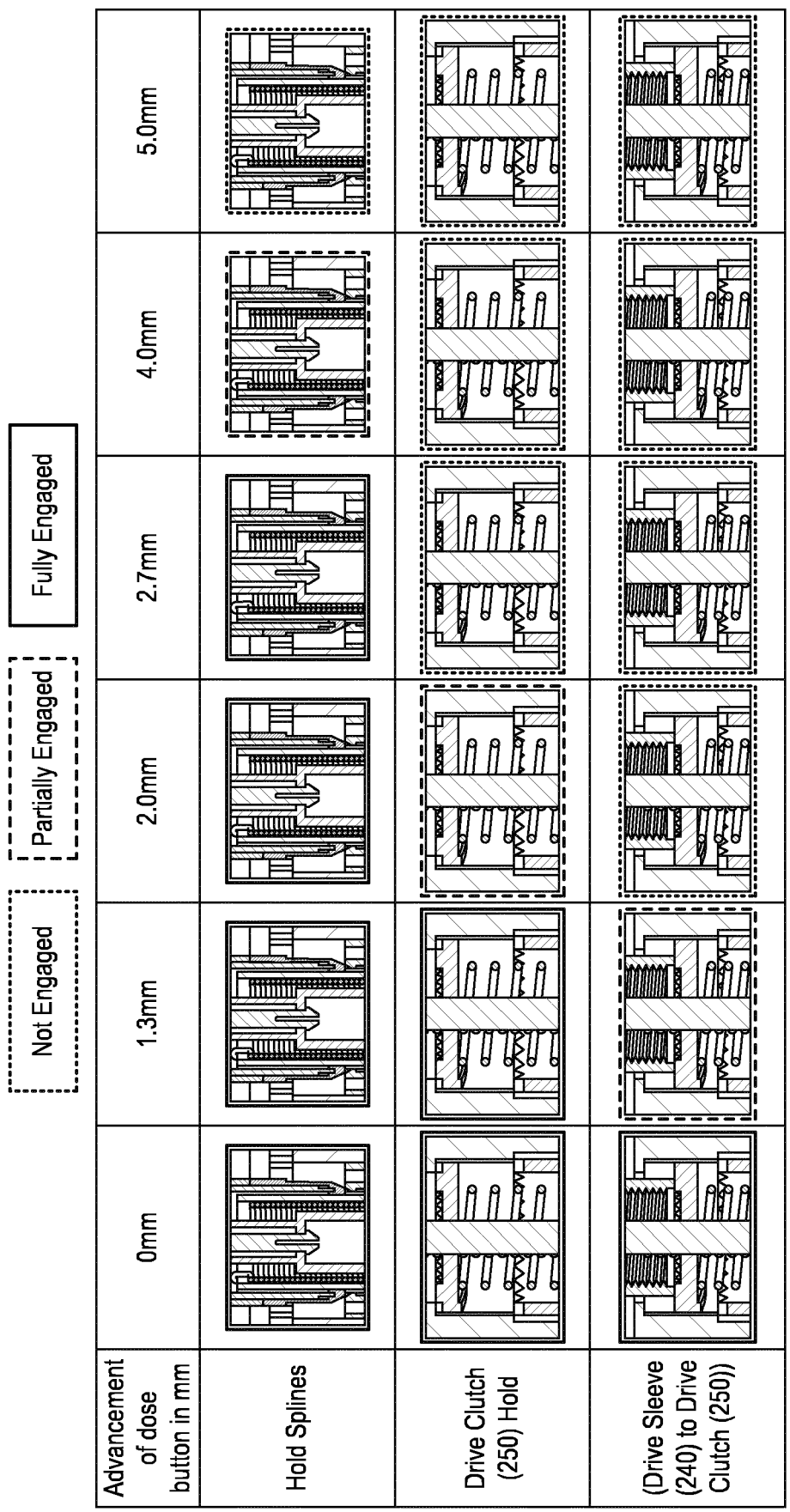
FIG. 24 is a diagrammatic summary of the key engagement points of the components of the injection device of FIG. 4, at six stages of dose delivery.
Figure 25:
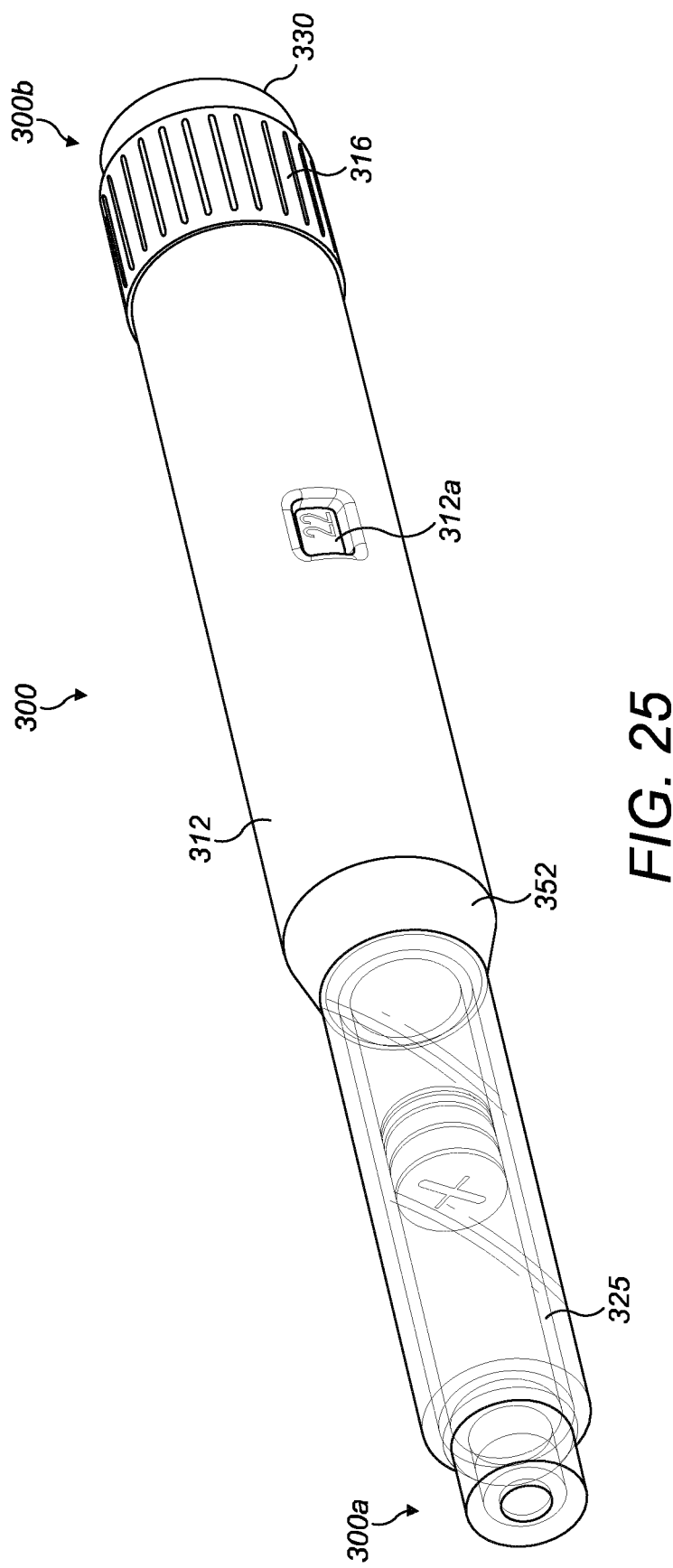
FIG. 25 is a perspective view of another embodiment of the injection device.
Figure 26:
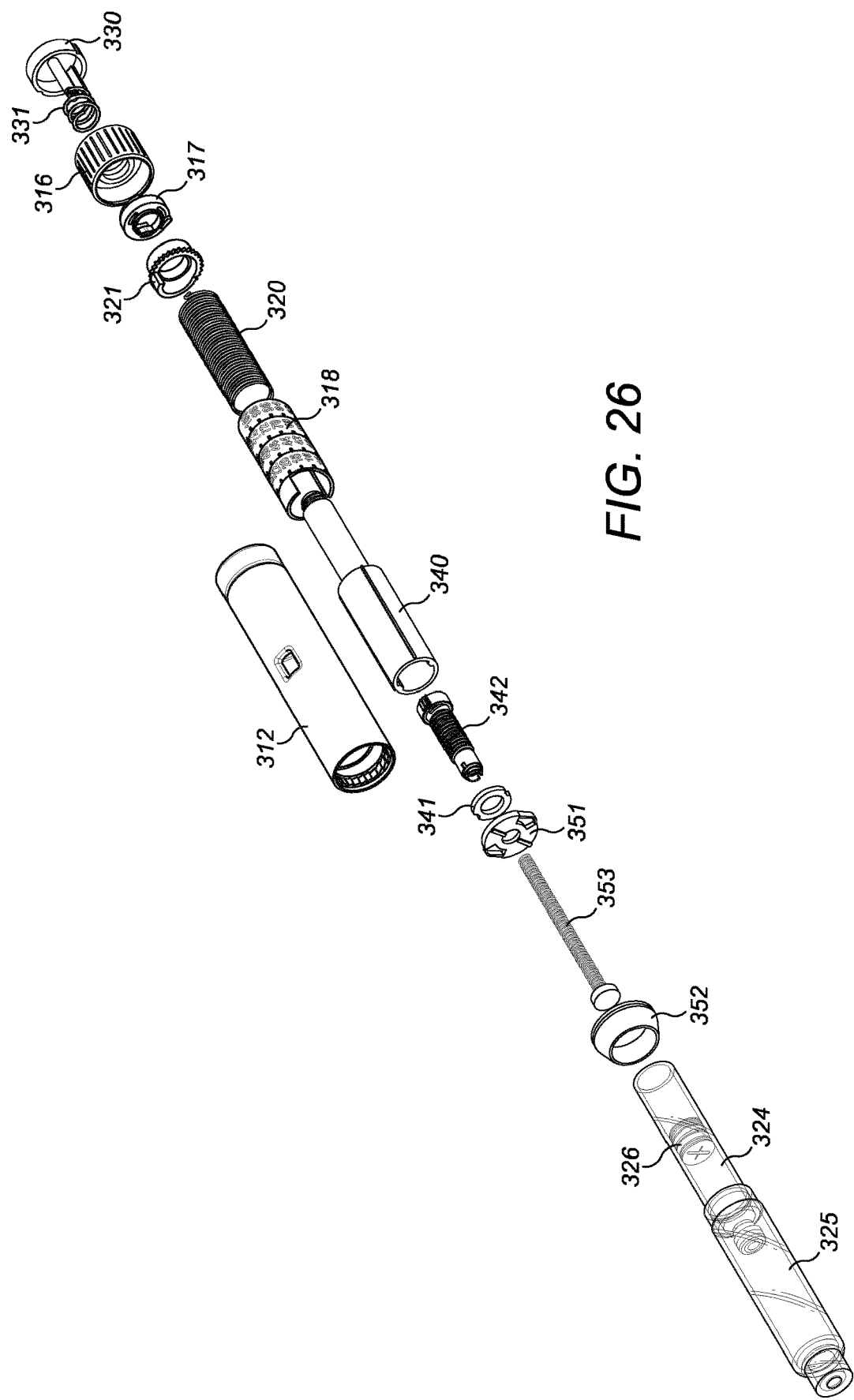
FIG. 26 is an exploded view of the injection device of FIG. 25.
Figure 27:
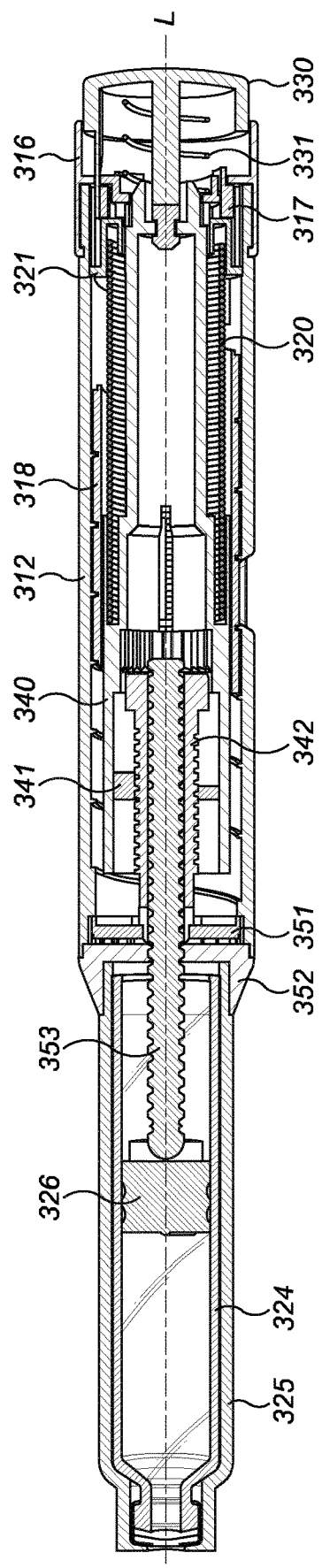
FIG. 27 is a cross-sectional view of the injection device of FIG. 25.
Figure 28:
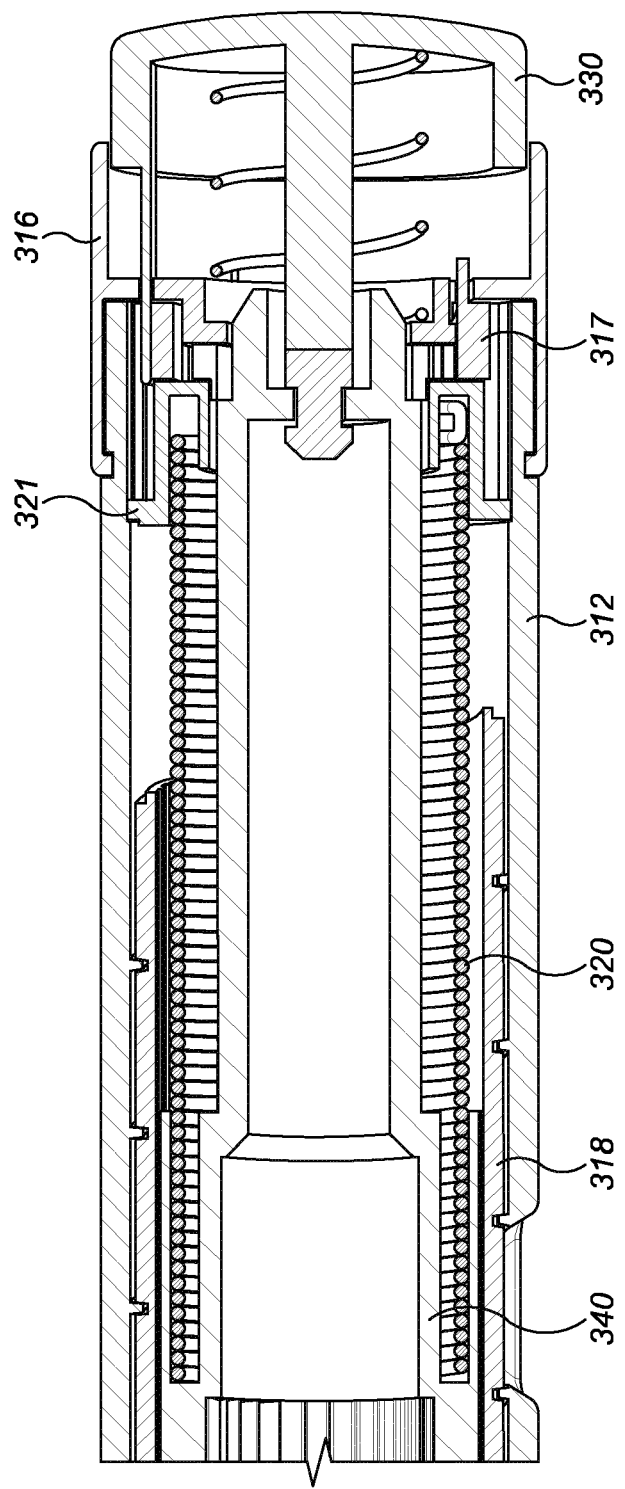
FIG. 28 shows the rear end of the injection device of FIG. 27, drawn to a larger scale.

FIG. 24 is a diagrammatic summary of the key engagement points of the injection device components, at six stages of dose delivery. Example distances of advancement of the dose button 230, starting at 0 mm, are shown. For each distance, each of the hold splines (ratchet pawls 217), drive clutch 250 and drive sleeve 240/drive clutch 250 are indicated as being either not engaged (dotted box outline), partially engaged (dashed box outline) or fully engaged (solid box outline).

As with the first embodiment, described, with reference to FIGS. 1-3, the ratchet arrangement is moveable between an engaged state in which the spring 220 is limited from unwinding from a currently selected dose and a disengaged state in which the spring 220 is able to unwind. The ratchet arrangement comprises a ratchet component 217b and an internal surface 213 of the housing 212.

The drive assembly includes a plunger element 253, 254 capable of providing an axial force for ejecting a dose of medicament from the injection device 200. The drive assembly also includes a drive clutch 250 moveable from a disengaged state in which a force path from the spring 220 to the plunger element 253, 254 is interrupted and an engaged state in which the drive assembly can provide the axial force for ejecting a dose of medicament from the injection device 200 via the force path.

Description of Third Example Embodiment

A further, non-limiting, embodiment of an injection device according to the present invention is illustrated in FIGS. 25-39C.

Referring to FIGS. 25-28, the injection device 300 includes a housing 312, a dose selector 316, a dose button 330 and dose button spring 331, a selector pawl 317, a spring lock 321, a drive spring 320, a number sleeve 318, a drive shaft 340, a drive sleeve 342, a lead screw 353, a last dose nut 341, a cap pawl 351, and a body cap 352, all located concentrically about a common longitudinal axis L. The axis L extends between a front end 300a and a rear end 300b of the injection device 300.

The injection device 300 has a medicament cartridge 324 supported in a cartridge holder 325 at the front end 300a of the injection device. The cartridge is sealed by an axially-moveable cartridge stopper 326 at its rear end.

The dose button 330 is biased rearwardly by the effect of the dose button spring 331 between the dose button 330 and the dose selector 316. The dose button 330 includes a ratchet disengagement finger 330a which can engage with the selector pawl 317.

The dose selector 316 is provided at the rear end 300b of the injection device 300 and is arranged to permit the selection of a desired dose of medicament for delivery from the medicament cartridge 324 into an injection site. The dose selector 316 is axially constrained with respect to the housing 312 but is rotatable with respect thereto, about axis L. The dose selector 316 is used to set the dose by increasing the rotational preload of the drive spring 320 which is prevented from unwinding by the selector pawl 317 which will be described in more detail below. A loose coupling between the dose selector 316 and the selector pawl 317 is provided via dose selector slots 316a (visible in FIG. 29A).

The selector pawl 317 has at least one ratchet arm 317b which is engageable with teeth 313 in an internal surface of the housing 312. The selector pawl 317 is also provided with at least one (preferably three equally spaced) selector pawl splines 317a which engage with the drive shaft 340. The selector pawl 317 is designed to be stiff in torsion but to have some flexibility in radial flexion (for example because of cutaways 317c behind the splines 317a.

A dose indicator, comprising a number sleeve 318 is disposed within the housing 312 and displays reference indicia, such as numbers or symbols, to indicate the level of dose selected by the dose selector 316. The housing 312 includes an aperture 312a through which the dose indicator is visible.

The drive spring 320 is a torsion spring which is fixed at one end with respect to the housing 312 via spring lock 321 and engaged at its other end to the drive shaft 340.

The rear end of the drive shaft 340 is provided with axially-extending splines 349. The selector pawl 317 is provided with one or more inwardly-directed splines 317a which can engage with the drive shaft splines 349 (FIG. 29B).

Figure 32:
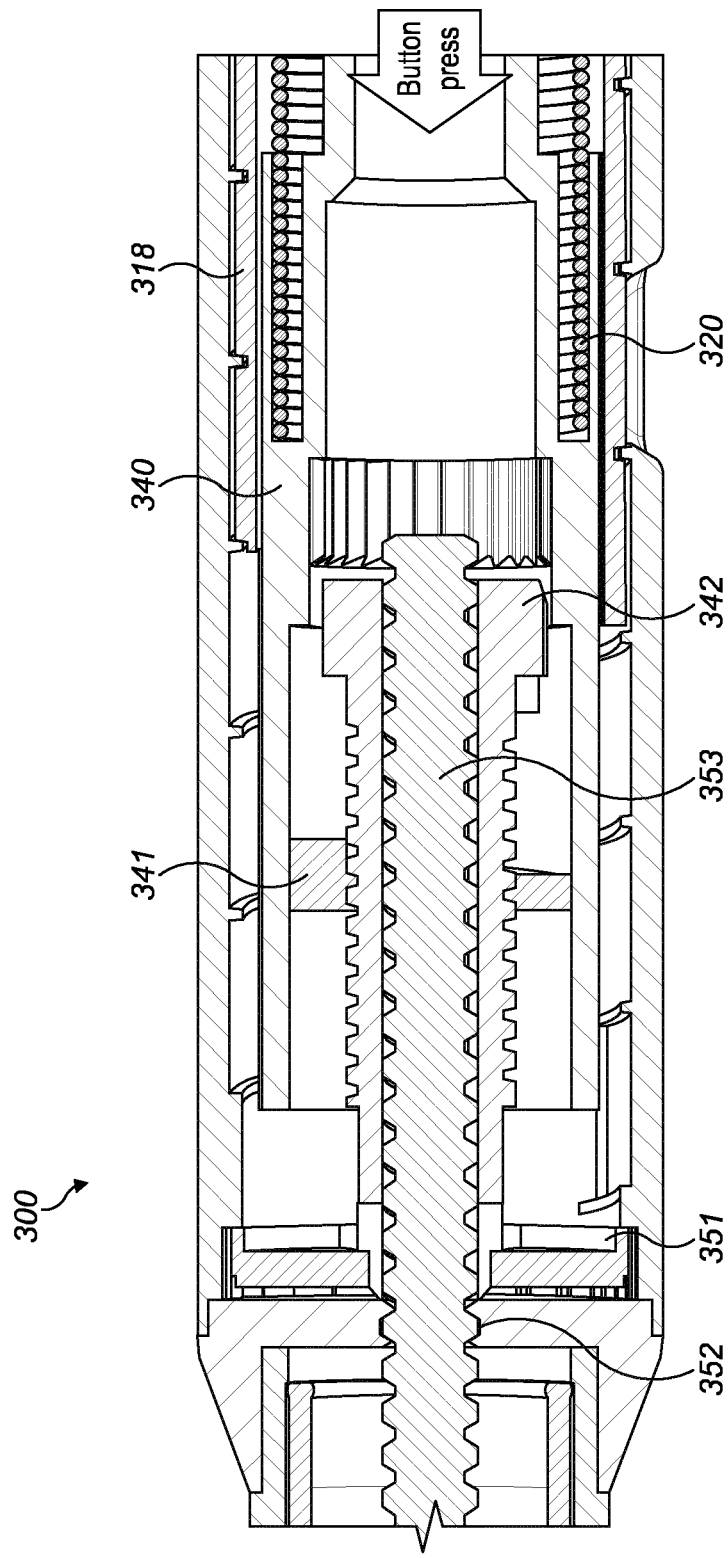
FIG. 32 is a cross-sectional view of a central portion of the injection device, showing key components involved in dose delivery.

FIG. 32 indicates the key components involved in delivery of a dose of medicament from the injection device 300. The drive spring 320 provides rotational energy for dose delivery. The drive shaft 340 couples the drive spring 320 to the drive sleeve 342, the last dose nut 341 and the number sleeve 318.

The drive sleeve 342 couples the drive shaft 340 to the lead screw 353 and also advances the last dose nut 341 during dose setting.

The lead screw 353 converts the rotation of the drive sleeve 342 to linear motion which can be used to depress the cartridge stopper 326 (not shown) to deliver medicament from the medicament cartridge 324.

The cap pawl 351 retains the drive sleeve 342 and provides a one-way ratchet to prevent back-drive of the lead screw 353. The cap pawl 351 may also provide haptic feedback of dose delivery.

The body cap 352 is threaded to allow the lead screw 353 to advance therethrough and serves as a thrust bearing for the drive sleeve 342.

Figure 36:
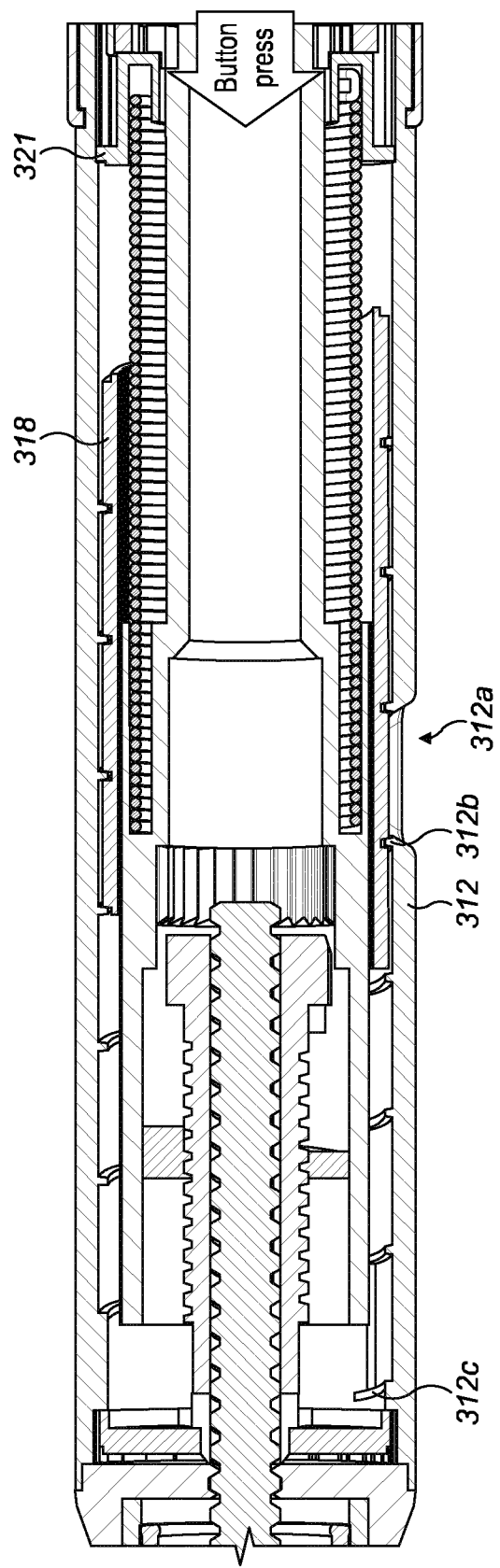
FIG. 36 is a cross-sectional view of a central portion of the injection device, showing key components involved in dose display.
Figure 37A:
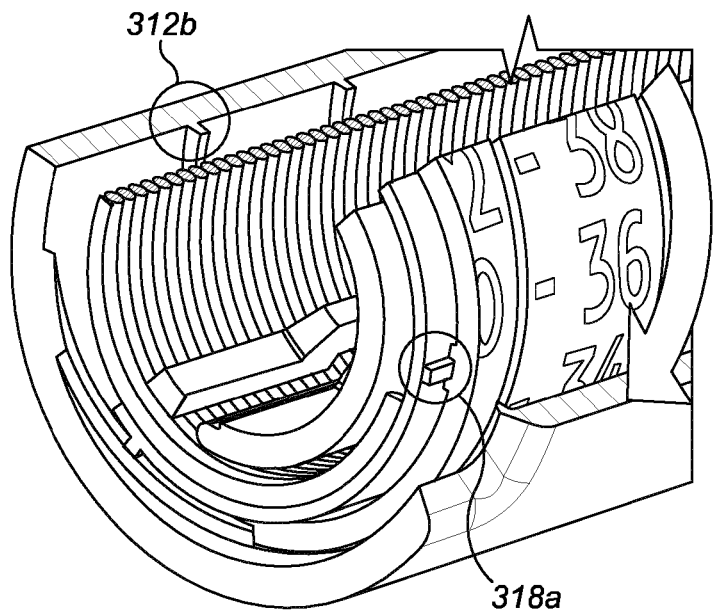
FIGS. 37A and 37B illustrate dose display.
Figure 37B:
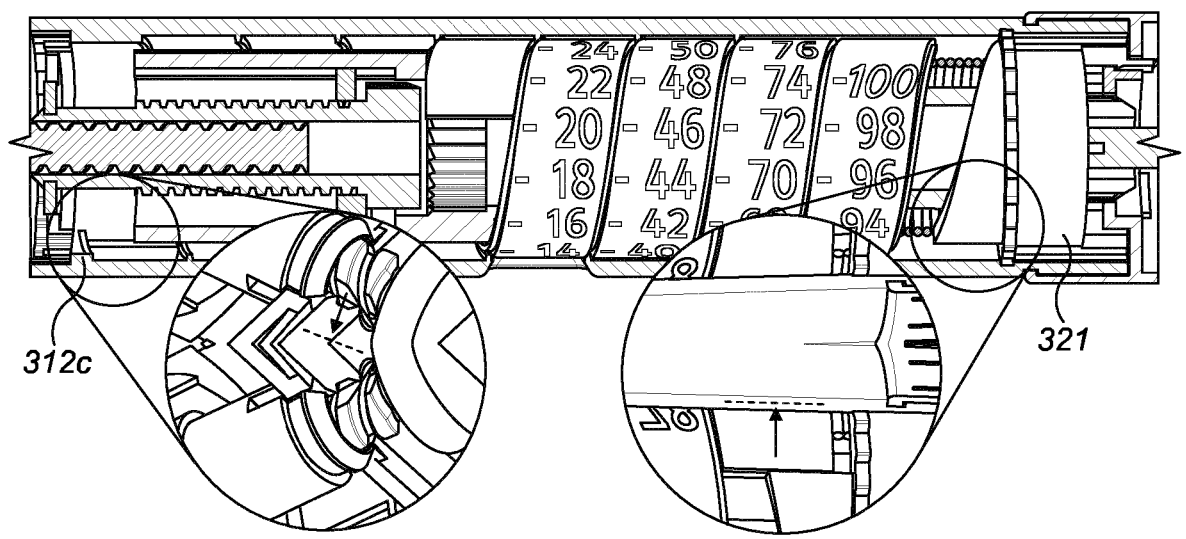

FIG. 36 gives an overview of the components involved in displaying the dose to the user. The spring lock 321 is engageable with the number sleeve 318 to provide a minimum dose end stop. The number sleeve 318 includes a spiral of numbers which display the selected dose through the aperture 312a in the housing.

The housing 312 is has an internal thread 312b to guide the number sleeve 318 as it rotates. A maximum dose end stop 312c for the number sleeve 318 is provided at the forward end of the housing 312.

The drive shaft 340 is rotationally coupled with the number sleeve 318 to communicate the rotational position of the drive spring 320 to the number sleeve 318. This coupling can be seen in FIG. 37A wherein a splined connection 318a between the number sleeve 318 and drive shaft 340 is present. As the drive shaft 340 rotates, the number sleeve 318 travels along the internal thread in the housing 312b, causing the number displayed in the aperture of the housing 312a to increase or decrease.

Figure 38:
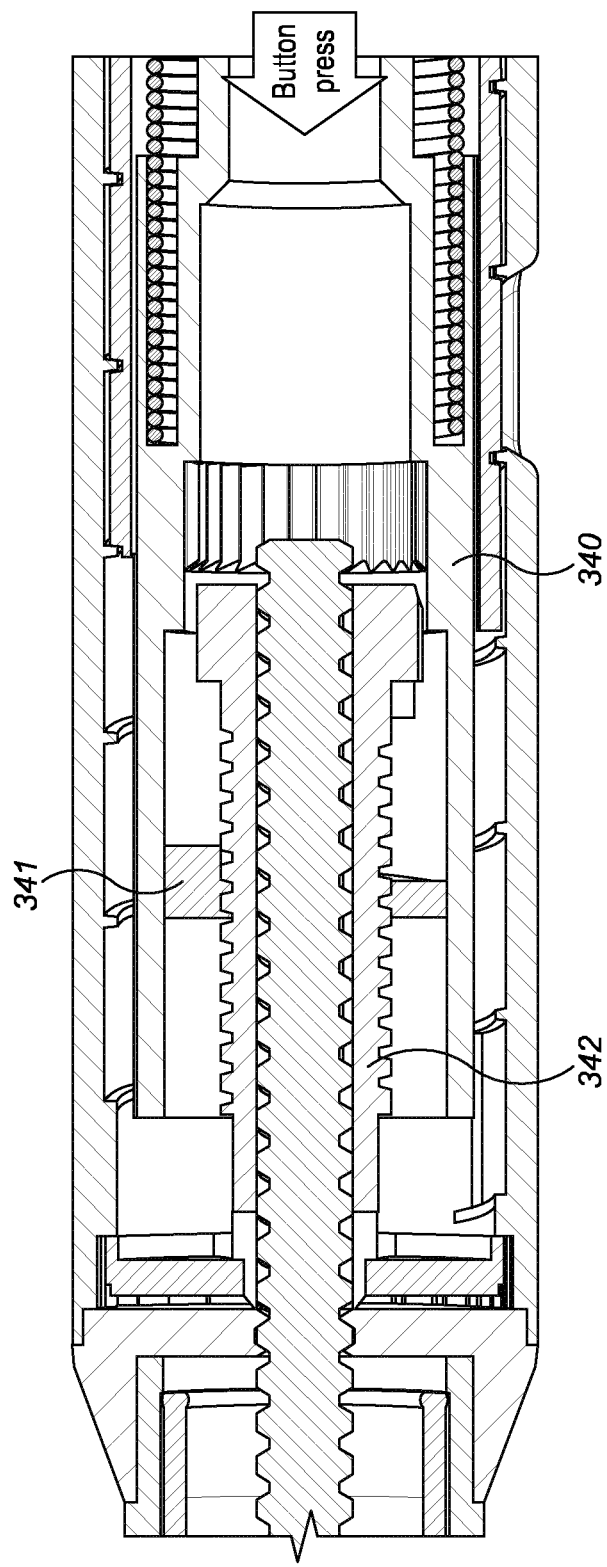
FIG. 38 is a cross-sectional view of a central portion of the injection device, showing key components involved in last dose protection.

FIG. 38 gives an overview of the components involved in last dose protection. The last dose nut 341 has a screw-threaded engagement with the drive sleeve 342 on its inner circumference. On the outer surface of the last dose nut 341 is a splined engagement with the inner surface of the drive shaft 340.

The operation of the respective features of the injection device 300 will now be described in more detail below.

Dose Setting—Incrementing the Dose

Figure 29A:
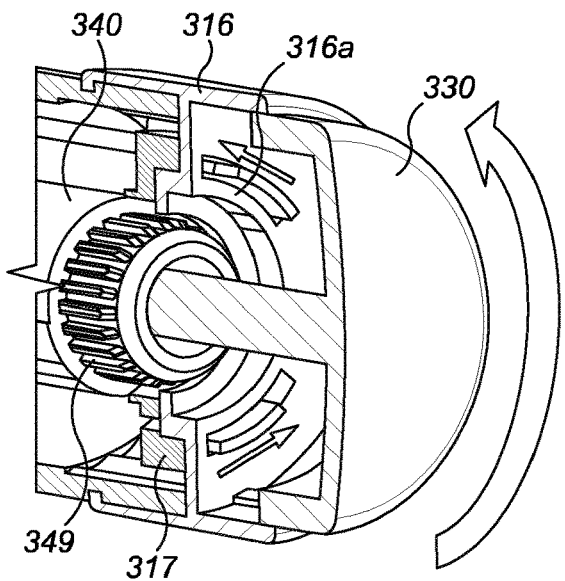
FIGS. 29A-29C illustrate incrementing the dose.
Figure 29B:
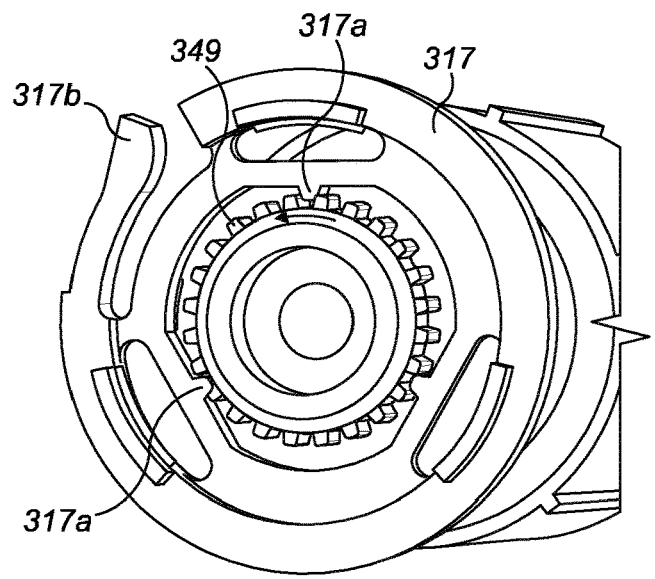

With reference to FIG. 29A, the user rotates the dose selector 316 in the anti-clockwise direction indicated. The dose selector 316 is tightly coupled to the dose button 330 which also turns. A loose coupling between the dose selector 316 and the selector pawl 317 (via dose selector slots 316a) causes the selector pawl 317 also to rotate anti-clockwise.

The selector pawl's inwardly-directed splines 317a can engage with the drive shaft splines 349 (FIG. 29B). As the selector pawl 317 rotates, the drive shaft 340 is also caused to rotate, which charges the drive spring 320. The number sleeve 318 is incremented to indicate the selected dose (the spring and number sleeve are not visible in FIG. 29B).

Figure 29C:
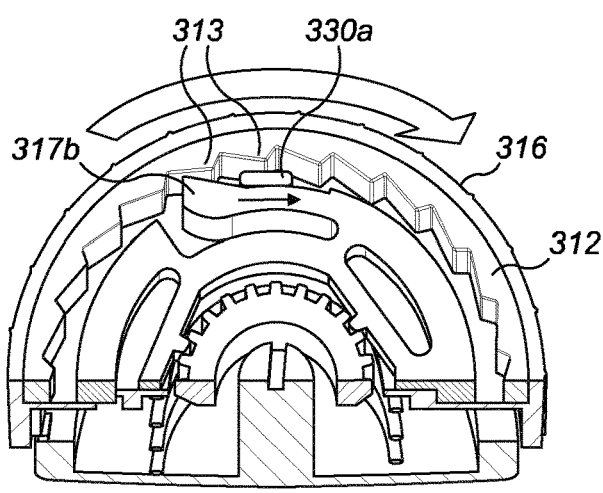

The selector pawl 317 has at least one ratchet arm 317b which engages with teeth 313 in an internal surface of the housing 312. This ratchet arrangement rotationally couples the selector pawl 317 and the housing 312 so that, in this coupled state, the spring 320 is prevented from unwinding when the dose selector 316 is released. Uncoupling of the ratchet arrangement allows relative rotation between the selector pawl 317 and the housing 312 so that, in this uncoupled state, the dose can be further incremented. Haptic feedback is provided per IU incremented as the ratchet arm 317b clicks over the housing teeth 313 (FIG. 29C).

Dose Setting—Decrementing the Dose

Figure 30A:
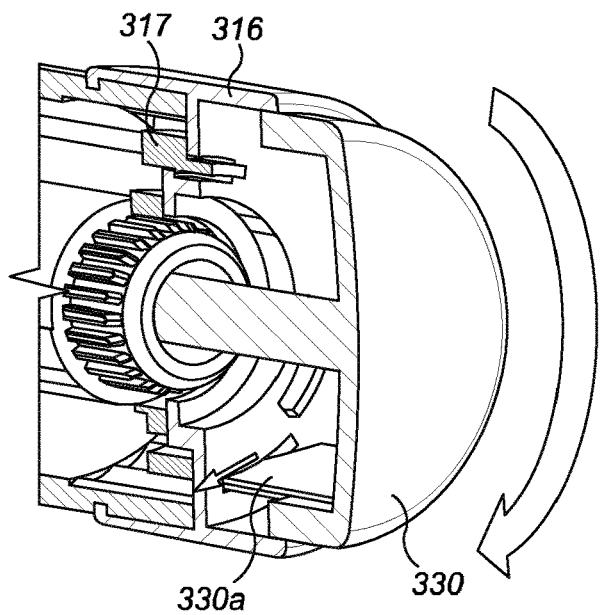
FIGS. 30A-30C illustrate decrementing the dose.

With reference to FIG. 30A, the user rotates the dose selector 316 in the clockwise direction indicated. The ratchet disengagement finger 330a built into the dose button 330 also moves clockwise (as the dose button 330 and dose selector 316 are rotationally coupled).

Figure 30B:
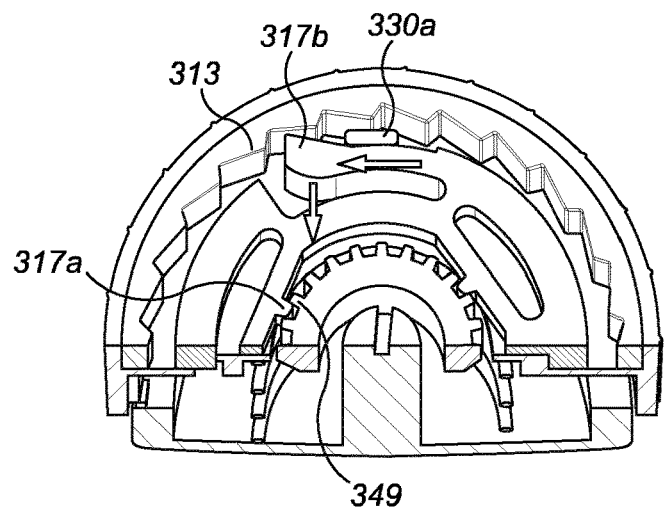

The ratchet disengagement finger 330a engages with the selector pawl ratchet arm 317b, depressing it radially inwardly by a sufficient amount to reduce the force required to shift the ratchet arm 317b over to the previous tooth 313 in the housing (FIG. 30B).

Figure 30C:
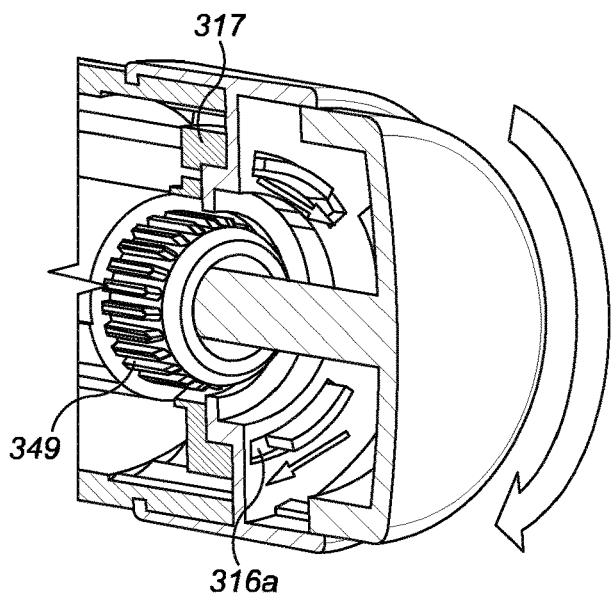

With the ratchet arm 317b partially disengaged, the selector pawl 317 engages the other end of dose selector slots 316a, turning the selector pawl 317 clockwise (FIG. 30C). The selector pawl splines 317a and drive shaft splines 349 cause the drive shaft 340 to rotate, unloading the drive spring 320 in order to decrease the dose.

Over-Torque Protection

Figure 31A:
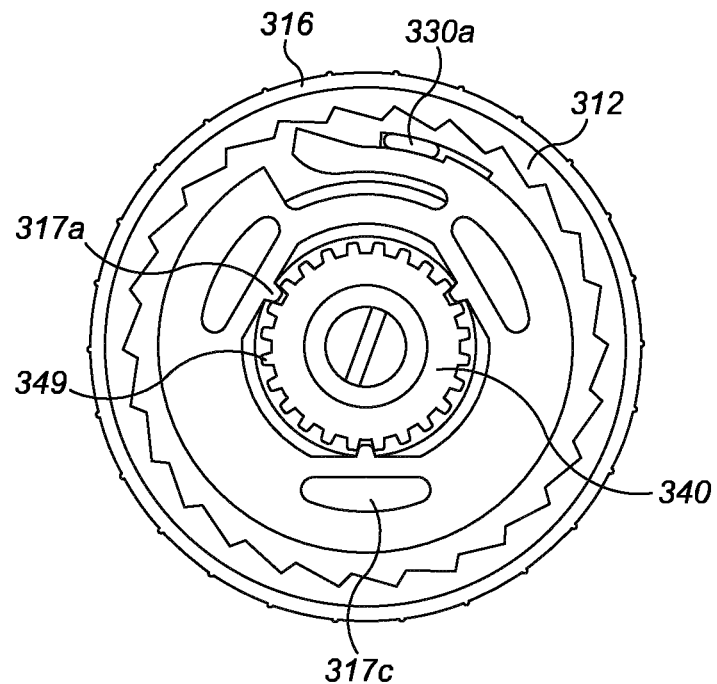
FIGS. 31A and 31B illustrate over-torque protection.
Figure 31B:
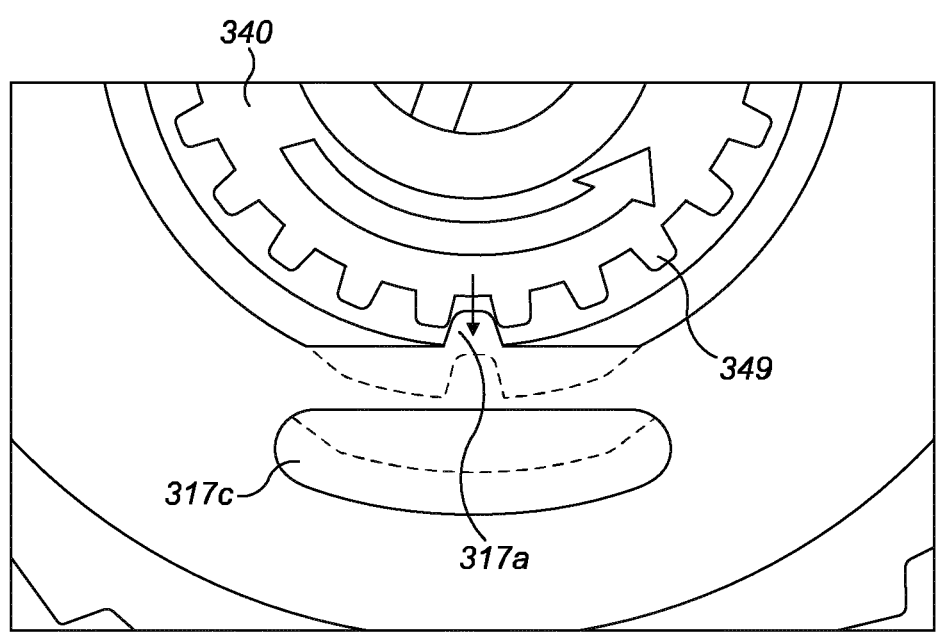

As shown in FIG. 31A, the dose selector 316 is connected to the drive shaft 340 via the selector pawl splines 317a. Owing to the angle of the splines 317a, a component of the torque between the selector pawl 317 and drive shaft 340 is resolved into a force radially outwards on the splines 317a. When the torque exceeds a defined limit, the radial component of the force causes the bridge of material holding the spline 317a to flex elastically into the position shown in dotted lines in FIG. 31B. The spline 317a thus disengages from the drive shaft splines 349. This disconnects the dose selector 316 from the internal components of the device, preventing torque in the device from exceeding the defined limit and potentially preventing damage to the device. The over-torque for flexing out the spline 317a to flex past spline 349 is preferably at least 10% higher than the torque required for dialling up (incrementing) or dialling down (decrementing) the dose selector 316. The dialling up torque can be 30 to 80 Nmm, preferably less than 60 Nmm, more preferably 30 to 50 Nmm. The dialling down torque can be 20 to 60 Nmm, preferably less than 50 Nmm, more preferably 30 to 40 Nmm. The over-torque in the dialling up direction may be different to the over-torque in dialling down direction.

Dose Delivery

Figure 33A:
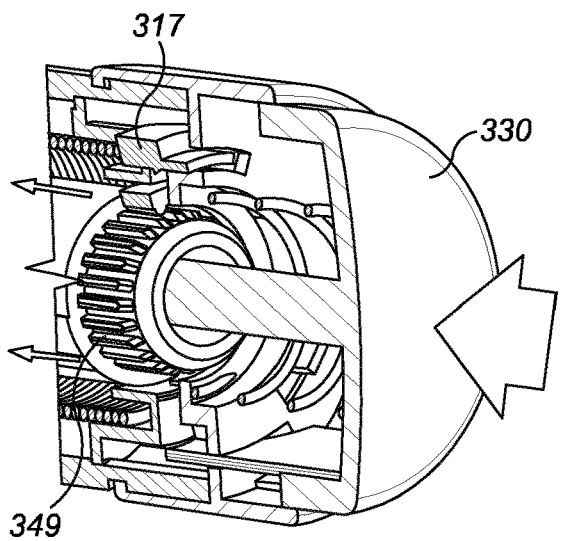
FIGS. 33A-33C illustrate dose delivery.

When it is desired to deliver a dose of medicament, the user depresses the dose button 330 as shown in FIG. 33A. Since the dose button 330 is axially coupled to the drive shaft 340, the drive shaft 340 moves axially forward, disengaging the drive shaft splines 349 from the selector pawl 317.

Figure 33B:
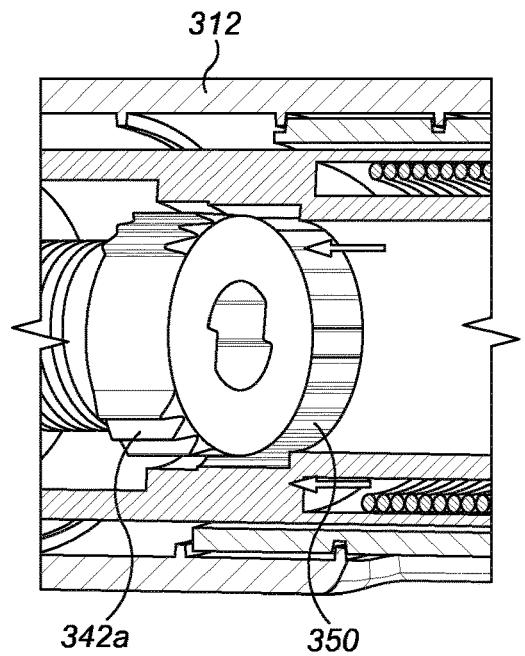

As the drive shaft 340 moves axially forward, the drive shaft splined clutch 350 engages with the drive sleeve splines 342a (FIG. 33B). This clutch engagement occurs before the selector pawl 317 is fully disengaged from the drive shaft splines 349 so that the drive spring 320 is never free to unwind in an uncontrolled manner. The splined clutch 350 and/or the drive sleeve splines 342a may be tapered to correct any potential misalignment.

Figure 33C:
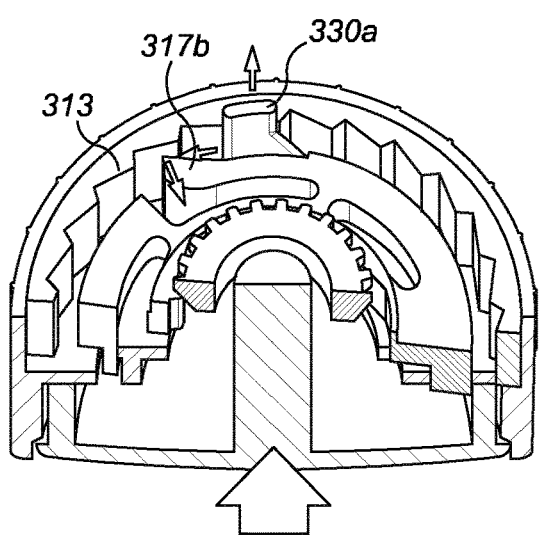

The ratchet disengagement finger 330a in the dose button 330 moves axially, exposing a wider section of the finger 330a which ensures the selector pawl ratchet arm 317b is disengaged from the housing teeth 313 during dose delivery (FIG. 33C). This avoids any erroneous haptic feedback being provided, should the dose selector 316 be rotated during dose delivery.

FIG. 34 is a diagrammatic summary of the key engagement points of the injection device components, at four stages of dose delivery.

Figure 35A:
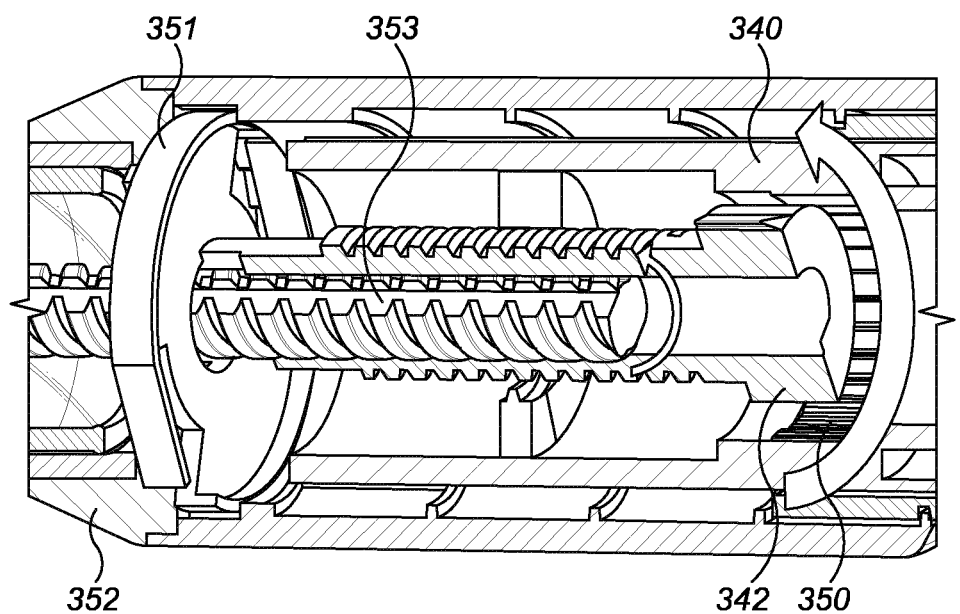
FIGS. 35A and 35B show how the lead screw is advanced during dose delivery.
Figure 35B:
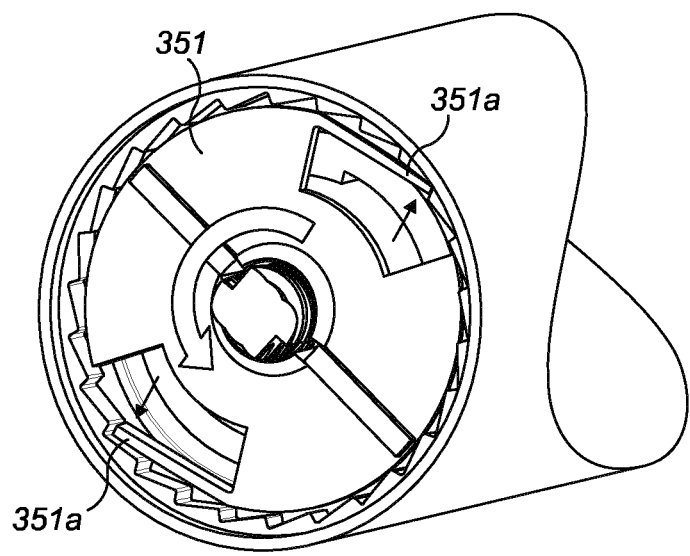

FIGS. 35A and 35B show how the lead screw 353 is advanced during dose delivery. Referring to FIG. 35A, once the dose selector 316 has been disengaged, the drive spring 320 drives the drive shaft 340 anti-clockwise. The drive shaft 340 turns the drive sleeve 342 via the drive shaft splined clutch 350. A keyed engagement between the drive sleeve 342 and the lead screw 353 turns the lead screw 353. As the lead screw 353 turns, it advances through a screw thread in the body cap 352, causing the cartridge stopper 326 to advance forward to deliver medicament.

Referring to FIG. 35B, the drive sleeve 342 is coupled to the cap pawl 351 which has pawls 351a which engage with a second set of housing teeth 314 to provide haptic feedback during dose delivery as well as preventing the lead screw 353 and drive sleeve 342 from being back-driven.

Dose Display and Maximum/Minimum Dose End Stops

Travel of the number sleeve 318 is limited by end stops which serve as maximum and minimum dose protection. The maximum dose end stop 312c is shown on the left side of FIG. 37B, the dotted line showing the angle at which the number sleeve 318 approaches the end stop 312c. The minimum dose end stop is provided by the spring lock 321, shown on the right side of FIG. 37B, the dotted line showing the angle at which the number sleeve 318 approaches the spring lock 321. The minimum dose may be 0 IU and the maximum dose may be 100 IU. Once either of the end stops is engaged, further rotation of the number sleeve 318 is prevented which, in turn, prevents further rotation of the drive shaft 340. This prevents the user incrementing the dose beyond the maximum or decrementing the dose below the minimum. The minimum dose end stop on the spring lock 321 also prevents the drive spring 320 from unwinding below zero IU during dose delivery.

Last Dose Protection

Figure 39C:
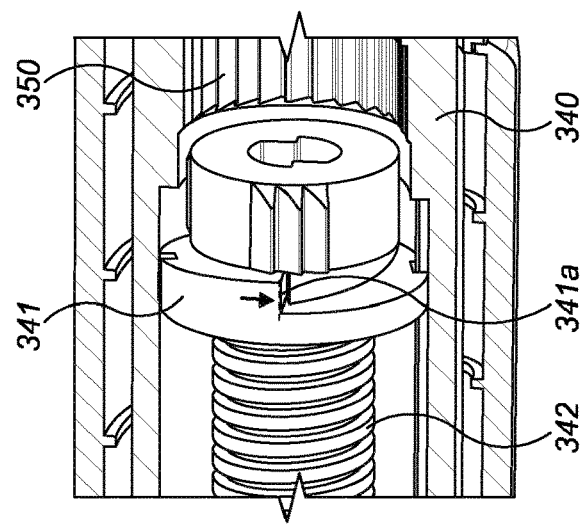
FIGS. 39A-39C illustrate last dose protection.
Figure 39B:
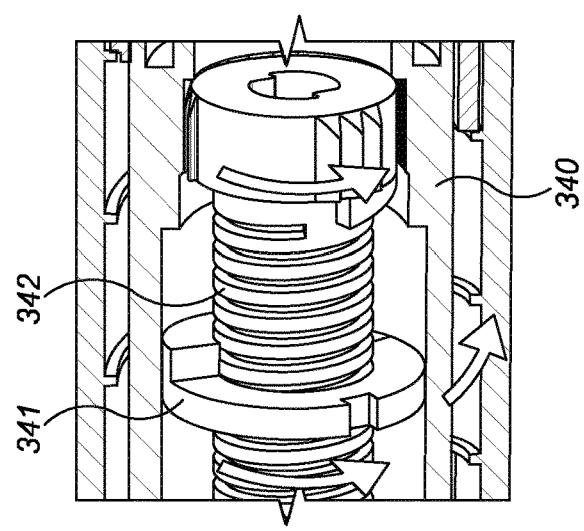
Figure 39A:
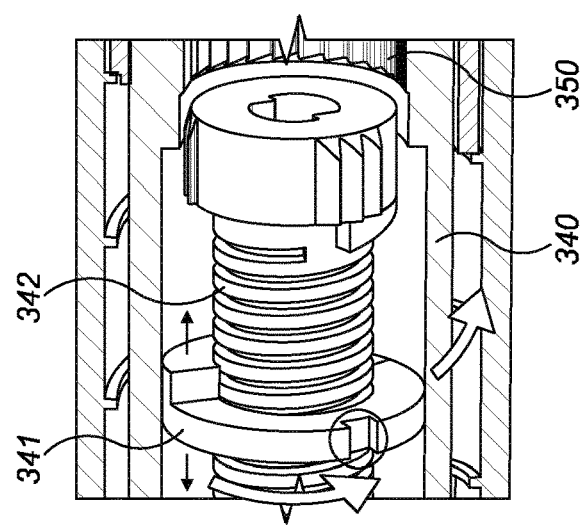
Figure 40:
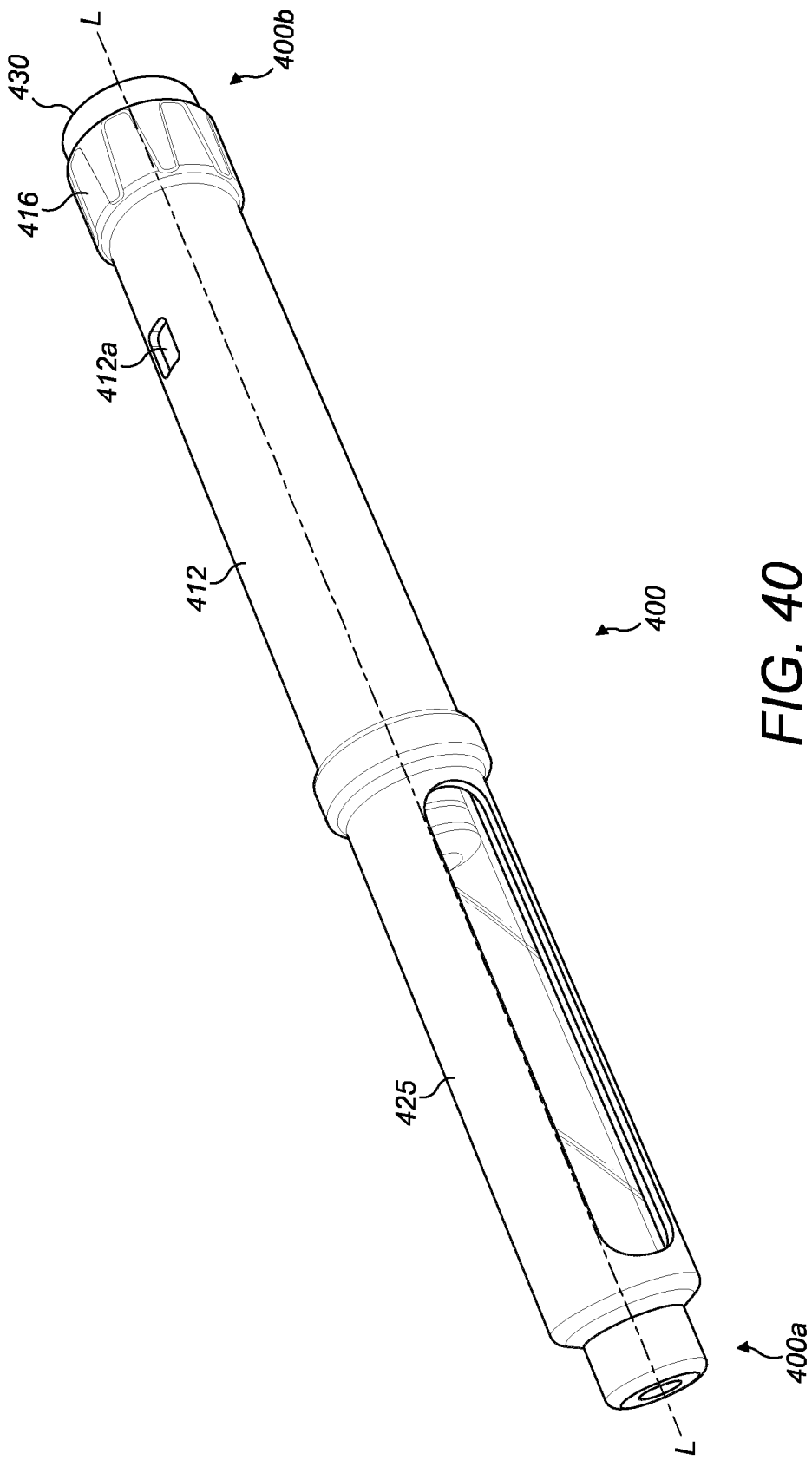
FIG. 40 is a perspective view of an injection device in accordance with an embodiment of the present invention.
Figure 41:
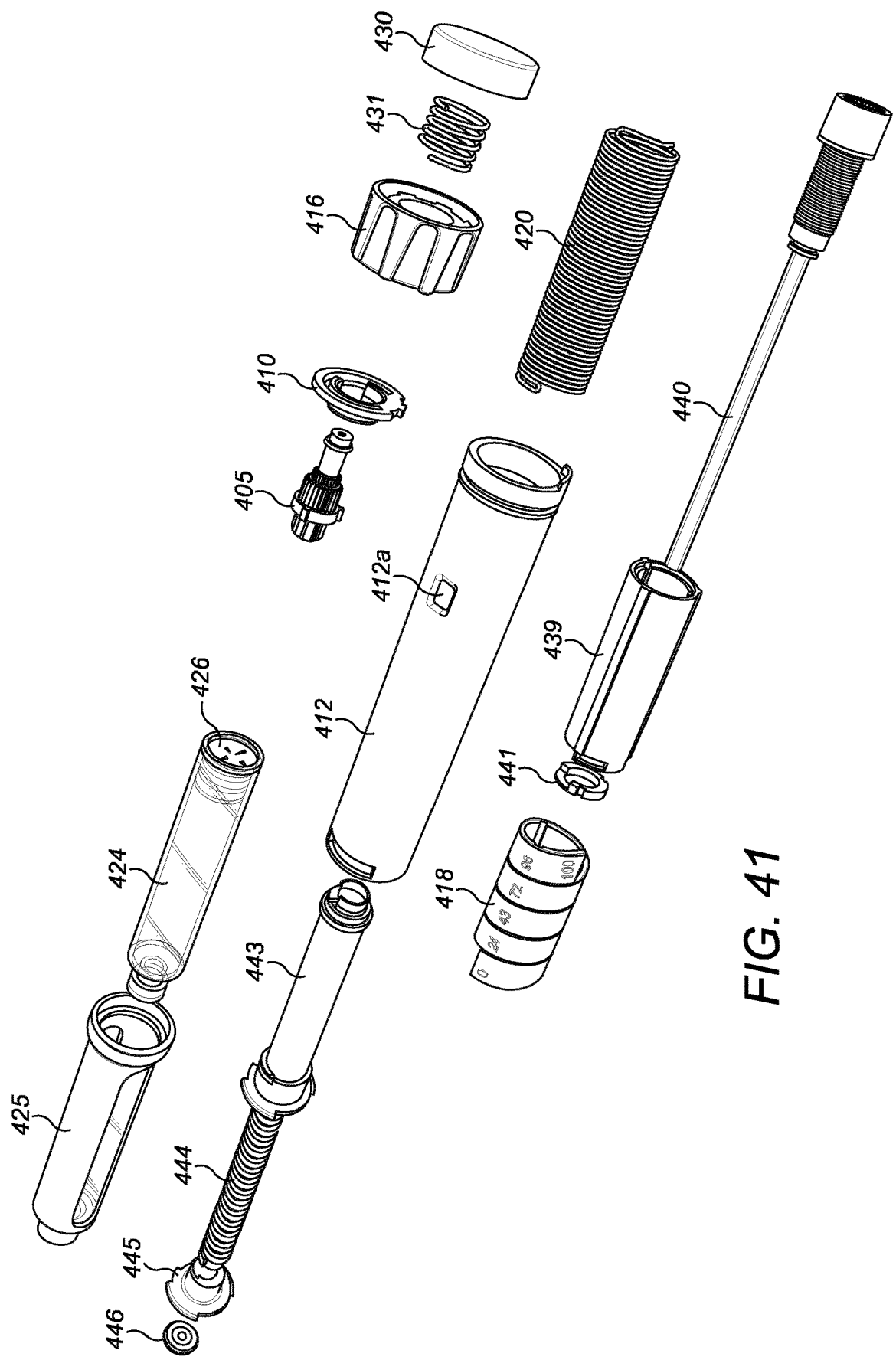
FIG. 41 is an exploded view of the injection device of FIG. 40.

As shown in FIG. 39A, as the drive shaft 340 rotates during dose setting, the last dose nut 341, which is splined thereto, also rotates. This enables the last dose nut 341 to travel left or right along the screw thread on the drive sleeve 342. As the dose is incremented, the last dose nut 341 moves right until, after a preset maximum number of doses have been delivered by the device, the last dose nut 341 is in the position illustrated in FIG. 39C.

During dose delivery, the drive shaft 340 and drive sleeve 342 are rotationally coupled together via the drive shaft splined clutch 350 so that there is no relative rotation between them. Therefore, during dose delivery (FIG. 39B), the last dose nut 341 cannot travel along the screw thread on the drive sleeve 342.

After the preset maximum number of doses has been delivered, a rotational endstop 341a on the last dose nut 341 engages with a rotational stop on the drive sleeve 342, as indicated by the dotted line and arrow in FIG. 39C. This prevents any further relative rotation between the drive sleeve 342 and the drive shaft 340, meaning that the user can no longer increment the dose setting. Any remaining dose can be delivered as normal.

As with the first embodiment, described, with reference to FIGS. 1-3, the ratchet arrangement is moveable between an engaged state in which the spring 320 is limited from unwinding from a currently selected dose and a disengaged state in which the spring 320 is able to unwind. The ratchet arrangement comprises a ratchet component 317b and an internal surface 313 of the housing 312

The drive assembly includes a plunger element 353 capable of providing an axial force for ejecting a dose of medicament from the injection device 300. The drive assembly also includes a drive clutch 350, 342a moveable from a disengaged state in which a force path from the spring 320 to the plunger element 353 is interrupted and an engaged state in which the drive assembly can provide the axial force for ejecting a dose of medicament from the injection device 300 via the force path.

Description of Fourth Example Embodiment

An injection device 400 according to a non-limiting example embodiment of the present invention is shown in FIGS. 40-83. The injection device 400 is configured to deliver a dose of medicament and extends along a longitudinal axis L between a front end 400a and a rear end 400b of the injection device 400. The injection device 400 has a housing 412 and is able to receive a needle (not shown) at the front end 400a. A dose selector 416 is provided at the rear end 400b and is arranged to permit the selection of a desired dose of medicament for delivery through the needle into an injection site. The housing 412 includes an aperture 412a through which a dose indicator, for example a number sleeve 418 is visible.

A cartridge holder 425 holds a medicament cartridge 424 from which medicament is expelled by the forward axial movement of a cartridge stopper 426. The cartridge stopper 426 is driven axially forward by a drive mechanism described later below.

Figure 42:
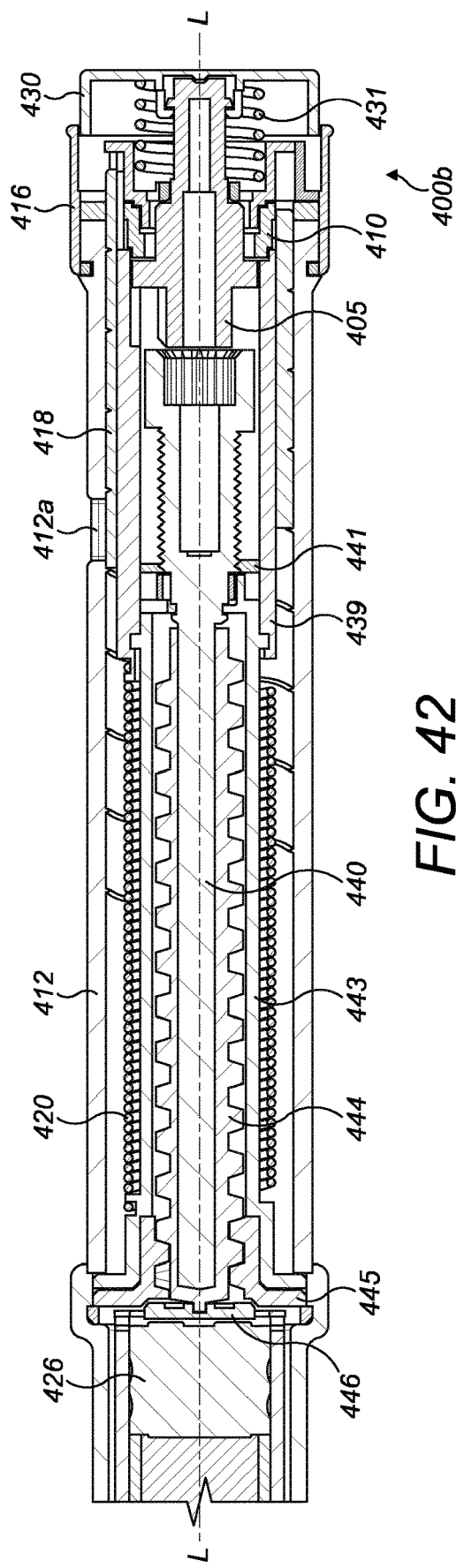
FIG. 42 is a cross-sectional view of selected components of the injection device of FIG. 40.

Referring to FIG. 42, the components of the injection device are arranged generally concentrically about longitudinal axis L. Beginning at the rear end 400b of the injection device 400, a dose button 430 is biased axially rearward by a dose button spring 431. Three interacting components, the dose selector 416, a ratchet ring 410 and a drive plate 405 are involved in a dose setting mechanism which sets the desired dose to be delivered.

A drive spring 420 is attached at one end to a chassis 443 which is fixed with respect to the housing 412. The other end of the drive spring 420 is fixed to a drive sleeve 439.

A last dose nut 441 is threaded to an elongate drive shaft 440. An external surface of the last dose nut 441 has three equally spaced grooves 441a in which internal splines 439b on the drive sleeve engage. The last dose nut 441 also has an endstop 441b for engaging with a correspondingly-shaped endstop 440a on the drive shaft 440.

Figure 70:
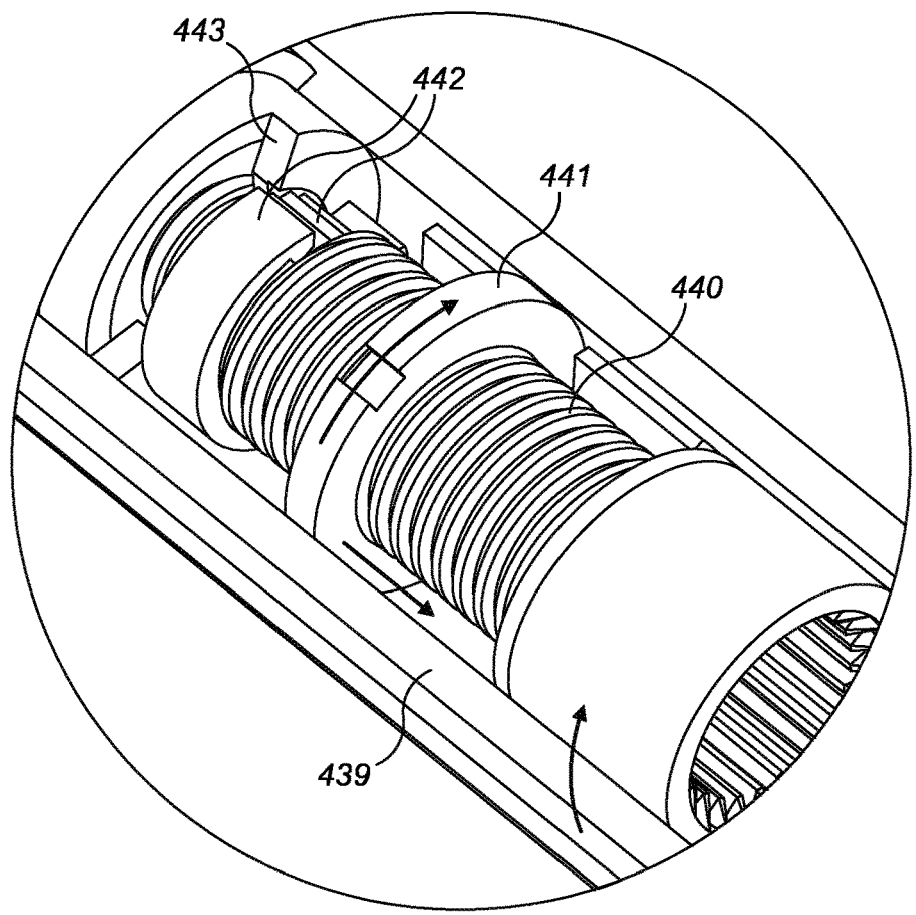
FIGS. 70-72 illustrate the last dose protection feature.
Figure 71:
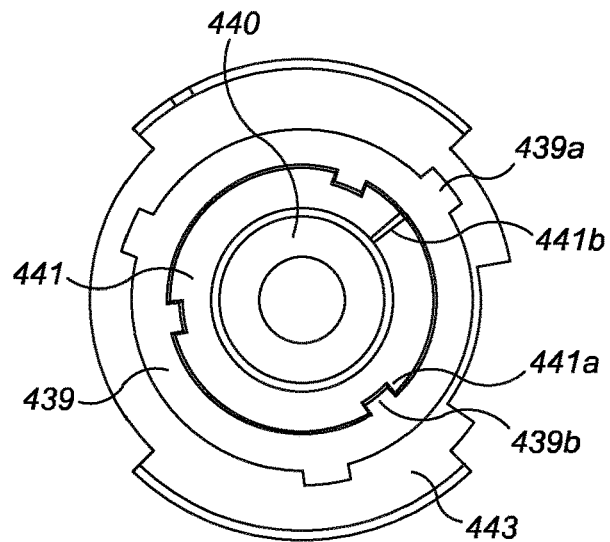
Figure 72:
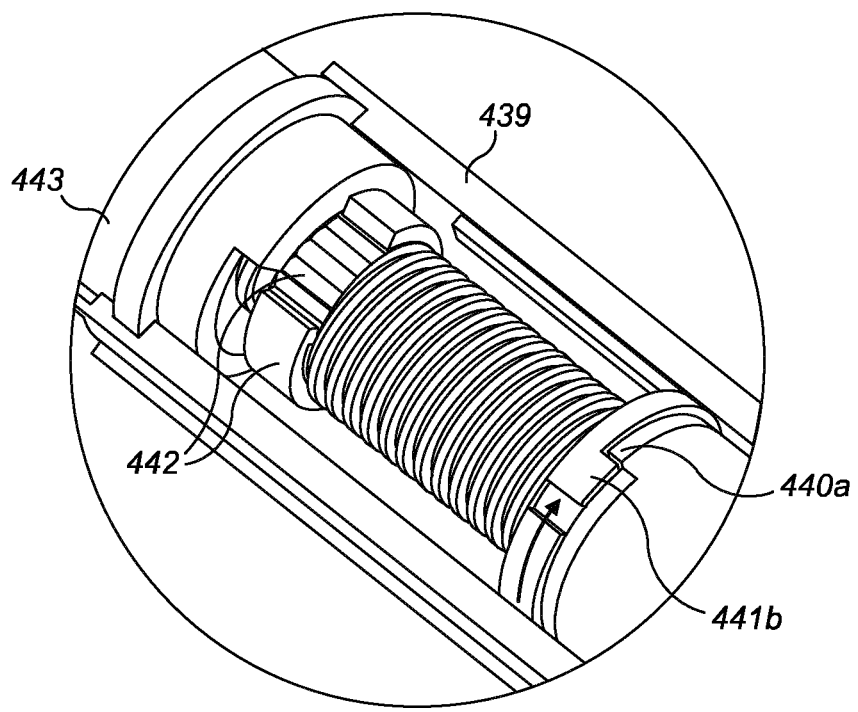

As shown in FIGS. 70-72, the drive shaft 440 is rotationally locked to the chassis 443 by a chassis ratchet 442. The chassis ratchet 442 is a one-way ratchet which locks the drive shaft 440 to the chassis 443 in a clockwise (dose setting) direction, whilst allowing relative rotation of the drive shaft 440 with the chassis 443 in an anti-clockwise (dose delivery) direction. A rear end of the drive shaft 440 is provided with a set of internal splines 440b (FIG. 77B) which can engage with the drive plate 405. A front end of the drive shaft 440 is provided with a set of external splines 440c (FIG. 81) for keying i.e. rotationally locking the drive shaft 440 to a hollow plunger 444.

The hollow plunger 444 is capable of converting rotation of the drive shaft 440 into linear (axial) motion via a thrust nut 445 (an external screw thread of the plunger 444 being engaged with the thrust nut 445). A plunger bearing 446 at the forward end of the plunger 444 can be pushed axially against the cartridge stopper 426 to expel medicament.

Figure 43A:
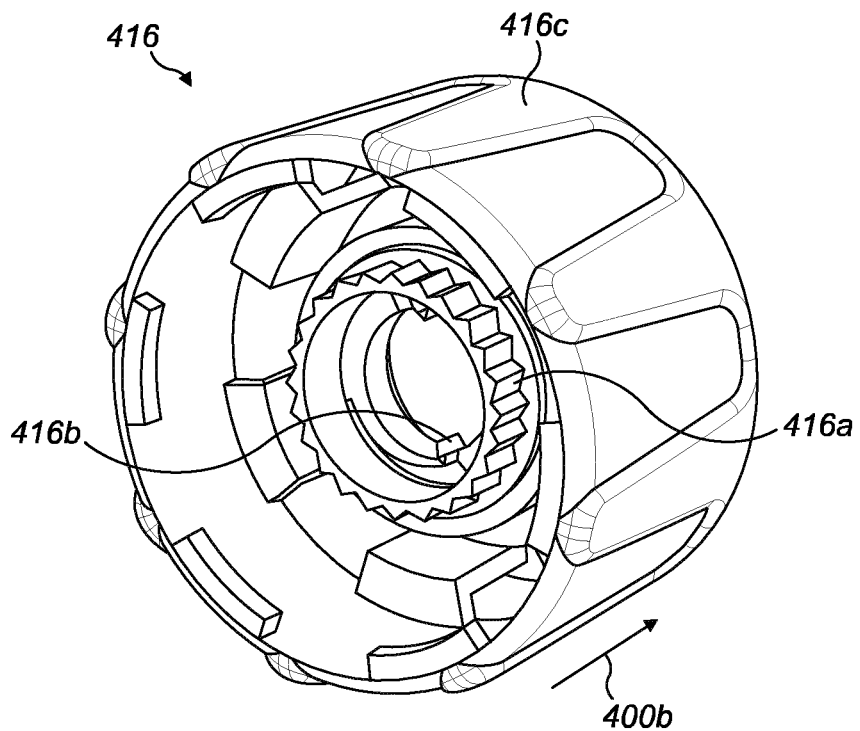
FIG. 43A is a perspective view of the dose selector, viewed from the front of the injection device.
Figure 43B:
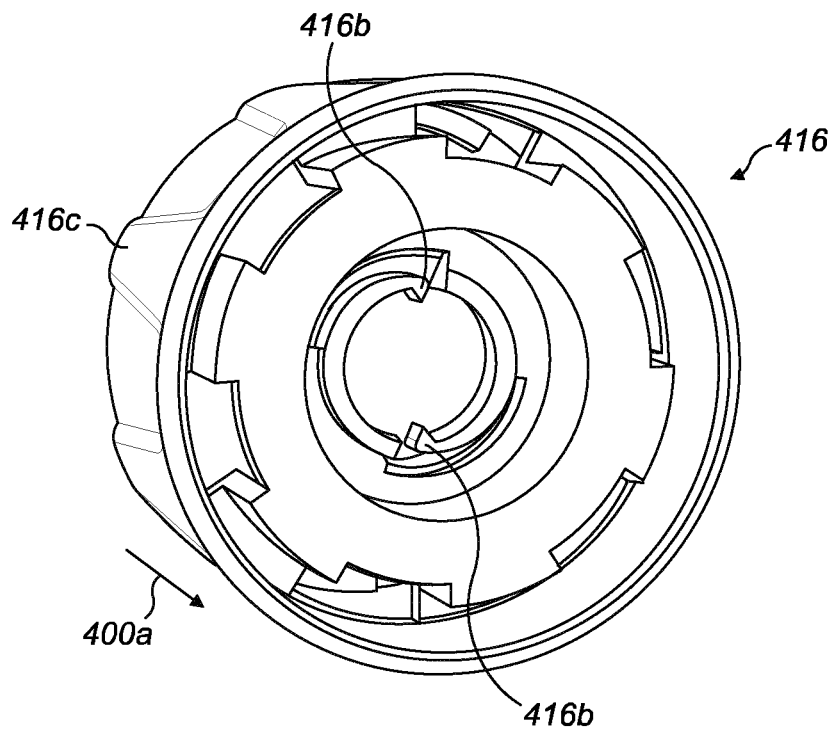
FIG. 43B is a perspective view of the dose selector, viewed from the rear of the injection device.

The dose selector 416 shown in FIGS. 43A and 43B includes a set of axially-extending splines 416a viewable from the front of the dose selector 416. These splines are involved in the disengagement of a hold ratchet arrangement. Viewable from the rear of the dose selector 416 are two ratchet pawls 416b, spaced 180 degrees apart. The ratchet pawls 416b are part of an over-torque feature. An external surface of the dose selector 416 is provided with a pattern of grip formations 416c to increase friction and to visually indicate to a user where to grip the injection device 400 in order to set the dose.

Figure 44A:
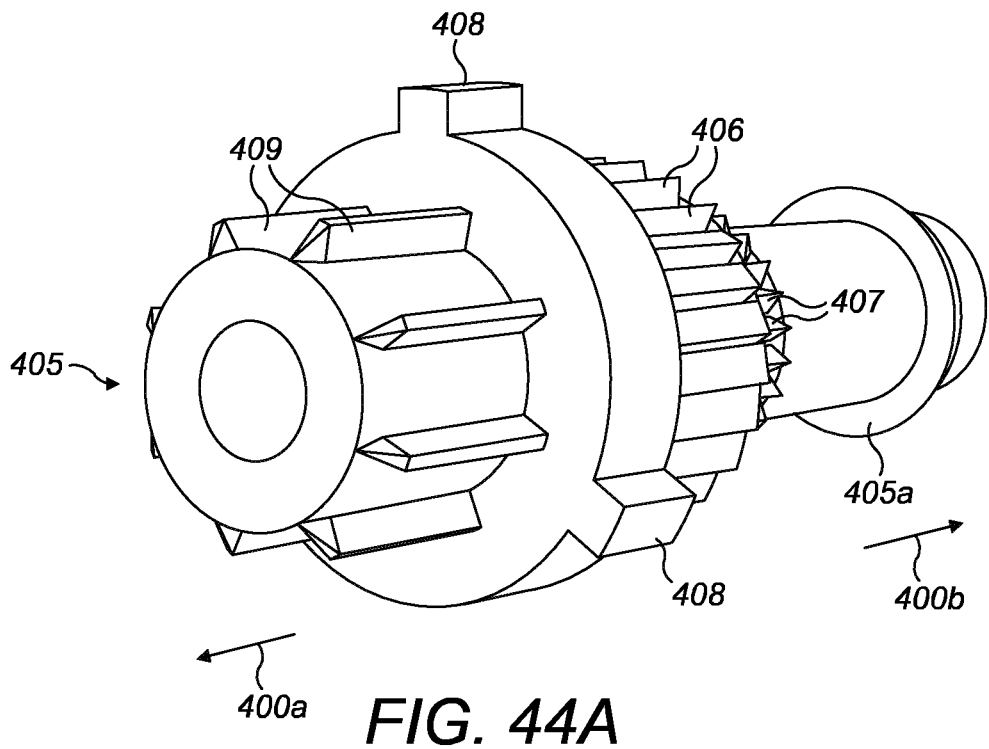
FIG. 44A is a perspective view of the drive plate, viewed from the front of the injection device.
Figure 44B:
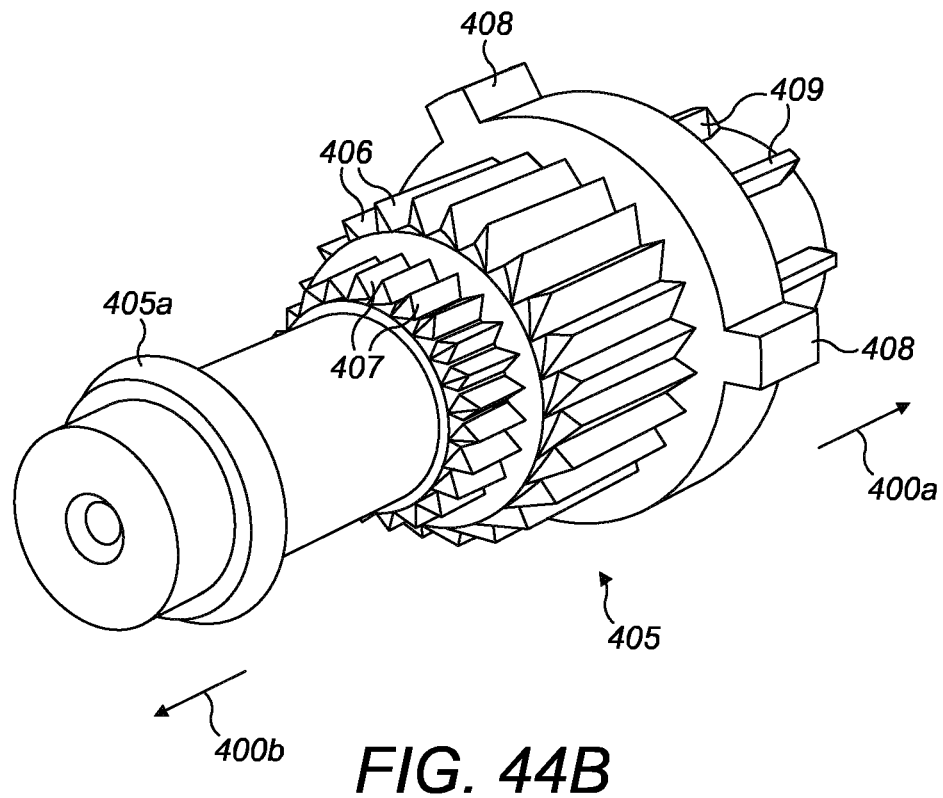
FIG. 44B is a perspective view of the drive plate, viewed from the rear of the injection device.

FIGS. 44A and 44B show the drive plate 405. The drive plate 405 includes a flange 405a for connecting the drive plate 405 to the dose button 430. Arranged axially along the drive plate 405 are four sets of splines. A first set of splines 406 forms part of the hold ratchet arrangement. Located axially rearwardly of the first set of splines 406 (i.e. towards the rear end 400b of the injection device 400) is a second set of splines 407. The second set of splines 407 has a smaller maximum diameter than the first set of splines 406.

At a region of the drive plate 405 having a maximum outer diameter is located a third set of three widely and equally-spaced splines 408 which are capable of engaging the drive sleeve 439.

At a front end of the drive plate 405 (i.e. towards the front end 400a of the injection device 400) is located a fourth set of splines 409 which are capable of engaging the drive shaft 440.

Figure 45A:
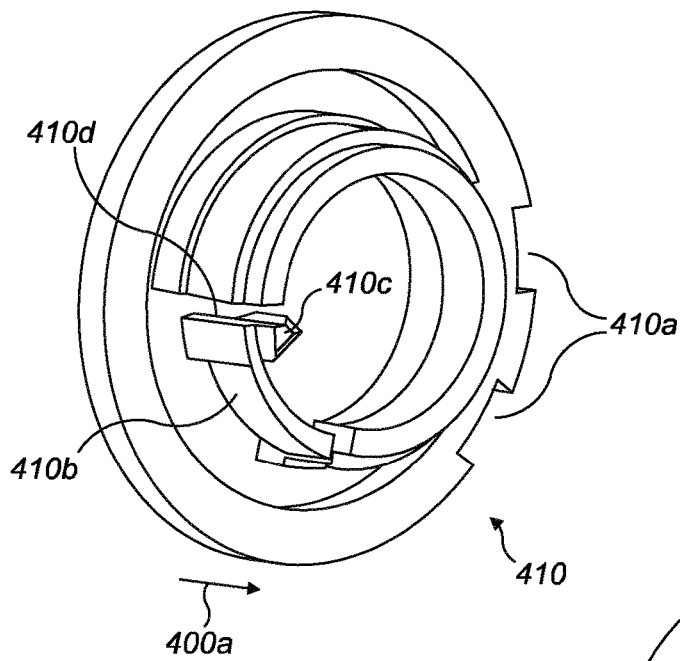
FIG. 45A is a perspective view of the ratchet ring, viewed from the front of the injection device.
Figure 45B:
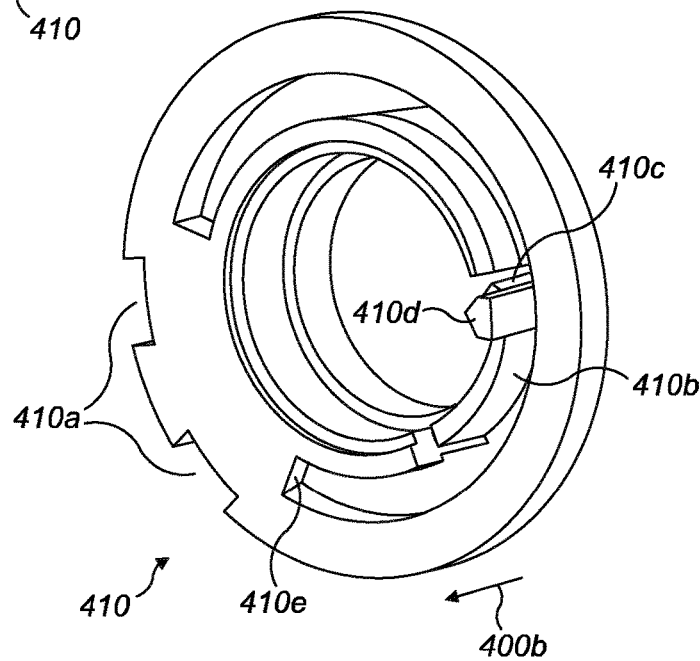
FIG. 45B is a perspective view of the ratchet ring, viewed from the rear of the injection device.
Figure 45C:
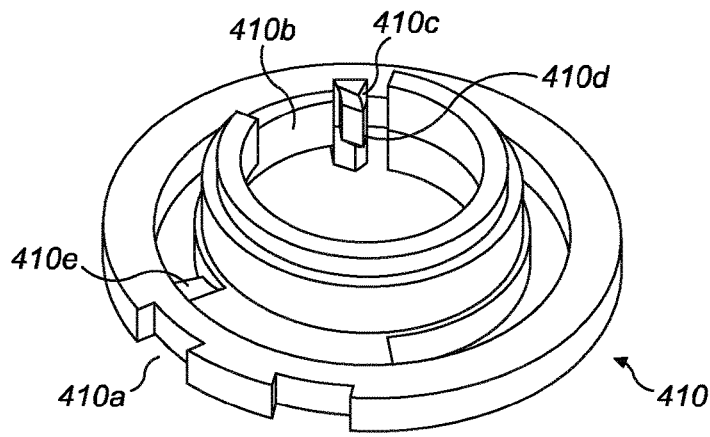
FIG. 45C is another perspective view of the ratchet ring.
Figure 46:
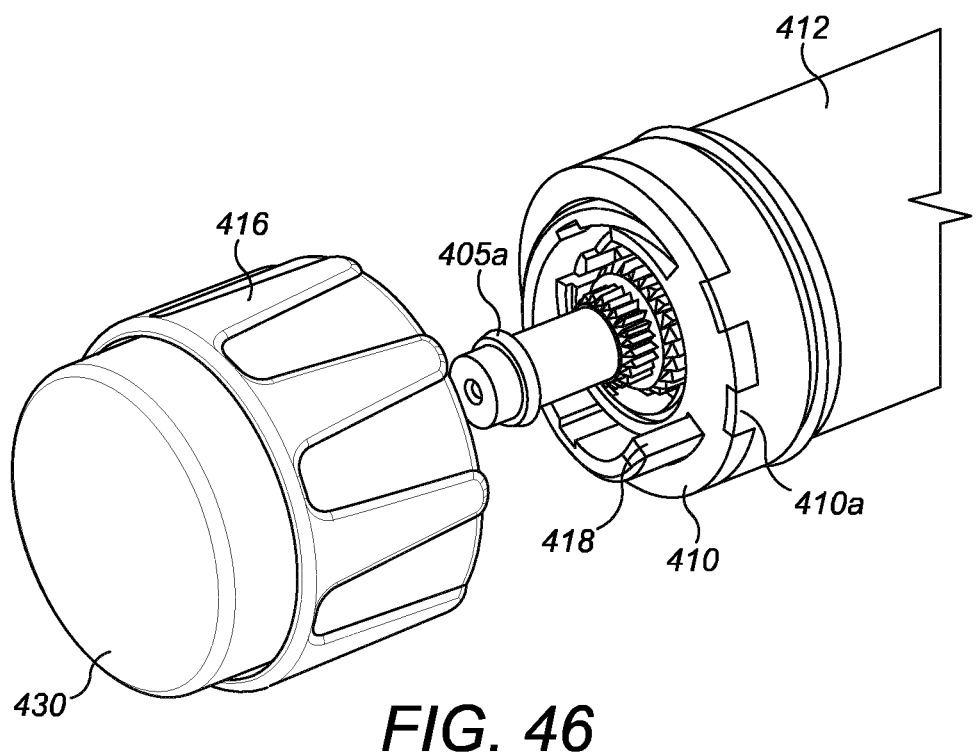
FIG. 46 is a perspective, partly-exploded view of the rear of the injection device.
Figure 47:
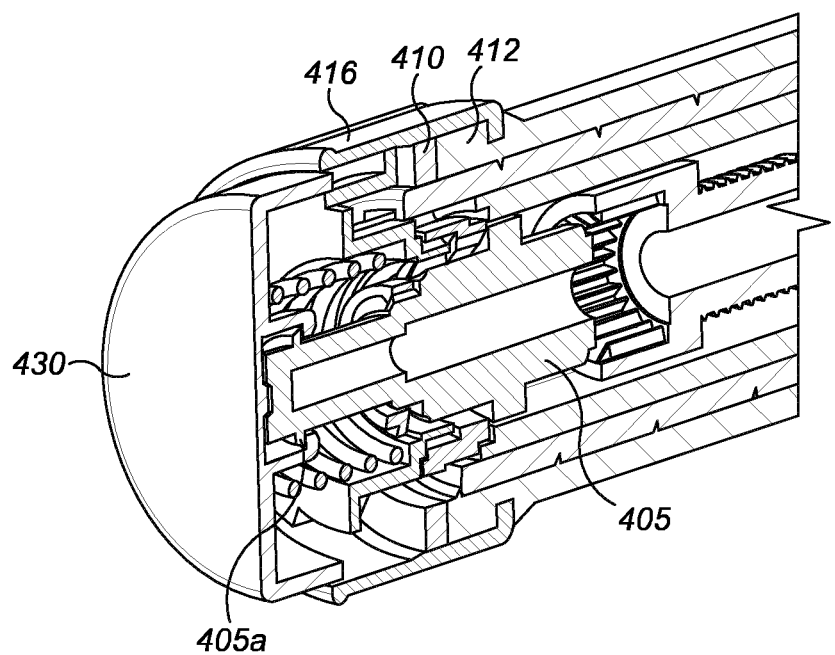
FIG. 47 is a cross-sectional view of the FIG. 46 components assembled together.

FIGS. 45A-45C show the ratchet ring 410. The ratchet ring 410 includes two notches 410a which engage corresponding formations on the housing 412 to lock the ratchet ring 410 axially and rotationally with respect to the housing 412 (FIG. 46). In an alternative embodiment the ratchet ring 410 could be formed as an integral part of the housing 412. As shown in FIG. 47, the ratchet ring 410 is held or arranged between or adjacent to the housing 412 and the dose selector 416. The ratchet ring 410 includes a hard rotary endstop 410e for the number sleeve 418.

The ratchet ring 410 includes a flexible ratchet arm 410b, at the end of which is a ratchet component in the form of two adjacent ratchet pawls 410c, 410d. The ratchet pawls 410c, 410d have different depths and/or angled surfaces so that, when the dose setting mechanism is assembled together, the ratchet pawl 410c is able to engage the first set of splines 406 on the drive plate 405 and the ratchet pawl 410d is able to engage the splines 416a on the dose selector 416.

Figure 50:
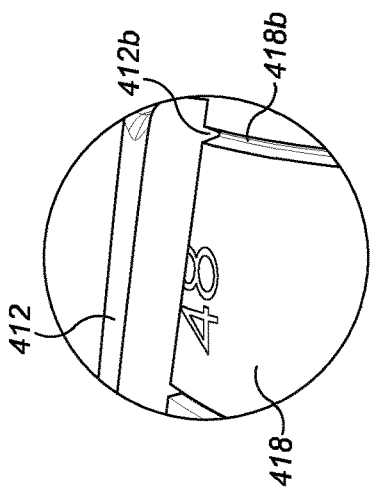
FIG. 50 is a perspective view of the number sleeve and housing assembled together.
Figure 49:
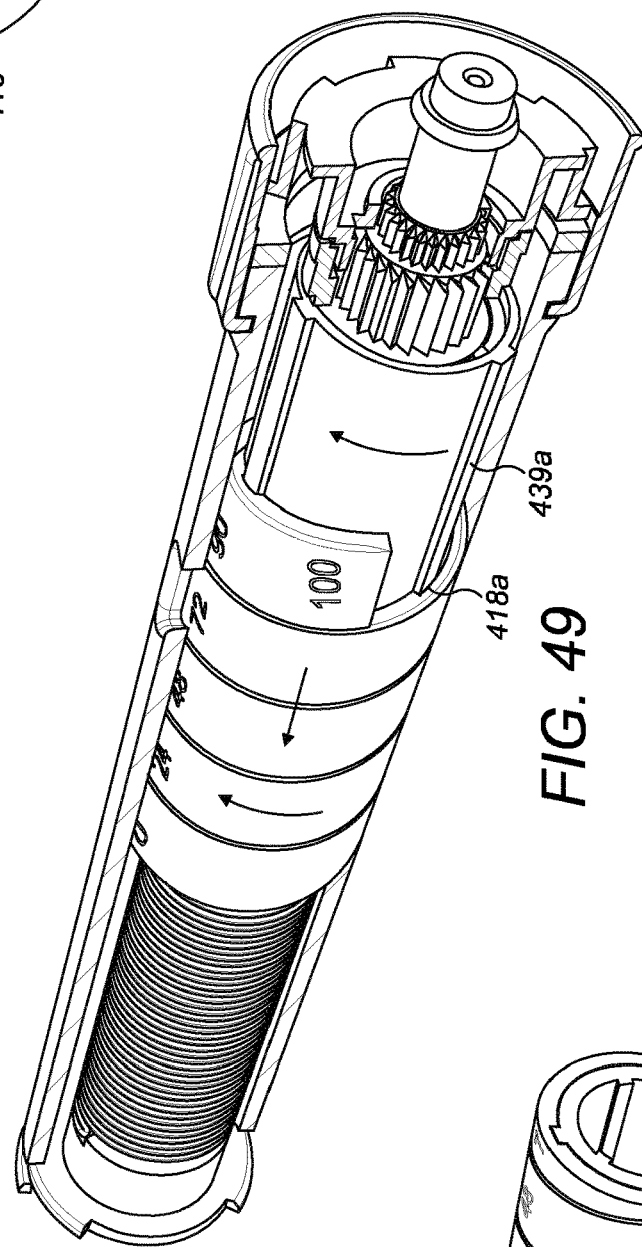
FIG. 49 is a perspective view, partly in cross-section, showing selected components of the injection device including the drive sleeve and number sleeve assembled together.
Figure 48:
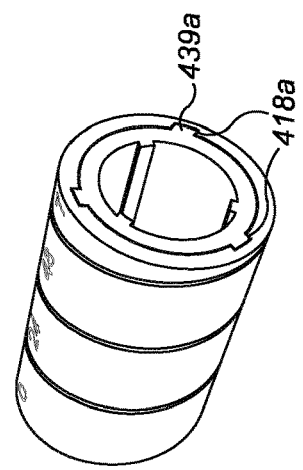
FIG. 48 is a perspective view of the drive sleeve and number sleeve assembled together.

Referring to FIGS. 48-50, the drive sleeve 439 has three equally spaced longitudinally extending external splines 439a which engage in longitudinal grooves 418a on an internal surface of the number sleeve 418. The number sleeve 418 can therefore move axially with respect to the drive sleeve 439 but is rotationally locked thereto.

An external surface of the number sleeve 418 has a helical groove 418b which engages with a thread 412b on an internal surface of the housing 412. The number sleeve 418 can therefore rotate with respect to the housing 412, guided by the thread 412b.

FIGS. 51A and 51B show an exploded view and an assembled view of the dose selector, ratchet ring and drive plate, viewed from the rear of the injection device.

FIGS. 52A and 52B are an exploded view and an assembled view of the dose selector, ratchet ring and drive plate, viewed from the front of the injection device.

The operation of the respective features of the injection device 400 will now be described in more detail below.

Dose Setting—Incrementing the Dose

Figure 53A:
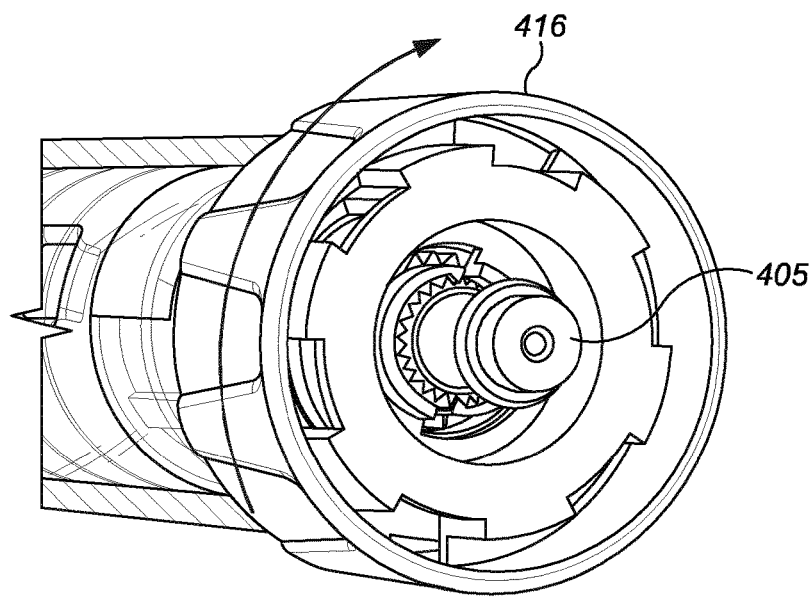
FIGS. 53A-53C, 54A and 54B illustrate incrementing the dose.
Figure 53B:
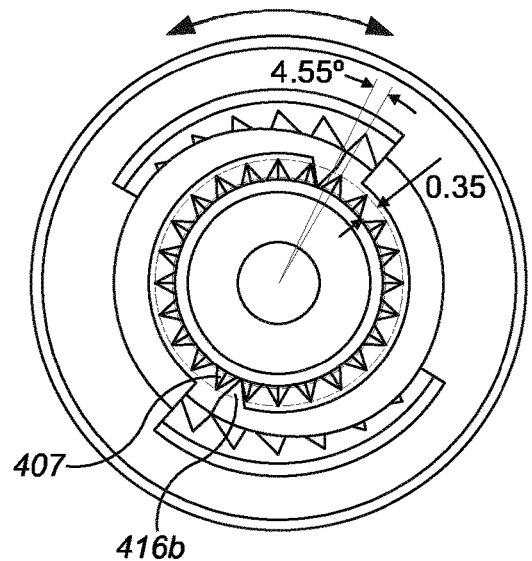
Figure 53C:
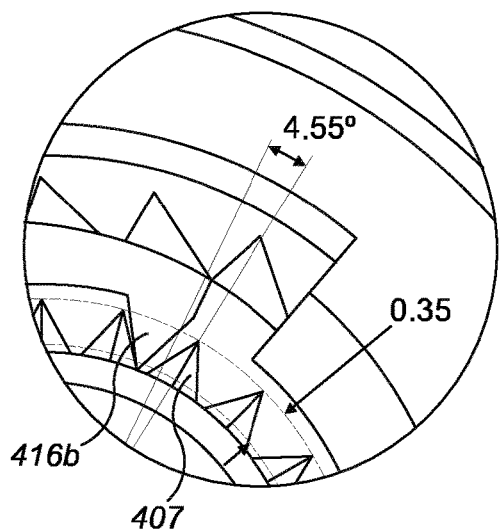

As shown in FIG. 53A, the user turns the dose selector 416 clockwise. After some degrees of unengaged rotation, preferably 3 to 7 degrees, most preferably between 4 to 5 degrees of unengaged rotation, in the embodiment 4.55° rotation, the dose selector ratchet pawl 416b starts to engage and drive the drive plate 405 clockwise via the second set of splines 407 on the drive plate 405 (FIG. 53B). The ratchet ring 410 is rotationally fixed or being integral to the housing 412 and does not rotate. The ratchet ring first pawl 410c is engaged with the drive plate splines 406 in order to provide a hold ratchet arrangement.

Figure 54A:
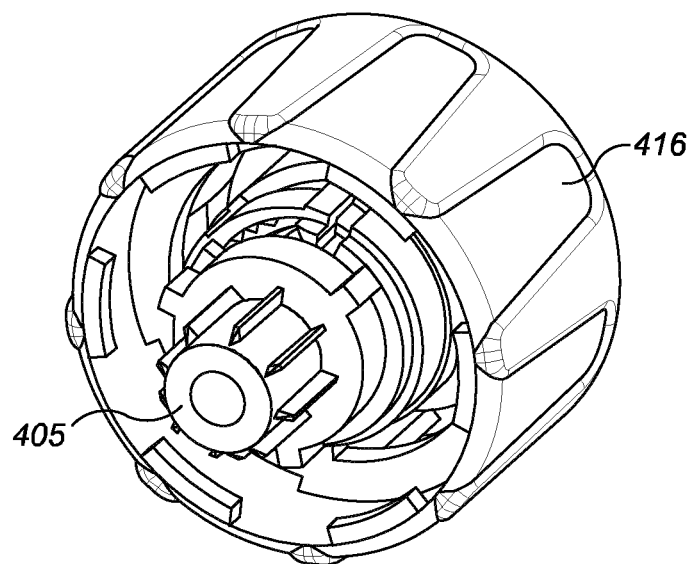
Figure 54B:
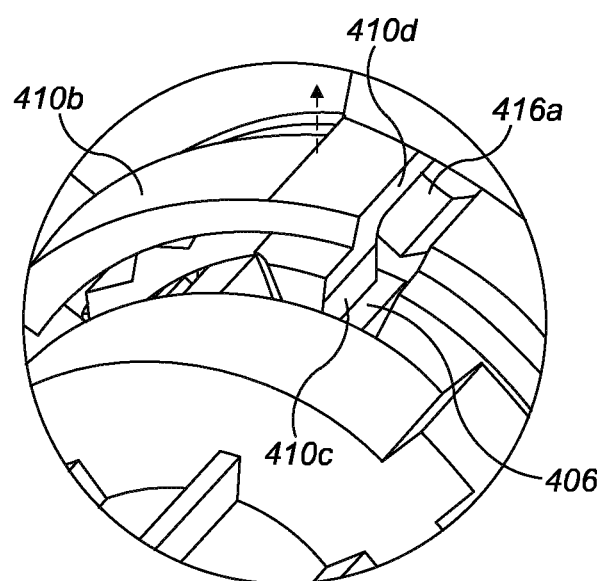
Figure 56A:
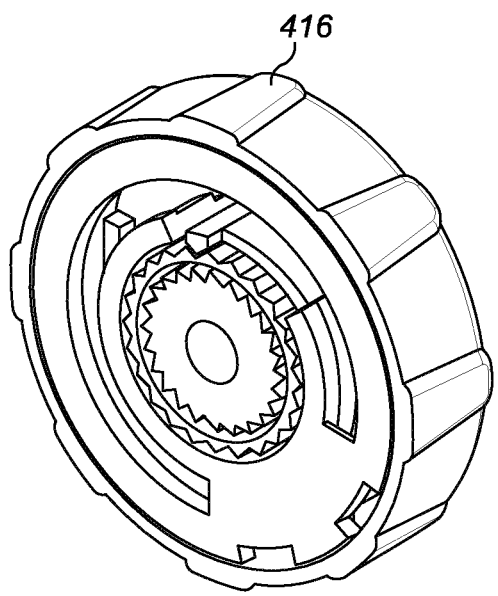
FIGS. 56A-56C are further views illustrating incrementing the dose.
Figure 56B:
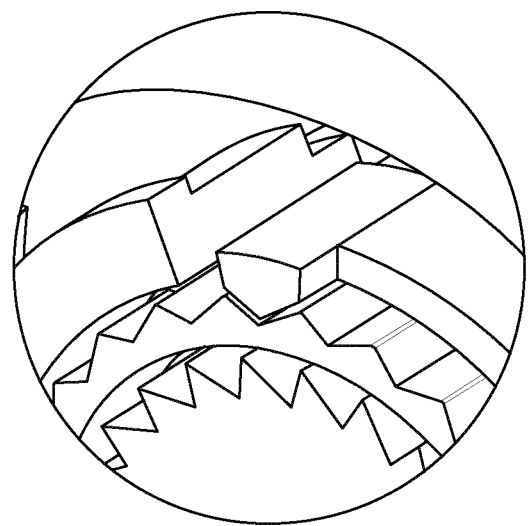
Figure 56C:
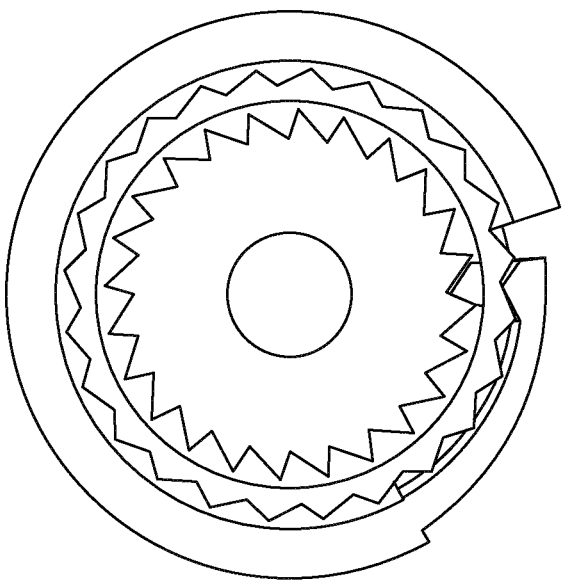
Figure 57:
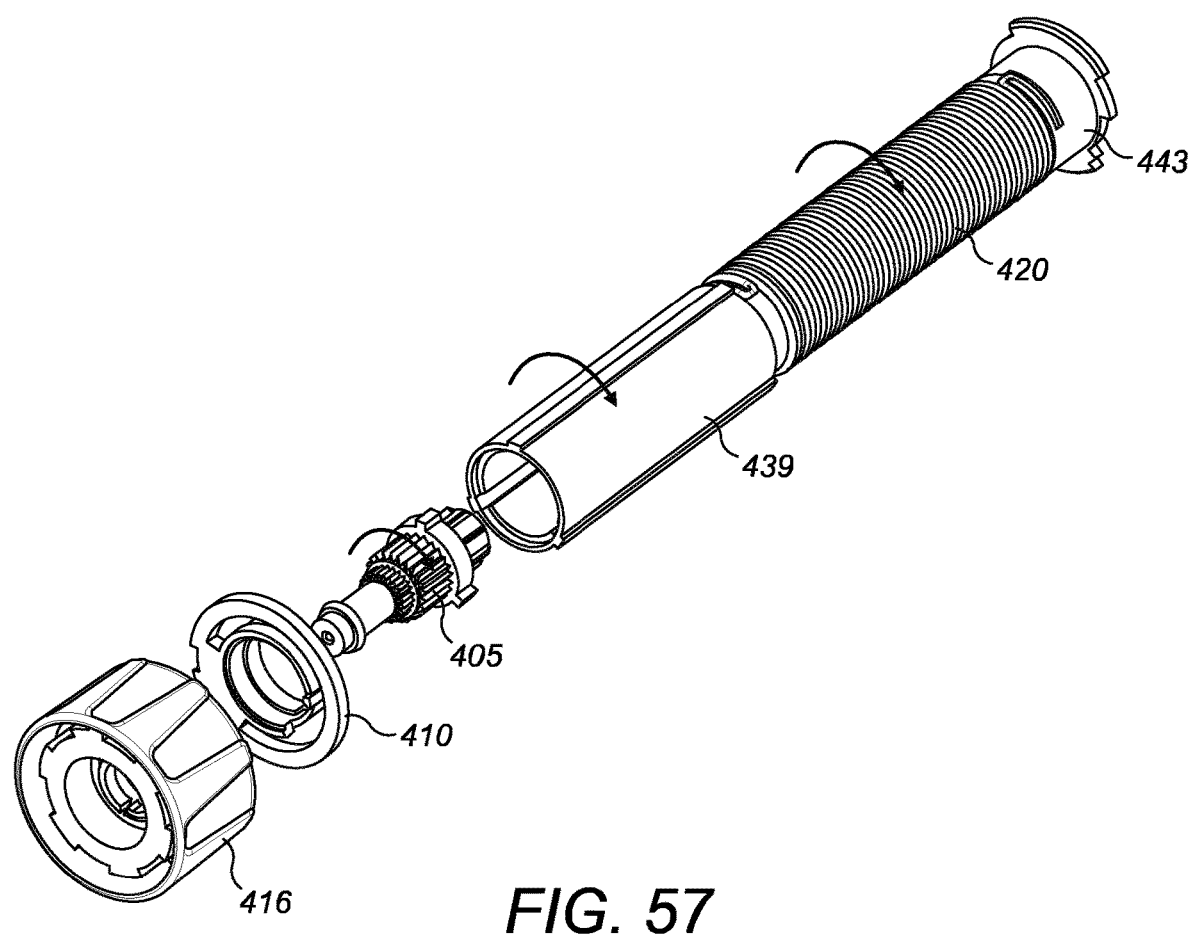
FIG. 57 is an exploded view of components involved in incrementing the dose.
Figure 58:
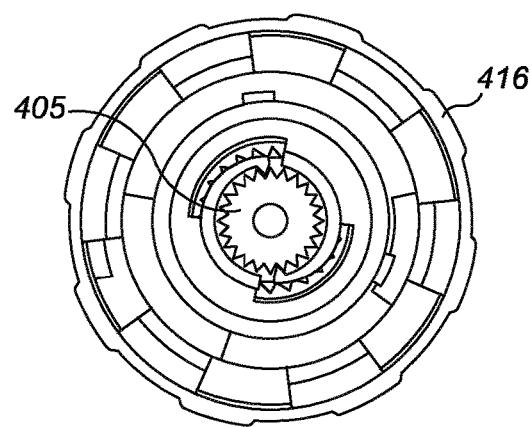
FIG. 58 is a cross-sectional view of the dose selector and dose plate.

As shown in FIG. 54B the dose selector disengagement splines 416a push against the ratchet ring second pawl 410d to disengage the hold ratchet. This is shown in more detailed steps in FIGS. 55A-55E.

Stored energy in the drive spring 420 causes the drive plate splines 406 to push against the first pawl 410c of the ratchet ring 410 hold ratchet arrangement (FIG. 55A).

As the dose selector 416 is rotated, the dose selector splines 416a start to engage the second pawl 410d of the ratchet ring 410. A first rotation of 1 to 3 degrees, in the embodiment 1.7° of rotation does not move the pawl 410d, or the ratchet arm 410b to which it is attached (FIG. 55B).

When the dose selector 416 has been rotated 5 to 12 degrees, preferably between 7 to 10 degrees, in the embodiment 8.6° (FIG. 55C), the dose selector splines 416a have pushed the pawl 410d and ratchet arm 410b radially outwardly by 0.1 mm to 1 mm, in the embodiment 0.25 mm so that the pawl 410d disengages from the dose selector splines 416a. The hold ratchet is still engaged, however, because the first ratchet ring pawl 410c is still engaged with the drive plate splines 406.

For the last part of the turn, when the dose selector 416 has been rotated 10 to 20 degrees, preferably between 13 to 17 degrees, in the embodiment 14.6° (FIG. 55D) the drive plate splines 406 push the first pawl 410c, causing the ratchet arm 410b to move radially outwardly to 0.3 mm to 1.5 mm, in the embodiment 0.41 mm. The hold ratchet temporarily disengages as the first pawl 410c disengages from the drive plate splines 406.

When the dose selector 416 has been rotated more than 10 to 20 degrees, preferably more than 13 degrees, in the embodiment 15° the ratchet arm 410b clicks over into the next splines i.e. the first pawl 410c engages the next drive plate spline 406 and the second pawl 410d engages the next dose selector spline 416a. This produces haptic feedback for the user and re-engages the hold ratchet (FIG. 55E), whereupon the process can be repeated if the dose is to be incremented further.

Figure 59:
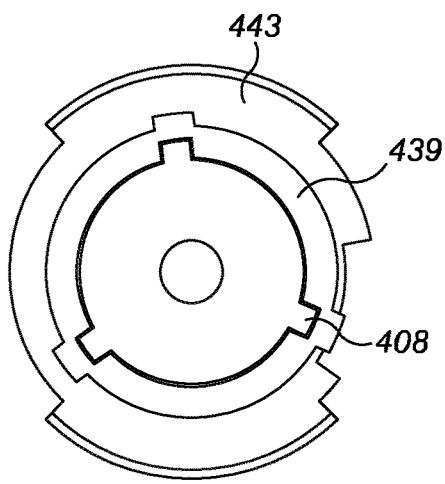
FIG. 59 is a cross-sectional view of the dose plate, drive sleeve and chassis.
Figure 60:
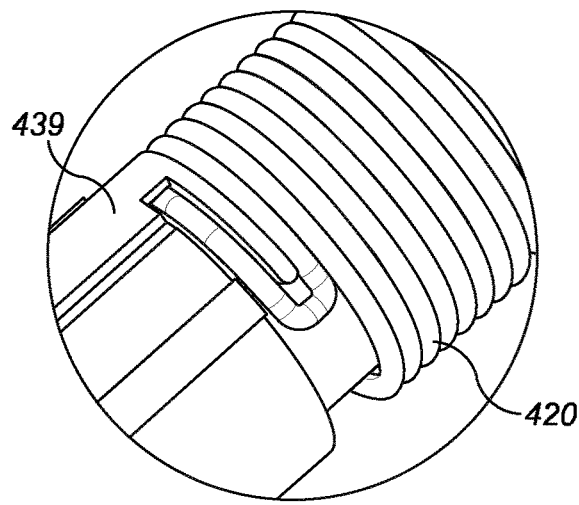
FIG. 60 shows one end of the drive spring attached to the drive sleeve.
Figure 61:
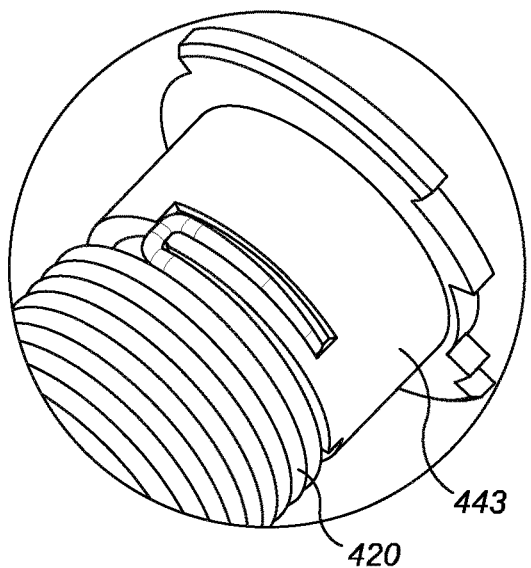
FIG. 61 shows the other end of the drive spring attached to the chassis.

As the dose selector ratchet pawl 416b drives the drive plate 405 clockwise (FIG. 58), the drive plate 405 rotates the drive sleeve 439 by virtue of the third set of drive plate splines 408 (FIG. 59). The drive sleeve 439 is locked to the drive spring 420, winding (and therefore charging) the spring 420 as the drive sleeve 439 turns (FIG. 60). The drive spring 420 is fixed at its other end to the chassis 443 (FIG. 61).

Figure 62A:
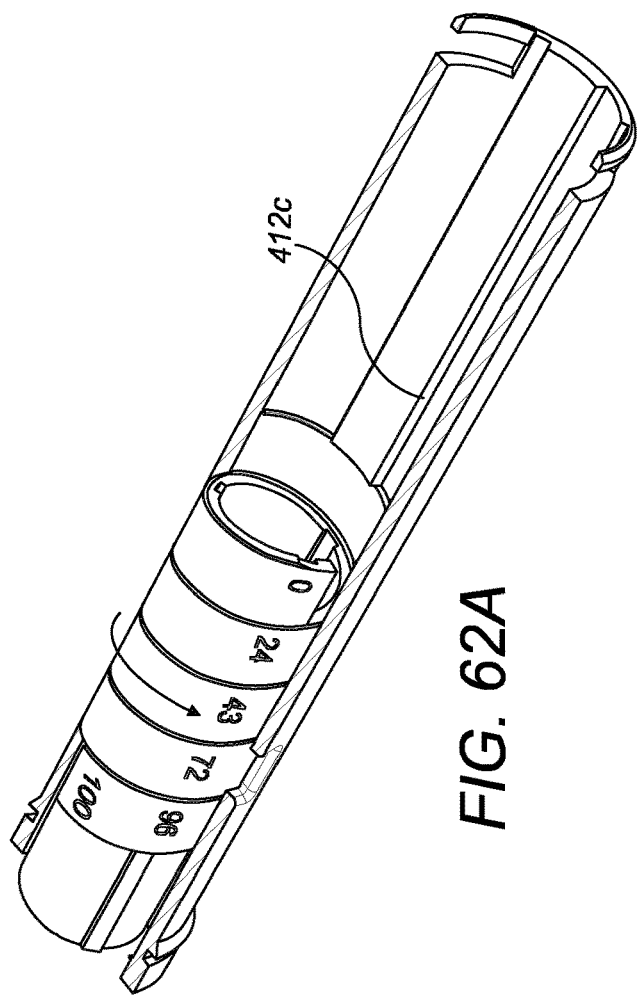
FIGS. 62A and 62B show how the number sleeve reaches the endstop in the housing.
Figure 62B:
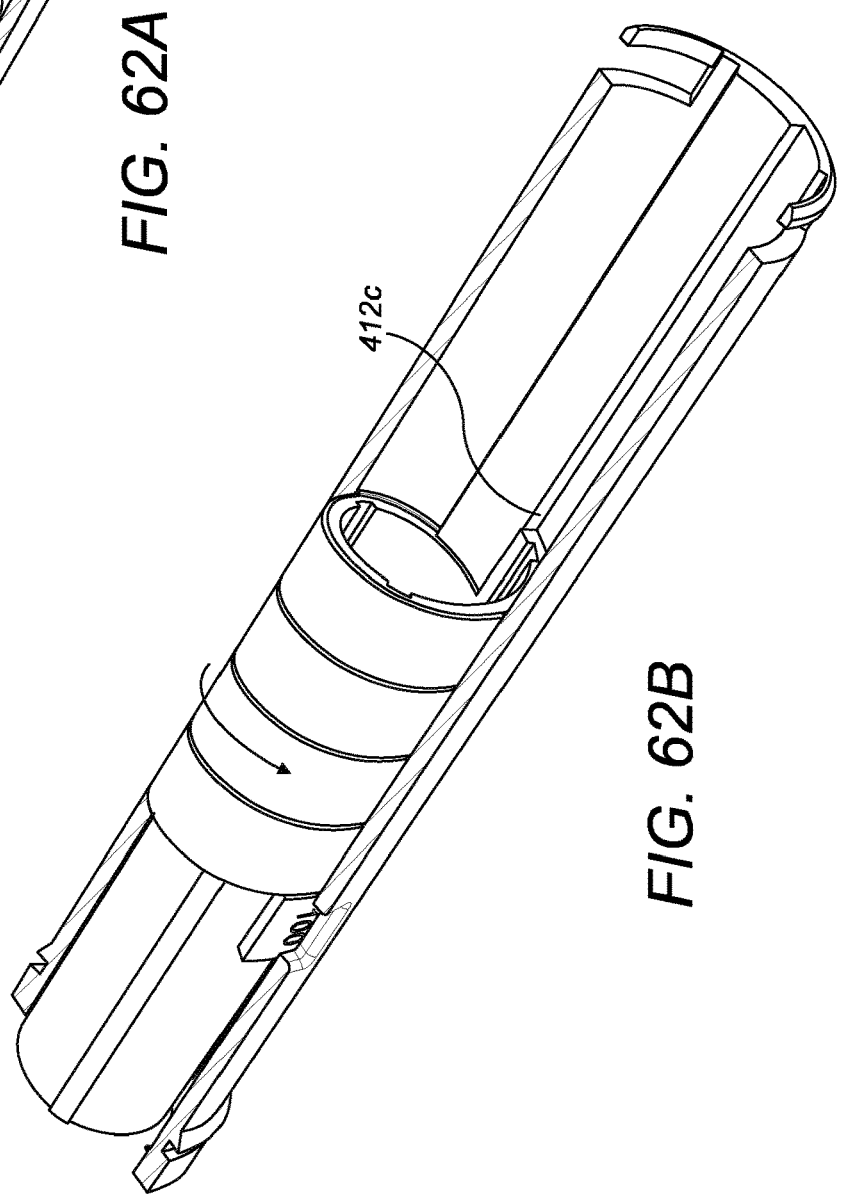

As the drive sleeve 439 turns, it turns the number sleeve 418 by virtue of the external drive sleeve splines 439a (FIG. 49). As the number sleeve 418 turns, it advances along the thread 412b on the internal surface of the housing 412 (FIG. 50). The number sleeve 418 cannot advance further than a hard endstop 412c on an internal surface of the housing 412 which prevents further rotation of the number sleeve 418 (FIG. 62B).

Dose Setting—Decrementing the Dose

Figure 63A:
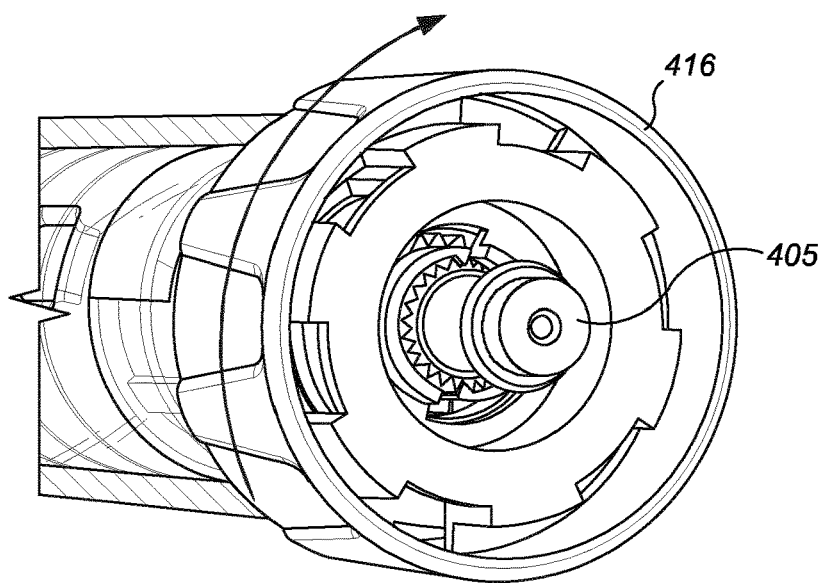
FIGS. 63A-63C, 64A and 64B illustrate decrementing the dose.
Figure 63B:
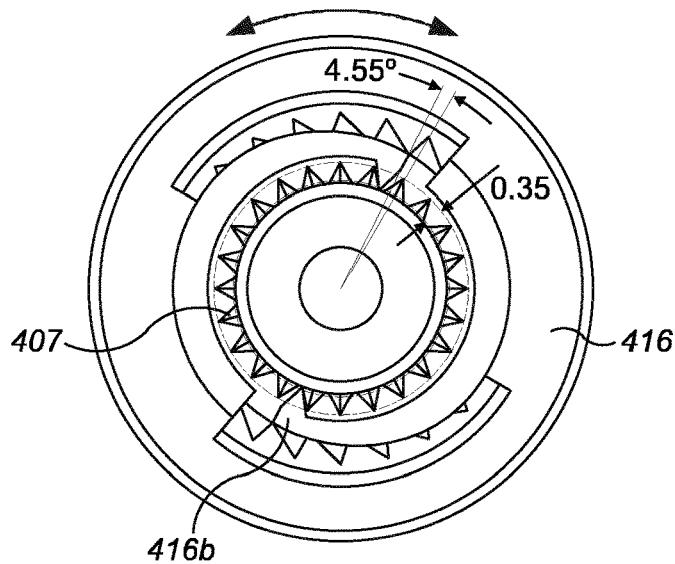
Figure 63C:
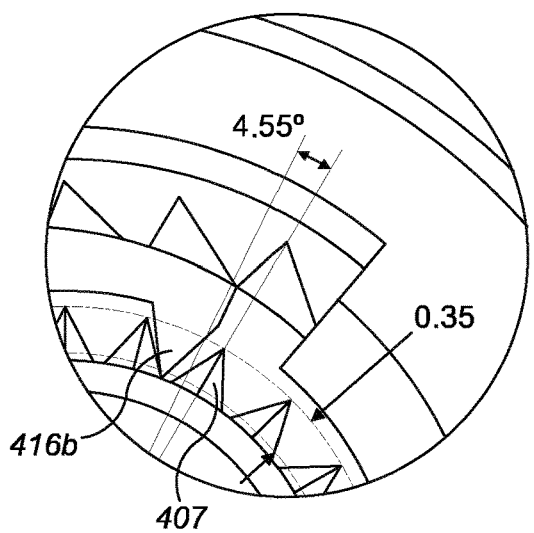
Figure 64A:
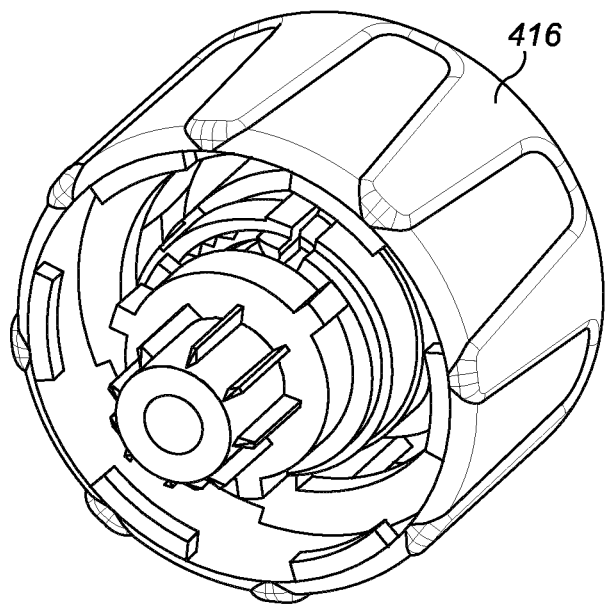
Figure 64B:
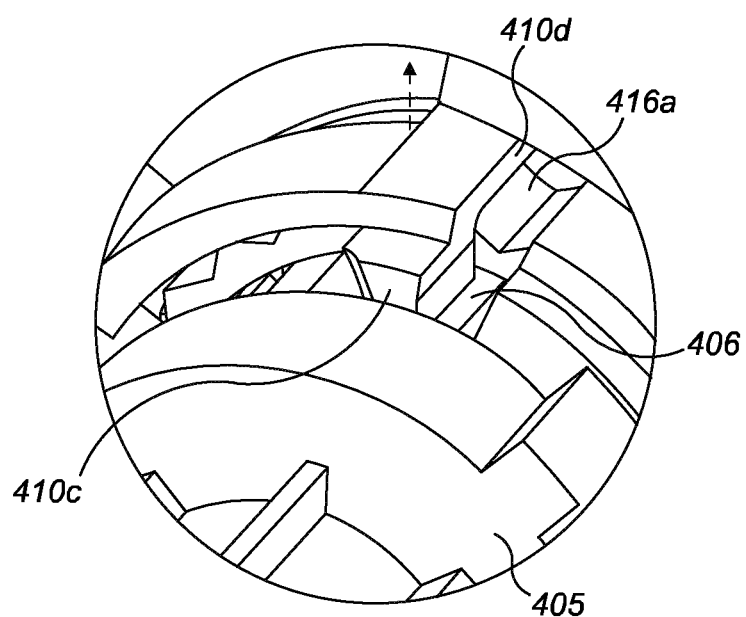

To decrement the dose, the user turns the dose selector 416 anti-clockwise (FIG. 63A). As the dose selector 416 is turned anti-clockwise, there is a small amount of lost motion such that the dose selector 416 rotates slightly, preferably between 1 to 8 degrees relative to the ratchet pawl 416b. In the specific embodiment, after 3.8° of rotation, the hold ratchet will disengage and the dose selector ratchet pawl 416b can start to drive the drive plate 405 anti-clockwise via the second set of splines 407 on the drive plate 405 (FIG. 63C). The ratchet ring 410 is rotationally fixed to the housing 412 and does not rotate.

Figure 65C:
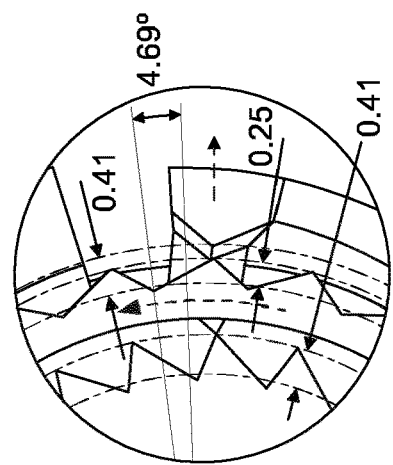
FIGS. 65A-65E illustrate the dose decrementing stages in more detail.
Figure 65B:
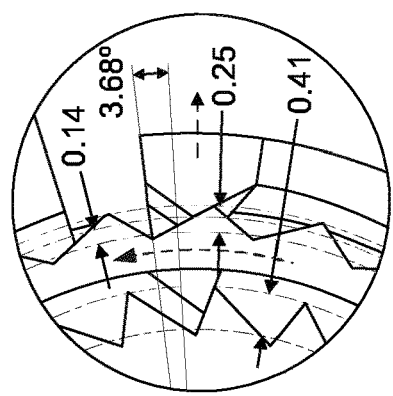
Figure 65A:
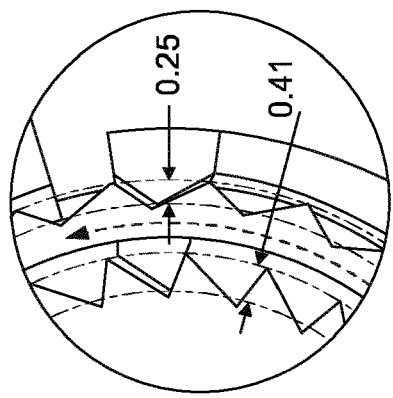

Initially, the ratchet ring first pawl 410c is engaged with the drive plate splines 406 and the ratchet ring second pawl 410d is engaged with the dose selector splines 416a so as to provide the hold ratchet arrangement (FIG. 65A). The splines 406, 416a are pushing against the pawls 410c, 410d as a result of the stored energy in the drive spring 420.

As the dose selector 416 is turned anti-clockwise, the first 1 to 5 degrees, in the embodiment 3.7° of rotation pushes the ratchet arm 410b 0.1 mm to 0.5 mm in the specific embodiment 0.14 mm radially outwardly (FIG. 65B).

After 3 to 6 degrees, in the embodiment 3.7° of rotation, the drive plate 405 starts to turn with the dose selector 416, further disengaging the hold ratchet and allowing the drive plate 405 to turn (FIG. 65C).

Figure 65E:
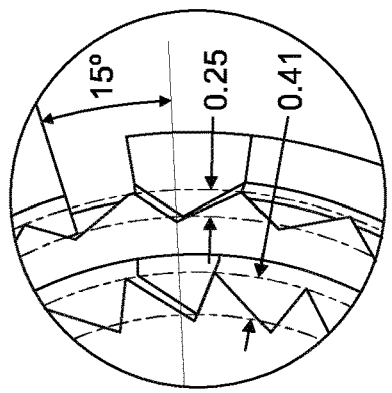
Figure 65D:
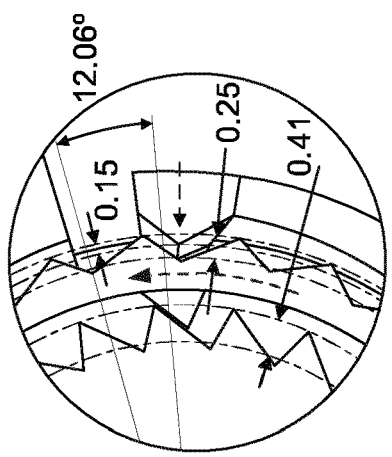
Figure 66A:
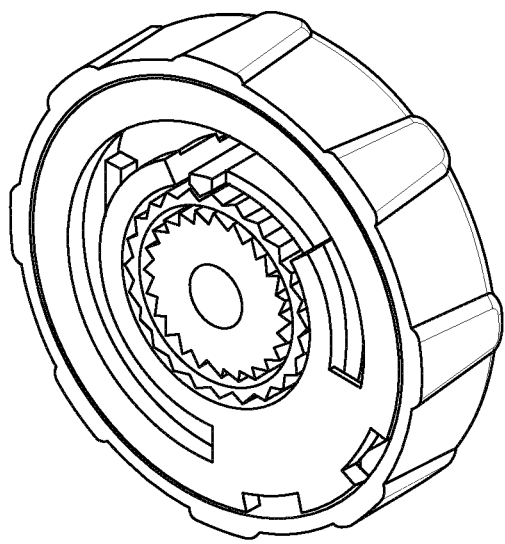
FIGS. 66A-66C are further views illustrating decrementing the dose.
Figure 66B:
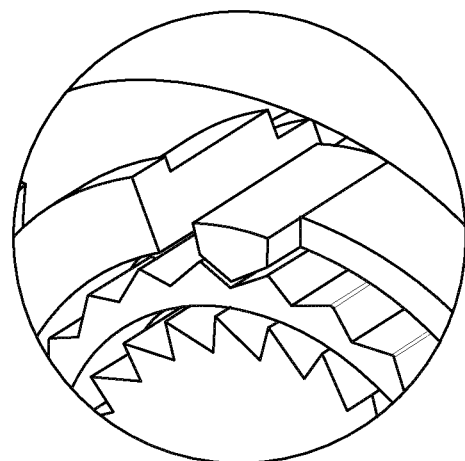
Figure 66C:
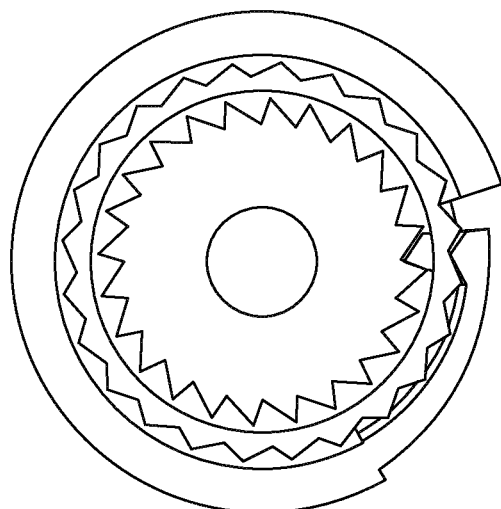

The hold ratchet then re-engages; the pawls 410c, 410d catching on the next splines 406, 416a and providing haptic feedback (FIG. 65D).

Once the hold ratchet has re-engaged, the process can be repeated if the dose is to be decremented further (FIG. 65E).

Figure 67:
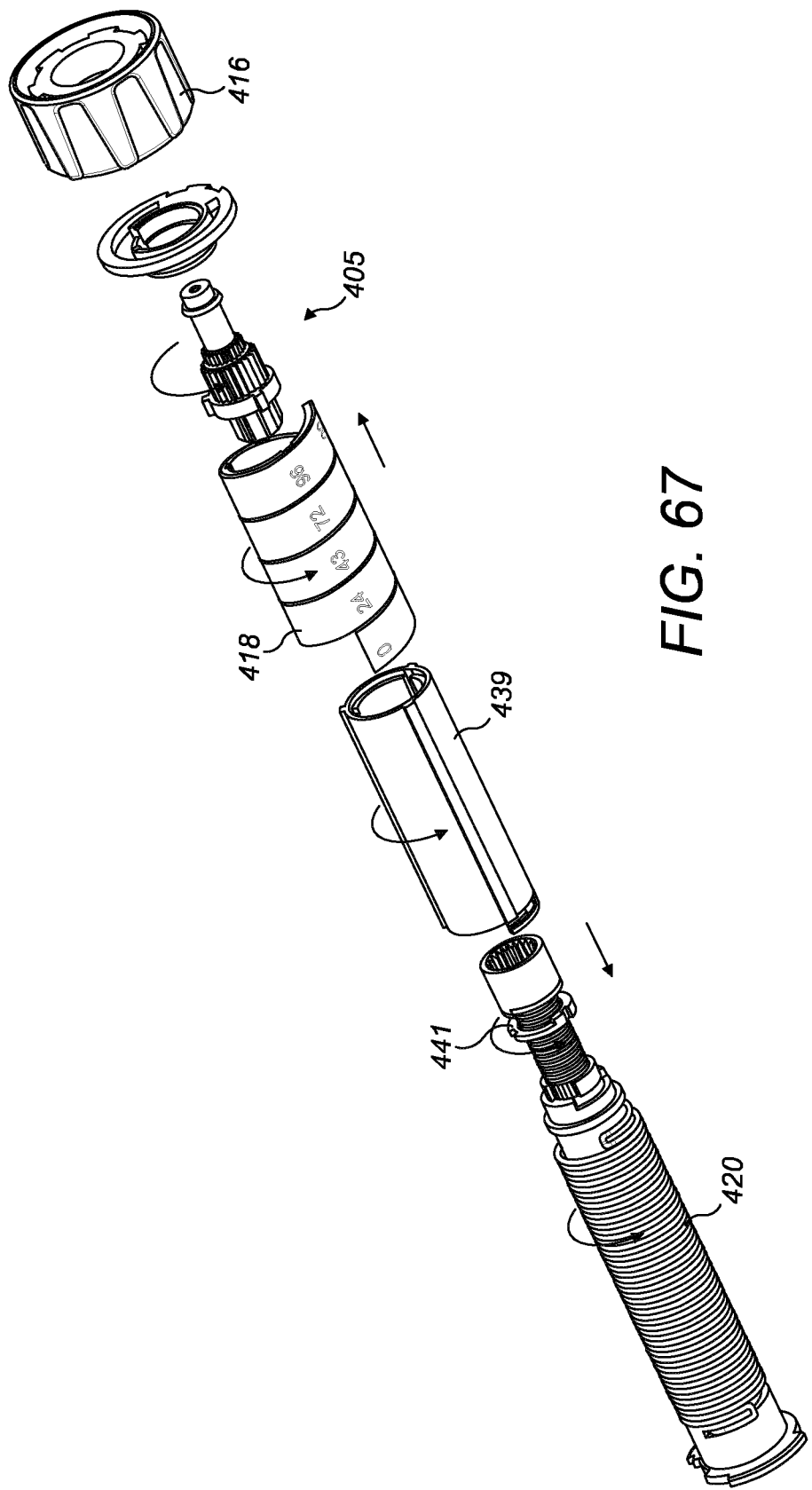
FIG. 67 is an exploded view of components involved in decrementing the dose.

The dose decrementing process is summarised in FIG. 67, in which it can be seen that the dose selector 416 turns the drive plate 405. The drive plate 405 turns the drive sleeve 439. The drive sleeve 439 turns the drive spring 420 to discharge it and also turns the last dose nut 441 and the number sleeve 418.

Figure 68A:
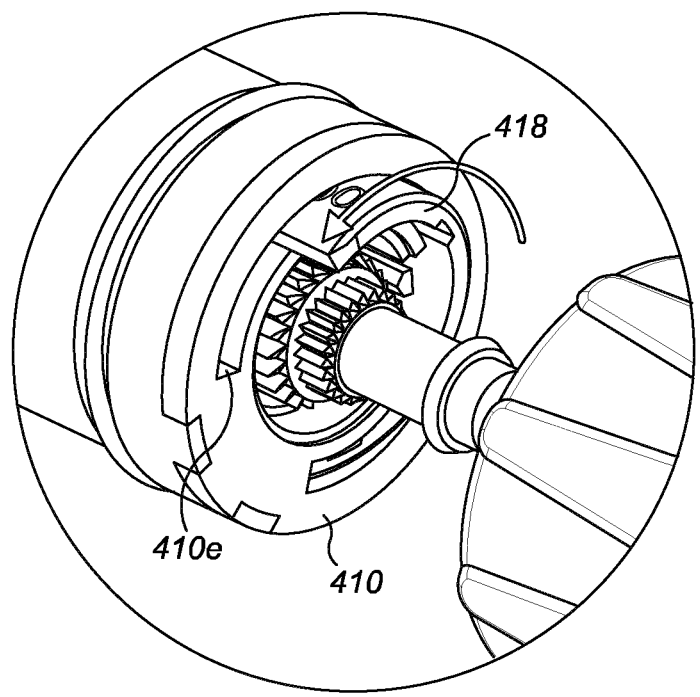
FIGS. 68A and 68B show how the number sleeve reaches the endstop in the ratchet ring.
Figure 68B:
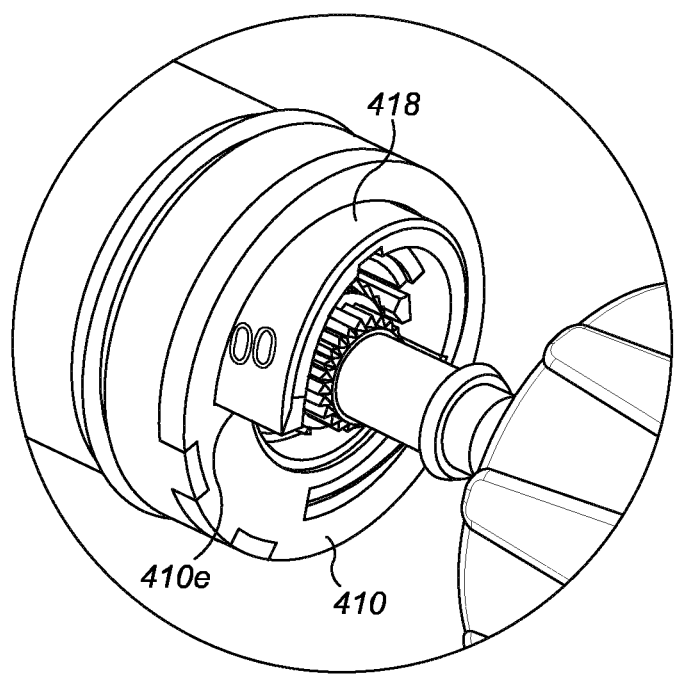

The number sleeve 418 will progress backwards, decrementing the indicated dose, until it reaches the hard rotary endstop 410e on the ratchet ring 410 (FIG. 68B).

Dose Setting—Over-Torque

Figure 69A:
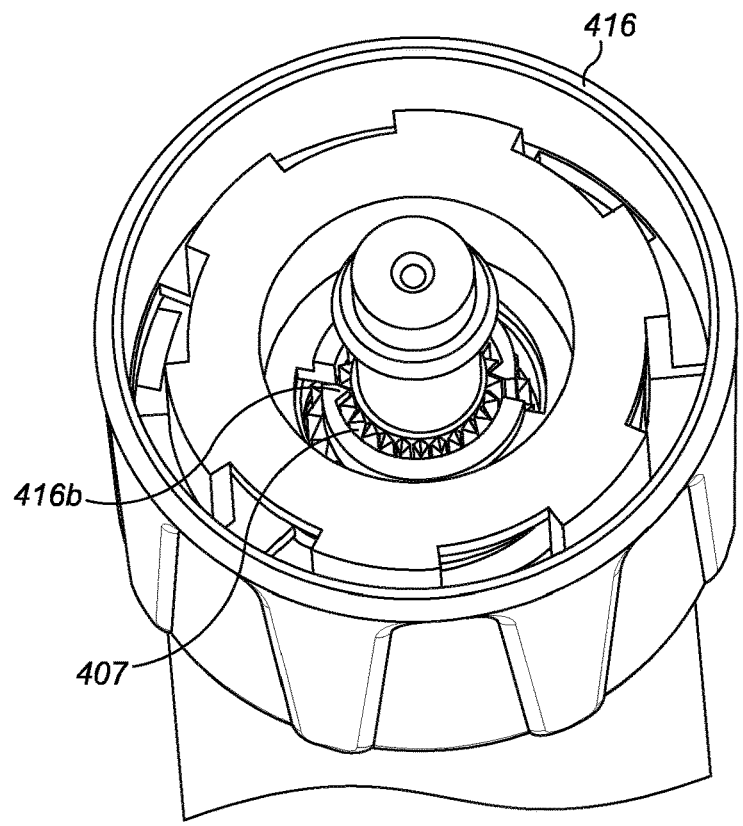
FIGS. 69A and 69B illustrate the over-torque feature.
Figure 69B:
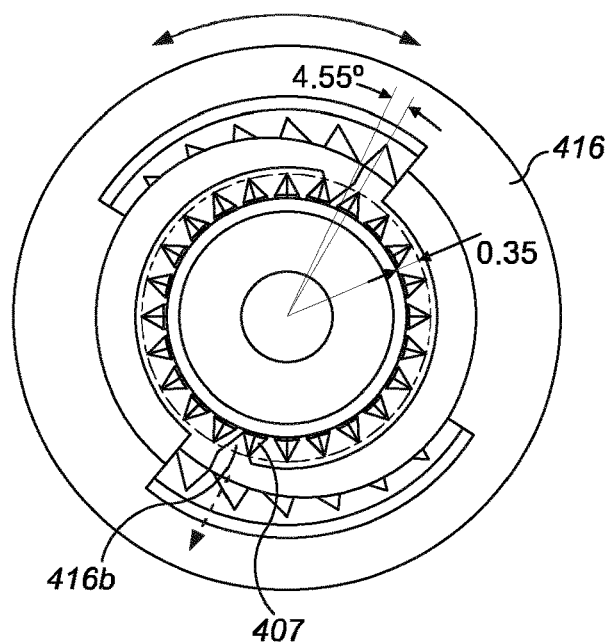

An over-torque feature is illustrated in FIGS. 69A and 69B. The over-torque feature is in the form of a ratchet arrangement is provided by the dose selector ratchet pawls 416b and the second set of splines 407 on the drive plate 405. If the number sleeve 418 has reached the endstop 410e or if the last dose protection (see below) is engaged, the over-torque feature protects components from potential damage caused by continued turning of the dose selector 416 by the user. The ratchet pawls 416b are displaced radially outwardly by 0.35 mm to disengage them from the splines 407, clicking over them to reduce the charging force transferred from the dose selector 416 to the drive spring 420. The over-torque for actuating the over-torque protection is preferably at least 10% higher than the torque required for dialling up (incrementing) or dialling down (decrementing) the dose selector 416. The dialling up torque can be 30 to 80 Nmm, preferably less than 60 Nmm, more preferably 30 to 50 Nmm. The dialling down torque can be 20 to 60 Nmm, preferably less than 50 Nmm, more preferably 30 to 40 Nmm. The over-torque in the dialling up direction may be different to the over-torque in the dialling down direction.

Last Dose Protection

Last dose protection is provided by the last dose nut 441, as illustrated in FIGS. 70-72. As the drive sleeve 439 turns, it turns the last dose nut 441 which is splined thereto. This causes the last dose nut 441 to travel axially rearwardly along the drive shaft 440 to which it is threaded. The drive shaft 440 itself does not rotate during dose setting because it is rotationally locked to the chassis 443 via the chassis ratchet 442.

The last dose nut 441 moves axially 0.5 mm to 1 mm, preferably about 0.7 mm each turn. After 13.166 turns (representing 316 IU of medicament) the last dose nut 441 has moved sufficiently so that its endstop 441b has reached the hard rotary endstop 440a on the drive shaft 440. The last dose protection is now engaged and further incrementing of the dose is no longer possible.

Dose Delivery

Figure 73:
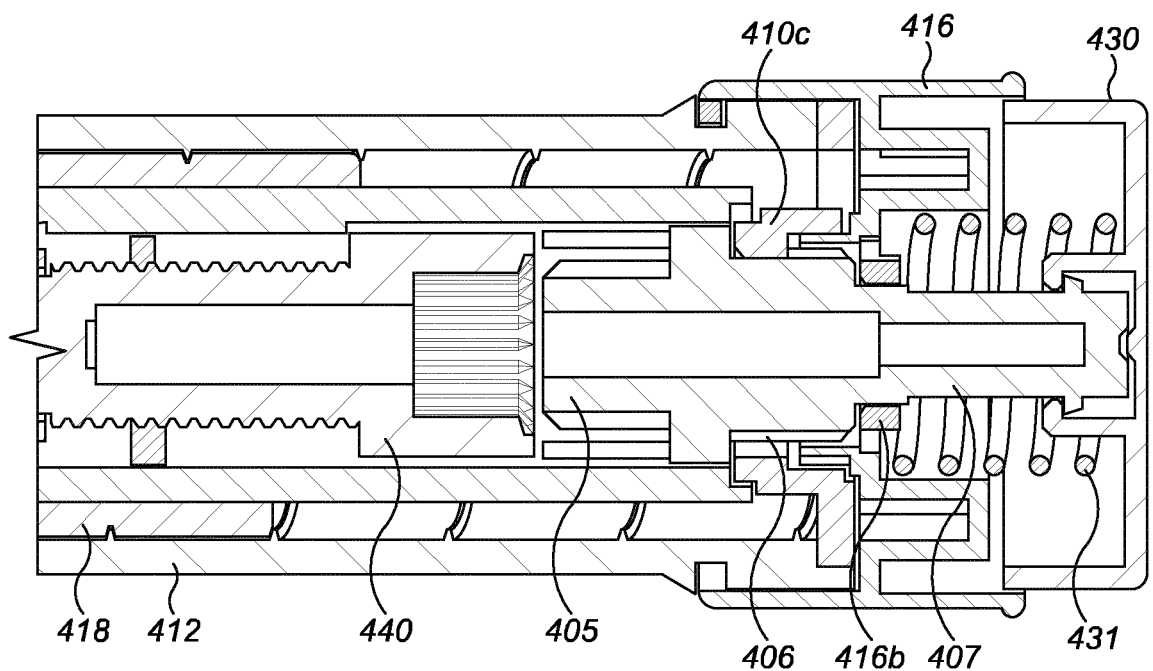
FIG. 73 shows the rear of the injection device ready to deliver a dose of medicament.

FIG. 73 shows the rear of the injection device 400 ready to deliver a dose of medicament. The dose button 430 is biased rearwardly by the dose button spring 431 and has not yet been pressed. The hold ratchet is engaged, i.e. the ratchet ring first pawl 410c is engaged with the first set of splines 406 on the drive plate 405. The over-torque feature is also engaged, i.e. the dose selector ratchet pawls 416b are engaged with the second set of splines 407 on the drive plate 405.

Figure 74A:
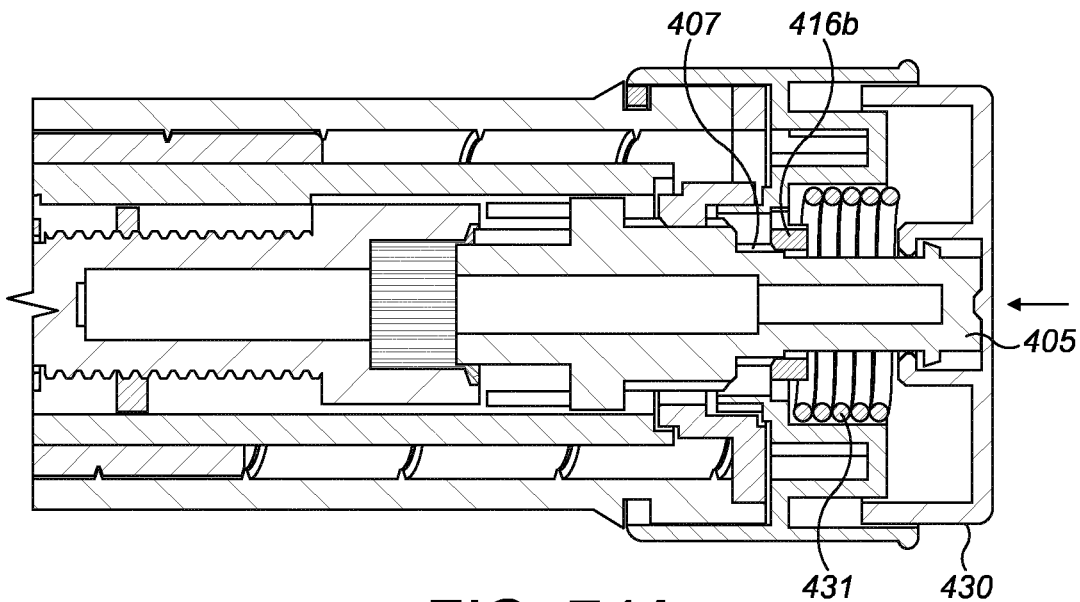
FIGS. 74A and 74B show the rear of the injection device shortly after the dose button has been pressed.
Figure 74B:
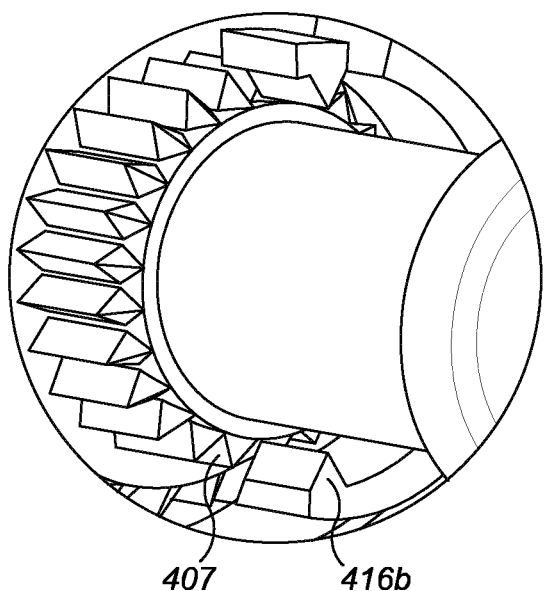

As the dose button 430 is axially depressed against the bias of the dose button spring 431 (FIG. 74A), the drive plate 405 is moved axially forward by the dose button 430 which is engaged with the rear of the drive plate 405. The forward axial movement of the drive plate 405 means that the dose selector ratchet pawls 416b (which have not moved axially) are no longer engaged with the splines 407, thus the over-torque feature is disengaged and the drive plate 405 is free of the dose selector 416 (FIG. 74B).

Figure 75A:
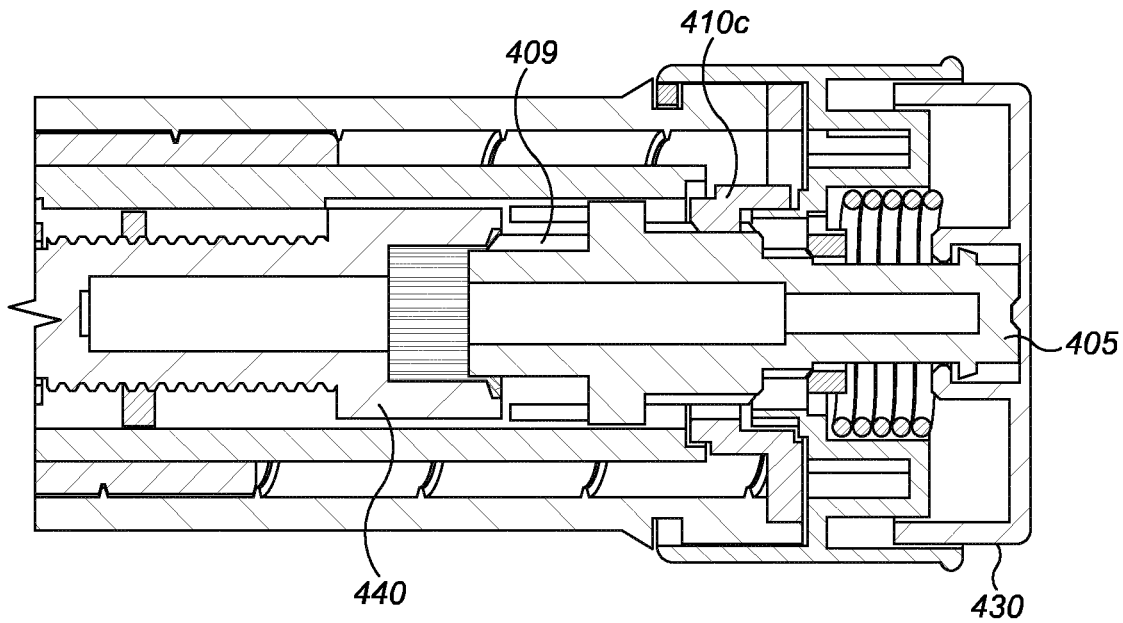
FIGS. 75A and 75B show the rear of the injection device after further pressing of the dose button, with the hold ratchet still engaged.
Figure 75B:
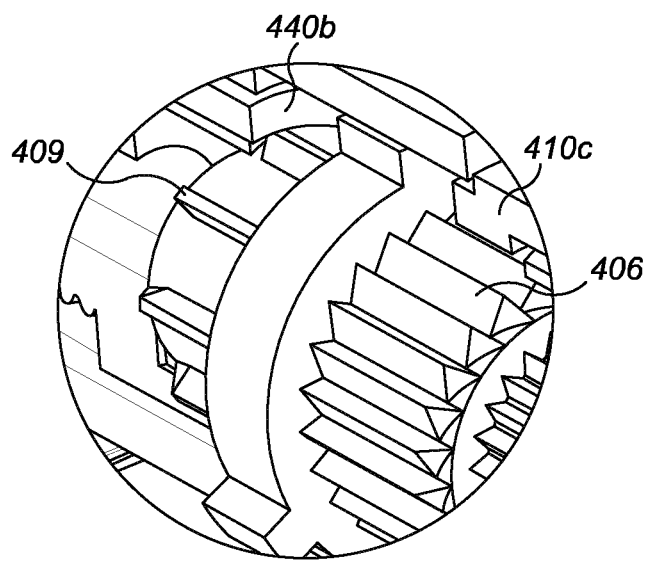

Further pressing of the dose button 430 causes continued forward axial movement of the drive plate 405. The fourth set of splines 409, at the front of the drive plate 405, begin to engage the internal splines 440b at the rear of the drive shaft 440 (FIGS. 75A and 75B). The drive plate splines 409 and drive shaft splines 440b operate together as a "drive clutch". At this point, the hold ratchet is still engaged (i.e. the ratchet ring first pawl 410c is still engaged with the first set of splines 406 on the drive plate 405) and the drive plate 405 is not yet able to rotate.

Figure 76A:
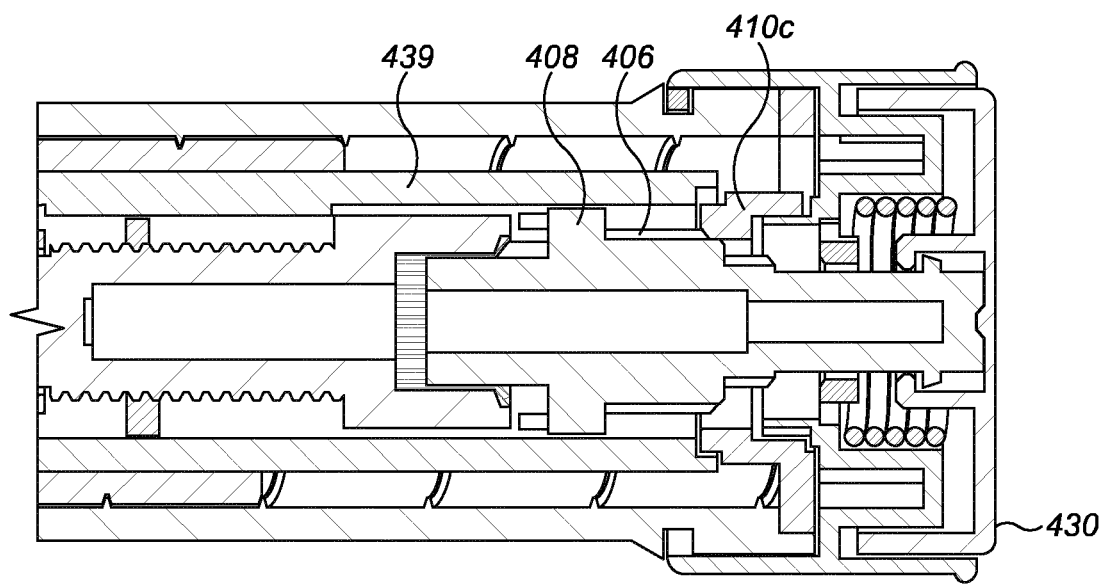
FIGS. 76A and 76B show the rear of the injection device after further pressing of the dose button, with the hold ratchet just released.
Figure 76B:
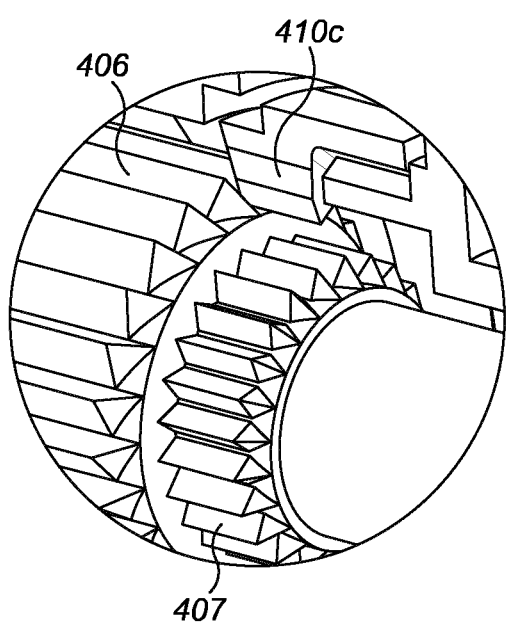

With reference to FIGS. 76A and 76B, further pressing of the dose button 430 causes continued forward axial movement of the drive plate 405. The hold ratchet is disengaged so that the drive plate splines 406 are now free of the ratchet ring pawl 410c and the drive plate 405 is free to rotate. The drive plate 405 is urged to rotate, driven by the drive sleeve 439 (FIG. 60) to which it is splined (via splines 408), the drive sleeve 439 being driven by the charged drive spring 420.

Figure 77A:
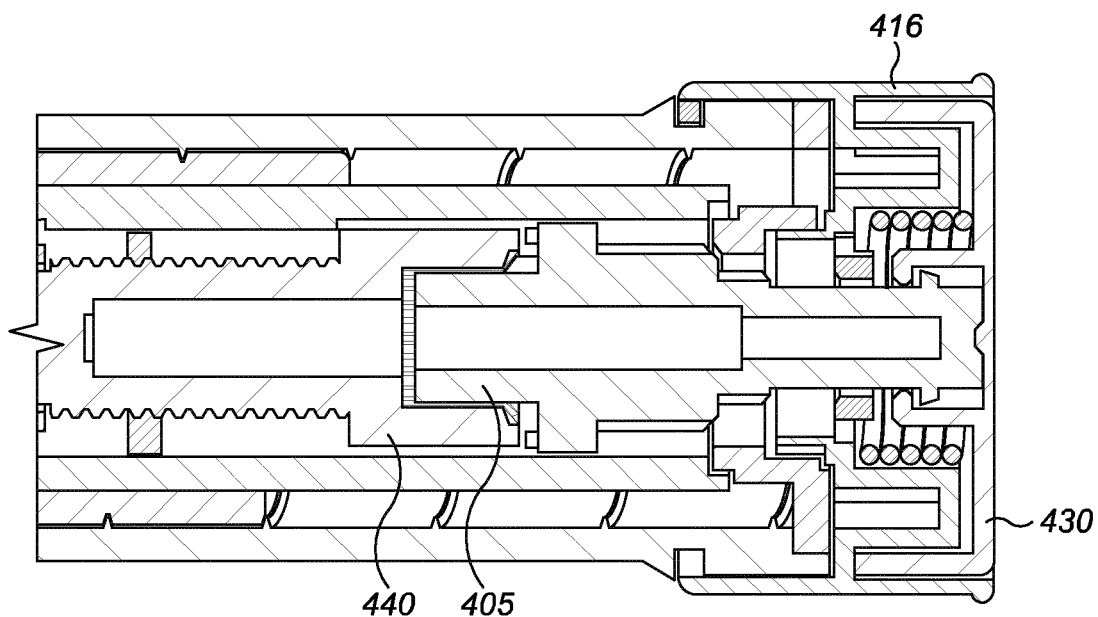
FIGS. 77A and 77B show the rear of the injection device after further pressing of the dose button, with the drive plate fully engaged with the drive shaft.
Figure 77B:
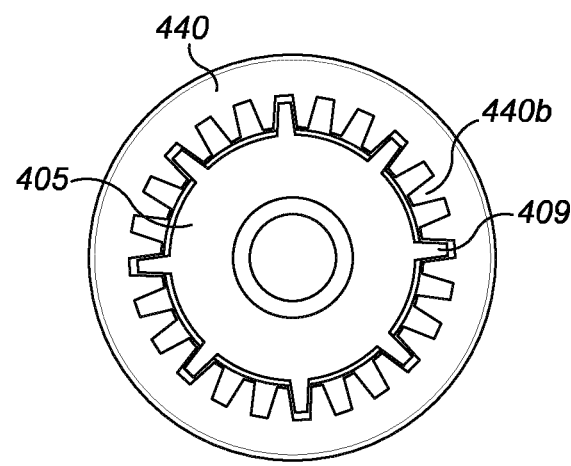

The engagement of the fourth set of drive plate splines 409 with the rear of the drive shaft 440 enables the drive shaft 440 to be driven by the spring 420 (FIG. 77B).

FIG. 77A shows the dose button 430 fully depressed, its axial travel limited by abutting the dose selector 416. The drive plate 405 and drive shaft 440 are fully engaged and able to rotate freely, driven by the drive spring 420 to deliver the desired dose of medicament.

During dose delivery, the one-way chassis ratchet 442 allows the drive shaft 440 to rotate with respect to the chassis 443, during which haptic feedback is provided to the user by the clicking of the chassis ratchet 442.

Figure 78:
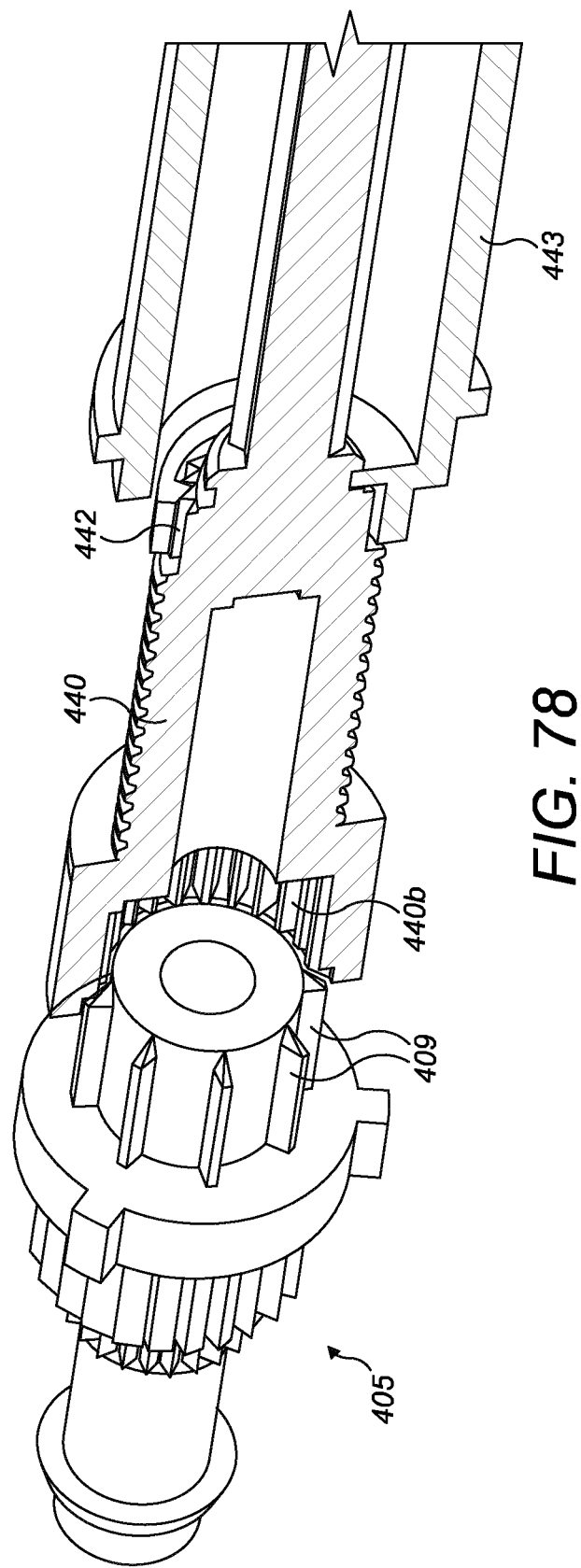
FIG. 78 is a perspective view, partly in cross-section, of the drive plate, drive shaft and chassis.

FIG. 78 shows how the fourth set of splines 409 on the drive plate 405 engage with the internal splines 440b of the drive shaft 440. The one-way chassis ratchet 442 is also visible at the rear of the chassis 443.

The relative rotational positions of the drive plate 405 and drive shaft 440 is important, to ensure the splines 409, 440b mesh smoothly (FIG. 77B). The splines 409, 440b are designed to allow up to 1 to 2 degrees of rotational displacement or play between splines 409, 440b. FIG. 79 shows typical relative positions of the hold ratchet pawl 410c and drive plate splines 406 (leftmost Figure), the chassis ratchet 442 and drive shaft 440 (centre Figure) and the drive plate splines 409 and internal drive shaft splines 440b (rightmost Figure). A 0.81° overlap does not prevent the drive plate 405 and drive shaft 440 from engaging smoothly.

FIG. 80 shows the most extreme possible relative positions of the hold ratchet pawl 410c and drive plate splines 406 (leftmost Figure), the chassis ratchet 442 and drive shaft 440 (centre Figure) and the drive plate splines 409 and internal drive shaft splines 440b (rightmost Figure). A 1.81° overlap still allows the drive plate 405 and drive shaft 440 to engage smoothly.

Dose delivery can be summarised with reference to FIG. 81. The charged drive spring 420 is fixed at one end to the drive sleeve 439, turning it anti-clockwise. The drive sleeve 439 turns the number sleeve 418 which is splined thereto, causing the number sleeve 418 to move axially backwards because it is engaged with the screw thread 412b in the housing 412 (not shown).

The drive sleeve 439 turns the drive plate 405 because of splines 408. The drive plate 405 is engaged with the drive shaft 440 via splines 409 (not visible) and so the drive shaft 440 also turns.

The last dose nut 441 turns with the drive sleeve 439 and drive shaft 440 but does not move axially with respect thereto.

As the drive shaft 440 turns, it turns the hollow plunger 444 which is rotationally locked, or keyed, thereto. The thrust nut 445 causes the screw-threaded hollow plunger 444 to advance axially forwards, pushing the plunger bearing 446 against the cartridge stopper 426 (not shown) into the cartridge 424 (not shown) to expel the dose of medicament.

Figure 82:
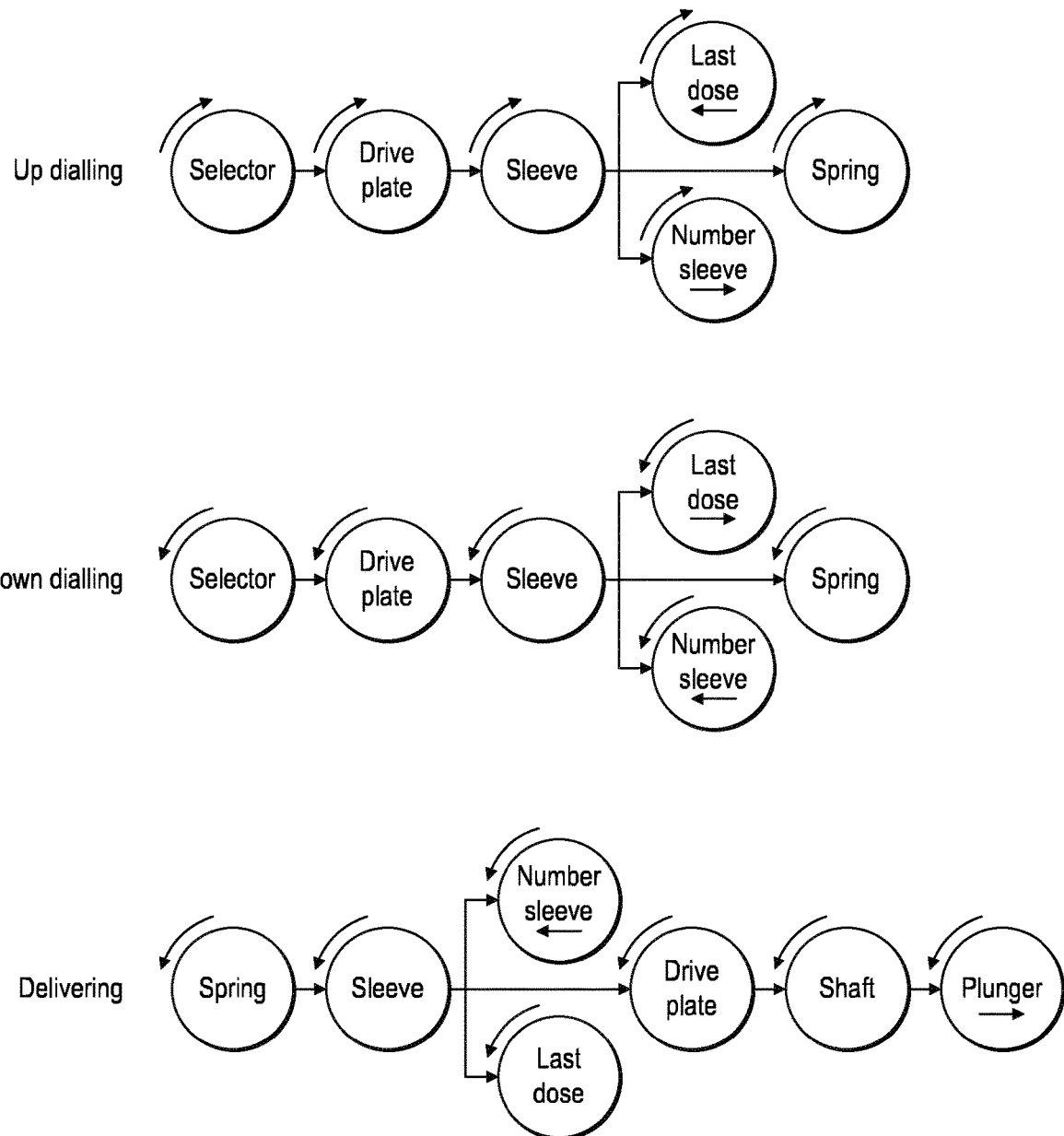
FIG. 82 summarises schematically the mechanical motion transfer of the injection device components.

FIG. 82 summarises schematically the mechanical motion transfer of the injection device components.

Figure 83:
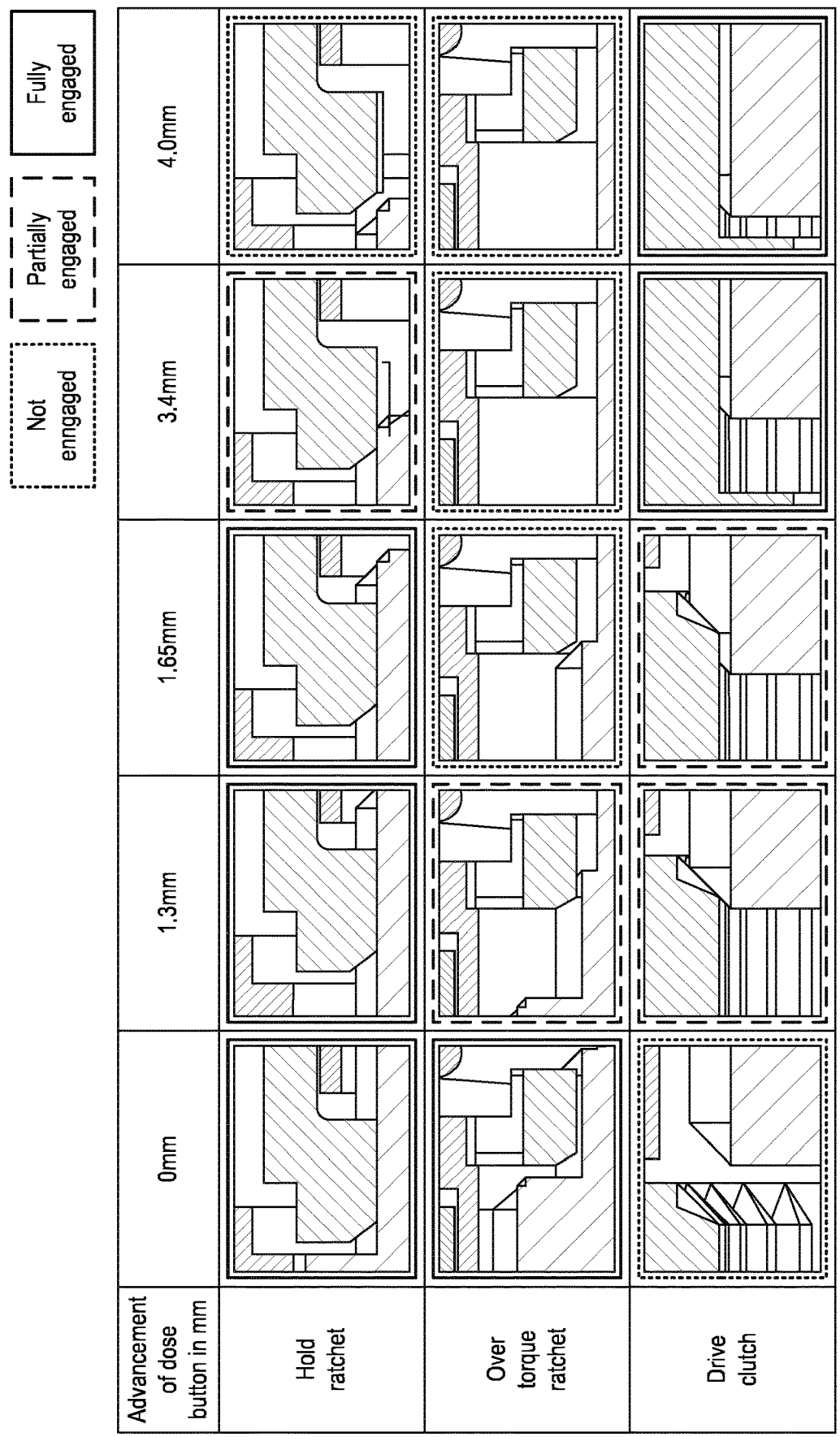
FIG. 83 is a diagrammatic summary of the key engagement points of the components of the injection device, at five stages of dose delivery.

FIG. 83 is a diagrammatic summary of the key engagement points of the components of the injection device, at five stages of dose delivery.

As with the first embodiment, described, with reference to FIGS. 1-3, the ratchet arrangement is moveable between an engaged state in which the spring 420 is limited from unwinding from a currently selected dose and a disengaged state in which the spring 420 is able to unwind. The ratchet arrangement comprises a ratchet component 410c and the splines 406 on the drive plate 405.

The drive assembly includes a plunger element 440, 446 capable of providing an axial force for ejecting a dose of medicament from the injection device 400. The drive assembly also includes a drive clutch 440b moveable from a disengaged state in which a force path from the spring 420 to the plunger element 440, 446 is interrupted and an engaged state in which the drive assembly can provide the axial force for ejecting a dose of medicament from the injection device 400 via the force path.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

REFERENCE NUMERALS 10 injection device
L longitudinal axis
10a front end of the device
10b rear end of the device
12 housing
12a aperture in the housing
14 needle
16 dose selector
18 dose indicator
20 spring
21 drive clutch
22 drive assembly
23 plunger element
24 medicament container
25 ratchet arrangement
26 force path
200 injection device
200a front end of the device
200b rear end of the device
L longitudinal axis
212 housing
212a aperture in housing
213 housing teeth
214 tabs on housing
215 clutch engaging feature on housing
216 dose selector
217 ratchet pawl
217a ratchet fingers
217b ratchet arms
218 units wheel
218a units wheel ribs
219 tens wheel
220 drive spring
221 housing top cap
222 odometer shuttle lock
224 medicament cartridge
225 cartridge holder
226 cartridge stopper
230 dose button
231 dose button spring
240 drive sleeve
240a last dose nut endstop
241 last dose nut
250 drive clutch
250a haptic feedback arm
251 drive clutch spring
252 leadscrew nut
253 leadscrew
254 thrust bearing
260 units numbers
261 units wheel drive dogs
262 units wheel engagement splines
270 tens numbers
271 max dose limit feature
272 min dose limit feature
273 tens wheel key to engage shuttle lock
280 shuttle lock peripheral teeth
281 shuttle lock keyway 282 shuttle lock dogs
283 shuttle lock rear teeth
290 housing max/min limit rib
291 housing dogs for engaging shuttle lock
292 housing engagement ribs
A backlash point for dose decrementing
300 injection device
300a front end of the device
300b rear end of the device
L longitudinal axis
312 housing
312a aperture in housing
312b internal thread in housing to guide number sleeve
312c maximum dose end stop
313 housing teeth
314 second set of housing teeth (for cap pawl)
316 dose selector
316a dose selector slots
317 selector pawl
317a selector pawl splines
317b selector pawl ratchet arm
318 number sleeve
318a splined connection of number sleeve to drive shaft
320 drive spring
321 spring lock
324 medicament cartridge
325 cartridge holder
326 cartridge stopper
330 dose button
330a ratchet disengagement finger
331 dose button spring
340 drive shaft
341 last dose nut
341a last dose nut rotational endstop
342 drive sleeve
342a drive sleeve splines
349 drive shaft splines
350 drive shaft splined clutch
351 cap pawl
351a pawls
352 body cap
353 lead screw
400 injection device
L longitudinal axis
400a front end of the device
400b rear end of the device
405 drive plate
405a drive plate flange
406 first set of drive plate engagement splines/teeth (for hold ratchet)
407 second set of drive plate engagement splines/teeth (for over-torque ratchet)
408 third set of drive plate splines (for turning drive sleeve)
409 fourth set of drive plate splines (for engaging drive shaft)
410 ratchet ring
410a ratchet ring notches for engaging with housing
410b ratchet ring ratchet arm (for hold ratchet)
410c ratchet ring first pawl
410d ratchet ring second pawl
410e ratchet ring hard stop (for number sleeve)
412 housing
412a aperture in the housing
412b housing thread
412c rotary endstop for number sleeve on internal surface of housing
416 dose selector
416a dose selector disengagement splines/teeth (for hold ratchet)
416b dose selector ratchet pawl (for over-torque ratchet)
416c dose selector grip formations
418 number sleeve
418a number sleeve longitudinal grooves
418b number sleeve helical groove
420 drive spring
424 medicament cartridge
425 cartridge holder
426 cartridge stopper
430 dose button
431 dose button spring
439 drive sleeve
439a external drive sleeve splines
439b internal drive sleeve splines
440 drive shaft
440a drive shaft rotary endstop for last dose nut
440b drive shaft internal splines (for engaging drive plate)
440c drive shaft external splines (for keying to hollow plunger)
441 last dose nut
441a last dose nut external grooves
441b last dose nut endstop
442 chassis ratchet arrangement
443 chassis
444 hollow plunger
445 thrust nut
446 plunger bearing

The invention claimed is:

1. An injection device comprising:
   a. a housing having a longitudinal axis;
   b. a dose selector capable of being rotated about said longitudinal axis with respect to said housing by a user to set a dose of medicament to be ejected from the injection device;
   c. a spring capable of storing energy necessary for ejecting the dose of medicament from the injection device, wherein the spring is coupled to the dose selector such that a charging force can be transferred from the dose selector to the spring to increase the energy stored by the spring;
   d. a ratchet arrangement moveable between an engaged state in which the spring is limited from unwinding from a currently selected dose and a disengaged state in which the spring is able to unwind; and
   e. a drive assembly including a plunger element comprising a lead screw concentrically arranged within and rotationally fixed with respect to a rotatable drive sleeve and capable of providing an axial force for ejecting the dose of medicament from the injection device, via a force path extending between the spring and the plunger element,
   wherein the drive assembly further comprises
   f. a drive clutch moveable from a disengaged state in which said force path from the spring to the plunger element is interrupted and an engaged state in which said force path is continuous and the drive assembly can provide the axial force for ejecting the dose of medicament from the injection device,
   wherein the drive clutch reaches its fully engaged state before the ratchet arrangement has reached its fully disengaged state, and
   wherein said drive clutch comprises a drive clutch component having splines on a rear face thereof, the splines being engageable with splines on a front face of said drive sleeve during forward movement of said drive sleeve.

2. The injection device of claim 1 wherein the ratchet arrangement comprises a radially-flexible ratchet arm and teeth on an internal surface of the housing.

3. The injection device of claim 1 wherein said drive clutch component comprises a drive shaft intermediate said spring and said drive sleeve.

4. The injection device of claim 1 wherein, when the drive clutch is in its disengaged state, the drive clutch component is rotationally fixed with respect to the housing.

5. The injection device of claim 1 wherein forward movement of said drive sleeve is capable of disengaging said drive clutch component from said housing, allowing relative rotation therebetween.

6. The injection device of claim 1 wherein the drive clutch is moveable from the disengaged state to the engaged state before the ratchet arrangement begins to move from the engaged state to the disengaged state.

7. The injection device of claim 1 wherein the spring is a torsion spring and the charging force transferred to the spring is a charging torque.

8. The injection device of claim 7 wherein the drive assembly has a rotational to axial coupling, where the drive assembly is rotationally drivable by the torsion spring and is arranged to provide the axial force for ejecting the dose from the injection device.

9. The injection device of claim 1 wherein, when the drive clutch is in the engaged state, the spring is coupled to the plunger element via one or more intermediate components capable of transmitting the charging force.

10. The injection device of claim 1 wherein said drive assembly is concentrically arranged about said longitudinal axis.

11. The injection device of claim 10 wherein said plunger element is radially outward of said drive clutch.

12. The injection device of claim 10 wherein said plunger element is radially inward of said drive clutch.

13. The injection device of claim 1 further comprising a medicament container.

14. The injection device of claim 13 wherein the medicament container comprises a pre-filled syringe or cartridge.

15. The injection device of claim 13 further comprising a medicament contained in the medicament container.

16. The injection device of claim 15 wherein the medicament is selected from the group comprising: antipsychotic substances including risperidone, hormones, antitoxins, substances for the control of pain, immunosuppressives, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

17. An injection device comprising:
a. a housing having a longitudinal axis;
b. a dose selector capable of being rotated about said longitudinal axis with respect to said housing by a user to set a dose of medicament to be ejected from the injection device;
c. a spring capable of storing energy necessary for ejecting the dose of medicament from the injection device, wherein the spring is coupled to the dose selector such that a charging force can be transferred from the dose selector to the spring to increase the energy stored by the spring;
d. a ratchet arrangement moveable between an engaged state in which the spring is limited from unwinding from a currently selected dose and a disengaged state in which the spring is able to unwind; and
e. a drive assembly including a plunger element capable of providing an axial force for ejecting the dose of medicament from the injection device, via a force path extending between the spring and the plunger element,
wherein the drive assembly further comprises
f. a drive clutch moveable from a disengaged state in which said force path from the spring to the plunger element is interrupted and an engaged state in which said force path is continuous and the drive assembly can provide the axial force for ejecting the dose of medicament from the injection device,
wherein the ratchet arrangement comprises a ratchet component rotationally and axially locked with respect to said housing and a drive plate including a first set of splines, and wherein the drive clutch reaches its fully engaged state before the ratchet arrangement has reached its fully disengaged state,
wherein the spring is fixed at one end to said housing and fixed at another end to a rotatable drive sleeve, and
wherein the drive assembly further comprises a drive shaft engageable with said drive sleeve to drive the plunger element.

18. The injection device of claim 17 wherein said dose selector includes splines for disengaging said ratchet arrangement.

19. The injection device of claim 18 wherein said ratchet component is capable of interacting with both the splines on the dose selector and the splines on the drive plate.

20. The injection device of claim 17 wherein the plunger element comprises a hollow plunger concentrically arranged around said drive shaft.

21. The injection device of claim 20 wherein said drive plate comprises a further set of splines configured to engage splines on said drive shaft.

22. The injection device of claim 21 wherein said further set of splines is on an outer surface of said drive plate and said drive shaft splines are on an internal surface thereof.

* * * * *